United States Patent
Gao et al.

(10) Patent No.: US 9,272,053 B2
(45) Date of Patent: Mar. 1, 2016

(54) AAV-BASED TREATMENT OF CHOLESTEROL-RELATED DISORDERS

(75) Inventors: Guangping Gao, Westborough, MA (US); Phillip D. Zamore, Northborough, MA (US); Jun Xie, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 535 days.

(21) Appl. No.: 13/642,740

(22) PCT Filed: Apr. 22, 2011

(86) PCT No.: PCT/US2011/033628
§ 371 (c)(1),
(2), (4) Date: Jan. 7, 2013

(87) PCT Pub. No.: WO2011/133901
PCT Pub. Date: Oct. 27, 2011

(65) Prior Publication Data
US 2013/0101558 A1 Apr. 25, 2013

Related U.S. Application Data

(60) Provisional application No. 61/327,383, filed on Apr. 23, 2010.

(51) Int. Cl.
| C12N 15/11 | (2006.01) |
| A61K 48/00 | (2006.01) |
| C12Q 1/68 | (2006.01) |
| C12N 15/86 | (2006.01) |

(52) U.S. Cl.
CPC ............... *A61K 48/00* (2013.01); *C12N 15/86* (2013.01); *C12Q 1/68* (2013.01); *C12N 2310/113* (2013.01); *C12N 2320/32* (2013.01); *C12N 2330/51* (2013.01); *C12N 2750/14143* (2013.01)

(58) Field of Classification Search
CPC .......................... A61K 48/00; C12N 2310/141
See application file for complete search history.

(56) References Cited

U.S. PATENT DOCUMENTS

| 5,043,270 A | 8/1991 | Abrams et al. |
| 5,399,363 A | 3/1995 | Liversidge et al. |
| 5,478,745 A | 12/1995 | Samulski et al. |
| 5,543,158 A | 8/1996 | Gref et al. |
| 5,552,157 A | 9/1996 | Yagi et al. |
| 5,565,213 A | 10/1996 | Nakamori et al. |
| 5,567,434 A | 10/1996 | Szoka |
| 5,641,515 A | 6/1997 | Ramtoola |
| 5,656,016 A | 8/1997 | Ogden |
| 5,697,899 A | 12/1997 | Hillman et al. |
| 5,738,868 A | 4/1998 | Shinkarenko |
| 5,741,516 A | 4/1998 | Webb et al. |
| 5,770,219 A | 6/1998 | Chiang et al. |
| 5,779,708 A | 7/1998 | Wu |
| 5,783,208 A | 7/1998 | Venkateshwaran et al. |
| 5,795,587 A | 8/1998 | Gao et al. |
| 5,797,898 A | 8/1998 | Santini et al. |
| 5,871,982 A | 2/1999 | Wilson et al. |
| 6,001,650 A | 12/1999 | Colosi |
| 6,083,716 A | 7/2000 | Wilson et al. |
| 6,156,303 A | 12/2000 | Russell et al. |
| 6,177,403 B1 | 1/2001 | Stedman |
| 6,251,677 B1 | 6/2001 | Wilson et al. |
| 6,365,394 B1 | 4/2002 | Gao et al. |
| 6,475,469 B1 | 11/2002 | Montgomery |
| 6,485,966 B2 | 11/2002 | Gao et al. |
| 6,498,244 B1 | 12/2002 | Patel et al. |
| 6,821,512 B1 | 11/2004 | Gao et al. |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,238,526 B2 | 7/2007 | Wilson et al. |
| 7,247,472 B2 | 7/2007 | Wilson et al. |
| 7,282,199 B2 | 10/2007 | Gao et al. |
| 7,344,872 B2 | 3/2008 | Gao et al. |
| 7,427,396 B2 | 9/2008 | Arbetman et al. |
| 7,456,015 B2 | 11/2008 | Bohn et al. |
| 7,906,111 B2 * | 3/2011 | Wilson et al. ................. 424/93.2 |
| 8,222,221 B2 * | 7/2012 | Corey et al. ................. 514/44 A |
| 8,734,809 B2 | 5/2014 | Gao et al. |
| 2002/0019050 A1 | 2/2002 | Gao et al. |

(Continued)

FOREIGN PATENT DOCUMENTS

| WO | WO 03/042397 | 5/2003 |
| WO | WO 03/093460 | 11/2003 |

(Continued)

OTHER PUBLICATIONS

Kloosterman et al. (Nucleic Acids Research, 2004, 32, pp. 6284-6291).*
GENBANK Submission; NCBI, Accession No. AAB95450; Rutledge et al.; Jan. 12, 1998.
GENBANK Submission; NCBI, Accession No. AAS99264; Gao et al.; Jun. 24, 2004.
GENBANK Submission; NCBI, Accession No. ABA71701; Schmidt et al.; May 10, 2006.
GENBANK Submission; NCBI, Accession No. ACB55301; Vandenberghe et al.; Jul. 31, 2008.
GENBANK Submission; NCBI, Accession No. ACB55310; Vandenberghe et al.; Jul. 31, 2008.
GENBANK Submission; NCBI, Accession No. NP_049542; Xiao et al.; Mar. 11, 2010.

(Continued)

*Primary Examiner* — Brian Whiteman
(74) *Attorney, Agent, or Firm* — Wolf, Greenfield & Sacks, P.C.

(57) ABSTRACT

The invention in some aspects relates to methods and compositions for assessing the effectiveness of miRNA inhibitors. In other aspects of the invention, methods and compositions for treating cholesterol related disorders are provided. In one aspect of the invention, miRNA inhibitors against miR-122 and rAAV-based compositions comprising the same are provided.

12 Claims, 19 Drawing Sheets

(56) References Cited

U.S. PATENT DOCUMENTS

| | | |
|---|---|---|
| 2003/0040101 A1 | 2/2003 | Wilson et al. |
| 2003/0092161 A1 | 5/2003 | Gao et al. |
| 2003/0096399 A1 | 5/2003 | Barber et al. |
| 2003/0119191 A1 | 6/2003 | Gao et al. |
| 2003/0138772 A1 | 7/2003 | Gao et al. |
| 2003/0207259 A1 | 11/2003 | Gao et al. |
| 2003/0228282 A1 | 12/2003 | Gao et al. |
| 2004/0136963 A1 | 7/2004 | Wilson et al. |
| 2004/0171807 A1 | 9/2004 | Gao et al. |
| 2005/0014262 A1 | 1/2005 | Gao et al. |
| 2005/0032219 A1 | 2/2005 | Aubourg et al. |
| 2005/0037988 A1 | 2/2005 | Zamore et al. |
| 2005/0069866 A1 | 3/2005 | Wilson et al. |
| 2005/0137153 A1 | 6/2005 | McSwiggen et al. |
| 2006/0018841 A1 | 1/2006 | Arbetman et al. |
| 2006/0063174 A1 | 3/2006 | Turner et al. |
| 2006/0292117 A1 | 12/2006 | Loiler et al. |
| 2007/0004042 A1 | 1/2007 | Gao et al. |
| 2007/0036760 A1 | 2/2007 | Wilson et al. |
| 2007/0134203 A1 | 6/2007 | Gao et al. |
| 2007/0292410 A1 | 12/2007 | Cashman et al. |
| 2008/0075737 A1 | 3/2008 | Gao et al. |
| 2008/0075740 A1 | 3/2008 | Gao et al. |
| 2008/0090281 A1 | 4/2008 | Wilson et al. |
| 2008/0219954 A1 | 9/2008 | Gao et al. |
| 2008/0292595 A1 | 11/2008 | Arbetman et al. |
| 2009/0111766 A1 | 4/2009 | Atkinson et al. |
| 2009/0131355 A1 | 5/2009 | Bot et al. |
| 2009/0149409 A1 | 6/2009 | Bohn et al. |
| 2010/0028998 A1 | 2/2010 | Roelvink et al. |
| 2010/0104561 A1 | 4/2010 | Zhong et al. |
| 2010/0186103 A1 | 7/2010 | Gao et al. |
| 2010/0323001 A1 | 12/2010 | Pachuk |
| 2010/0323356 A1* | 12/2010 | Inoue et al. .................. 435/6 |
| 2011/0172293 A1* | 7/2011 | Fish et al. .................. 514/44 A |
| 2011/0258716 A1 | 10/2011 | Baltimore et al. |
| 2012/0137379 A1 | 5/2012 | Gao et al. |
| 2013/0195801 A1 | 8/2013 | Gao et al. |
| 2013/0281516 A1 | 10/2013 | Gao et al. |
| 2014/0142161 A1 | 5/2014 | Flotte et al. |
| 2014/0296486 A1 | 10/2014 | Gao et al. |
| 2014/0335054 A1 | 11/2014 | Gao et al. |

FOREIGN PATENT DOCUMENTS

| | | |
|---|---|---|
| WO | WO 2004/108922 A2 | 12/2004 |
| WO | WO 2005/033321 | 4/2005 |
| WO | WO 2006/119432 A2 | 11/2006 |
| WO | WO 2007/000668 A2 | 1/2007 |
| WO | WO 2007/027775 A2 | 3/2007 |
| WO | WO 2008/091703 | 7/2008 |
| WO | WO 2008/147839 A1 | 12/2008 |
| WO | WO 2008/150897 A2 | 12/2008 |
| WO | WO 2009/109665 A1 | 9/2009 |
| WO | WO 2009/130208 | 10/2009 |
| WO | WO 2009/146178 A1 | 12/2009 |
| WO | WO 2010/034314 A1 | 4/2010 |
| WO | WO 2010/071454 A1 | 6/2010 |
| WO | WO 2010/129021 A1 | 11/2010 |
| WO | WO 2010/138263 A2 | 12/2010 |
| WO | WO 2013/190059 A1 | 12/2013 |

OTHER PUBLICATIONS

GENBANK Submission; NCBI, Accession No. YP_680426; Ruffing et al.; Nov. 19, 2010.

Genbank Submission; Accession No. ADZ26851; Wilson et al.; Jun. 30, 2005.

Afione et al., In vivo model of adeno-associated virus vector persistence and rescue. J Virol. May 1996;70(5):3235-41.

Akache et al., The 37/67-kilodalton laminin receptor is a receptor for adeno-associated virus serotypes 8, 2, 3, and 9. J Virol. Oct. 2006;80(19):9831-6.

Alisky et al., Gene therapy for amyotrophic lateral sclerosis and other motor neuron diseases. Hum Gene Ther. Nov. 20, 2000;11(17):2315-29.

Ameres et al., Target RNA-directed tailing and trimming purifies the sorting of endo-siRNAs between the two *Drosophila argonaute* proteins. RNA. Jan. 2011;17(1):54-63. doi: 10.1261/rna.2498411. Epub Nov. 24, 2010.

Ameres et al., Target RNA-directed trimming and tailing of small silencing RNAs. Science. Jun. 18, 2010;328(5985):1534-9. doi: 10.1126/science.1187058.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Azzouz et al., VEGF delivery with retrogradely transported lentivector prolongs survival in a mouse ALS model. Nature. May 27, 2004;429(6990):413-7.

Bals et al., Transduction of well-differentiated airway epithelium by recombinant adeno-associated virus is limited by vector entry. J Virol. Jul. 1999;73(7):6085-8.

Barcia et al., Intraventricular and intracerebral delivery of anti-epileptic drugs in the kindling model. Neurotherapeutics. Apr. 2009;6(2):337-43.

Bernacki et al., Mucin gene expression during differentiation of human airway epithelia in vitro. Muc4 and muc5b are strongly induced. Am J Respir Cell Mol Biol. Apr. 1999;20(4):595-604.

Berns et al., Biology of adeno-associated virus. Curr Top Microbiol Immunol. 1996;218:1-23.

Berns et al., Detection of adeno-associated virus (AAV)-specific nucleotide sequences in DNA isolated from latently infected Detroit 6 cells. Virology. Dec. 1975;68(2):556-60.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Boillée et al., Onset and progression in inherited ALS determined by motor neurons and microglia. Science. Jun. 2, 2006;312(5778):1389-92.

Bolstad et al., A comparison of normalization methods for high density oligonucleotide array data based on variance and bias. Bioinformatics. Jan. 22, 2003;19(2):185-93.

Bourlais et al., Ophthalmic drug delivery systems—recent advances. Prog Retin Eye Res. Jan. 1998;17(1):33-58.

Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.

Brown et al., A microRNA-regulated lentiviral vector mediates stable correction of hemophilia B mice. Blood. Dec. 15, 2007;110(13):4144-52. Epub Aug. 28, 2007.

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.

Brown et al., Endogenous microRNA regulation suppresses transgene expression in hematopoietic lineages and enables stable gene transfer. Nat Med. May 2006;12(5):585-91. Epub Apr. 23, 2006.

Bukh, A critical role for the chimpanzee model in the study of hepatitis C. Hepatology. Jun. 2004;39(6):1469-75.

Büssing et al., let-7 microRNAs in development, stem cells and cancer. Trends Mol Med. Sep. 2008;14(9):400-9. doi: 10.1016/j.molmed.2008.07.001. Epub Jul. 31, 2008.

Calcedo et al., Worldwide epidemiology of neutralizing antibodies to adeno-associated viruses. J Infect Dis. Feb. 1, 2009;199(3):381-90.

Carè et al., MicroRNA-133 controls cardiac hypertrophy. Nat Med. May 2007;13(5):613-8. Epub Apr. 29, 2007.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Chadderton et al., Improved retinal function in a mouse model of dominant retinitis pigmentosa following AAV-delivered gene therapy. Mol Ther. Apr. 2009;17(4):593-9. Epub Jan. 27, 2009.

(56) References Cited

OTHER PUBLICATIONS

Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chirmule et al., Humoral immunity to adeno-associated virus type 2 vectors following administration to murine and nonhuman primate muscle. J Virol. Mar. 2000;74(5):2420-5.
Choi et al., Effects of adeno-associated virus DNA hairpin structure on recombination. J Virol. Jun. 2005;79(11):6801-7.
Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.
Chu et al., SV40 DNA transfection of cells in suspension: analysis of efficiency of transcription and translation of T-antigen. Gene. Mar. 1981;13(2):197-202.
Cideciyan et al., Human RPE65 gene therapy for Leber congenital amaurosis: persistence of early visual improvements and safety at 1 year. Hum Gene Ther. Sep. 2009;20(9):999-1004.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conrad et al., Safety of single-dose administration of an adeno-associated virus (AAV)-CFTR vector in the primate lung. Gene Ther. Aug. 1996;3(8):658-68.
Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.
Crowe et al., A comparison in chimpanzees of the immunogenicity and efficacy of live attenuated respiratory syncytial virus (RSV) temperature-sensitive mutant vaccines and vaccinia virus recombinants that express the surface glycoproteins of RSV. Vaccine. Nov. 1993;11(14):1395-404.
Cruz et al., in vivo post-transcriptional gene silencing of alpha-1 antitrypsin by adeno-associated virus vectors expressing siRNA. Lab Invest. Sep. 2007;87(9):893-902. Epub Jun. 25, 2007.
Curtin et al., Bidirectional promoter interference between two widely used internal heterologous promoters in a late-generation lentiviral construct. Gene Ther. Mar. 2008;15(5):384-90. doi: 10.1038/sj.gt.3303105. Epub Jan. 24, 2008.
Czech, MicroRNAs as therapeutic targets. N Engl J Med. Mar. 16, 2006;354(11):1194-5.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Di Giorgio et al., Non-cell autonomous effect of glia on motor neurons in an embryonic stem cell-based ALS model. Nat Neurosci. May 2007;10(5):608-14. Epub Apr. 15, 2007.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.
Ebert et al., MicroRNA sponges: competitive inhibitors of small RNAs in mammalian cells. Nat Methods. Sep. 2007;4(9):721-6. Epub Aug. 12, 2007.
Ehlert et al., Cellular toxicity following application of adeno-associated viral vector-mediated RNA interference in the nervous system. BMC Neurosci. Feb. 18, 2010;11:20.
Elmén et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Elmén et al., LNA-mediated microRNA silencing in non-human primates. Nature. Apr. 17, 2008;452(7189):896-9. Epub Mar. 26, 2008.
Engelhardt et al., Adenovirus-mediated transfer of the CFTR gene to lung of nonhuman primates: biological efficacy study. Hum Gene Ther. Dec. 1993;4(6):759-69.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fire et al., Potent and specific genetic interference by double-stranded RNA in Caenorhabditis elegans. Nature. Feb. 19, 1998;391(6669):806-11.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes in CNS. Nature Biotechnology, 27; 59-65 2009.
Fu et al., Evaluation of cellular immune responses in subjects chronically infected with HIV type 1. AIDS Res Hum Retroviruses. Jan. 2007;23(1):67-76.
Fu et al., Self-complementary adeno-associated virus serotype 2 vector: global distribution and broad dispersion of AAV-mediated transgene expression in mouse brain. Mol Ther. Dec. 2003;8(6):911-7.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Adeno-associated virus-mediated gene transfer to nonhuman primate liver can elicit destructive transgene-specific T cell responses. Hum Gene Ther. Sep. 2009;20(9):930-42. doi: 10.1089/hum.2009.060.
Gao et al., Biology of AAV serotype vectors in liver-directed gene transfer to nonhuman primates. Mol Ther. Jan. 2006;13(1):77-87. Epub Oct. 10, 2005.
Gao et al., Clades of Adeno-associated viruses are widely disseminated in human tissues. J Virol. Jun. 2004;78(12):6381-8.

(56) References Cited

OTHER PUBLICATIONS

Gao et al., Erythropoietin gene therapy leads to autoimmune anemia in macaques. Blood. May 1, 2004;103(9):3300-2. Epub Dec. 24, 2003.

Gao et al., In situ synthesis of oligonucleotide microarrays. Biopolymers. Apr. 5, 2004;73(5):579-96.

Gao et al., Inadvertent gene transfer of co-packaged rep and cap sequences during the production of AAV vector and its potential impact on vector performance Molecular Therapy. May 2008;16(Suppl. 1):S105-S106. Abstract 279.

Gao et al., New recombinant serotypes of AAV vectors. Curr Gene Ther. Jun. 2005;5(3):285-97.

Gao et al., Novel adeno-associated viruses from rhesus monkeys as vectors for human gene therapy. Proc Natl Acad Sci U S A. Sep. 3, 2002;99(18):11854-9. Epub Aug. 21, 2002.

Gao et al., Purification of recombinant adeno-associated virus vectors by column chromatography and its performance in vivo. Hum Gene Ther. Oct. 10, 2000;11(15):2079-91.

Gao et al., RAAV-mediated targeting in adult mice and its potential in generating animal models of tissue-specific somatic transgenics or knock down. Molecular Therapy. May 2008;16(1):S118-S119. Abstract 316.

Gentner et al., Stable knockdown of microRNA in vivo by lentiviral vectors. Nat Methods. Jan. 2009;6(1):63-6. doi: 10.1038/nmeth.1277. Epub Nov. 30, 2008.

Girard et al., miR-122, a paradigm for the role of microRNAs in the liver. J Hepatol. Apr. 2008;48(4):648-56. doi: 10.1016/j.jhep.2008.01.019. Epub Feb. 12, 2008.

Graham et al., A new technique for the assay of infectivity of human adenovirus 5 DNA. Virology. Apr. 1973;52(2):456-67.

Gramantieri et al., Cyclin G1 is a target of miR-122a, a microRNA frequently down-regulated in human hepatocellular carcinoma. Cancer Res. Jul. 1, 2007;67(13):6092-9.

Griffiths-Jones et al., miRBase: microRNA sequences, targets and gene nomenclature. Nucleic Acids Res. Jan. 1, 2006;34(Database issue):D140-4.

Grimm et al., Fatality in mice due to oversaturation of cellular microRNA/short hairpin RNA pathways. Nature. May 25, 2006;441(7092):537-41.

Gruenert et al., Culture and transformation of human airway epithelial cells. Am J Physiol. Mar. 1995;268(3 Pt 1):L347-60.

Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.

Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.

Hernandez et al., Latent adeno-associated virus infection elicits humoral but not cell-mediated immune responses in a nonhuman primate model. J Virol. Oct. 1999;73(10):8549-58.

Hildinger et al., Hybrid vectors based on adeno-associated virus serotypes 2 and 5 for muscle-directed gene transfer. J Virol. Jul. 2001;75(13):6199-203.

Horwich et al., Design and delivery of antisense oligonucleotides to block microRNA function in cultured *Drosophila* and human cells. Nat Protoc. 2008;3(10):1537-49. doi: 10.1038/nprot.2008.145.

Hutvágner et al., Sequence-specific inhibition of small RNA function. PLoS Biol. Apr. 2004;2(4):E98. Epub Feb. 24, 2004.

Jackman et al., Stabilization of the oxy form of tyrosinase by a single conservative amino acid substitution. Biochem J. Mar. 15, 1992;282 ( Pt 3):915-8.

Johnson et al., RAS is regulated by the let-7 microRNA family. Cell. Mar. 11, 2005;120(5):635-47.

Kaspar et al., Retrograde viral delivery of IGF-1 prolongs survival in a mouse ALS model. Science. Aug. 8, 2003;301(5634):839-42.

Kota et al., Therapeutic microRNA delivery suppresses tumorigenesis in a murine liver cancer model. Cell. Jun. 12, 2009;137(6):1005-17. doi: 10.1016/j.cell.2009.04.021.

Kotin et al., Organization of adeno-associated virus DNA in latently infected Detroit 6 cells. Virology. Jun. 1989;170(2):460-7.

Kotin et al., Site-specific integration by adeno-associated virus. Proc Natl Acad Sci U S A. Mar. 1990;87(6):2211-5.

Krützfeldt et al., Silencing of microRNAs in vivo with 'antagomirs'. Nature. Dec. 1, 2005;438(7068):685-9. Epub Oct. 30, 2005.

Kutay et al., Downregulation of miR-122 in the rodent and human hepatocellular carcinomas. J Cell Biochem. Oct. 15, 2006;99(3):671-8.

Kwiatkowski et al., Clinical, genetic, and pharmacogenetic applications of the Invader assay. Mol Diagn. Dec. 1999;4(4):353-64.

Lanford et al., Therapeutic silencing of microRNA-122 in primates with chronic hepatitis C virus infection. Science. Jan. 8, 2010;327(5962):198-201. Epub Dec. 3, 2009.

Lebherz et al., Gene therapy with novel adeno-associated virus vectors substantially diminishes atherosclerosis in a murine model of familial hypercholesterolemia. J Gene Med. Jun. 2004;6(6):663-72.

Lewis et al., Conserved seed pairing, often flanked by adenosines, indicates that thousands of human genes are microRNA targets. Cell. Jan. 14, 2005;120(1):15-20.

Lewis et al., Prediction of mammalian microRNA targets. Cell. Dec. 26, 2003;115(7):787-98.

Li et al., Ex vivo transduction and transplantation of bone marrow cells for liver gene delivery of alpha1-antitrypsin. Mol Ther. Aug. 2010;18(8):1553-8. Epub Jun. 15, 2010.

Lin et al., Impact of preexisting vector immunity on the efficacy of adeno-associated virus-based HIV-1 Gag vaccines. Hum Gene Ther. Jul. 2008;19(7):663-9.

Liu et al., Biological Differences in rAAV Transduction of Airway Epithelia in Humans and in Old World Non-human Primates. Mol Ther. Dec. 2007;15(12):2114-23. Epub Jul. 31, 2007.

Liu et al., Comparative biology of rAAV transduction in ferret, pig and human airway epithelia. Gene Ther. Nov. 2007;14(21):1543-8. Epub Aug. 30, 2007.

Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.

Lomas et al., The mechanism of Z alpha 1-antitrypsin accumulation in the liver. Nature. Jun. 18, 1992;357(6379):605-7.

Lowenstein, Crossing the rubicon. Nat Biotechnol. Jan. 2009;27(1):42-4.

Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.

Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.

Mandel et al., Recombinant adeno-associated viral vectors as therapeutic agents to treat neurological disorders. Mol Ther. Mar. 2006;13(3):463-83. Epub Jan. 18, 2006.

Manfredsson et al., AAV9: a potential blood-brain barrier buster. Mol Ther. Mar. 2009;17(3):403-5.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].

Martin-Duque et al., Direct comparison of the insulating properties of two genetic elements in an adenoviral vector containing two different expression cassettes. Hum Gene Ther. Oct. 2004;15(10):995-1002.

McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.

McCarty et al., Integration of adeno-associated virus (AAV) and recombinant AAV vectors. Annu Rev Genet. 2004;38:819-45.

McCarty et al., Self-complementary recombinant adeno-associated virus (scAAV) vectors promote efficient transduction independently of DNA synthesis. Gene Ther. Aug. 2001;8(16):1248-54.

McCarty, Self-complementary AAV vectors; advances and applications. Mol Ther. Oct. 2008;16(10):1648-56. Epub Aug. 5, 2008.

(56) References Cited

OTHER PUBLICATIONS

McGovern, Taking aim at HDL-C. Raising levels to reduce cardiovascular risk. Postgrad Med. Apr. 2005;117(4):29-30, 33-5, 39 passim.
McLean et al., Gene targeted therapeutics for liver disease in alpha-1 antitrypsin deficiency. Biologics. 2009;3:63-75. Epub Jul. 13, 2009.
Meister et al., Sequence-specific inhibition of microRNA- and siRNA-induced RNA silencing. RNA. Mar. 2004;10(3):544-50.
Mingozzi et al., CD8(+) T-cell responses to adeno-associated virus capsid in humans. Nat Med. Apr. 2007;13(4):419-22. Epub Mar. 18, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):5391-5392. Abstract 1030.
Mueller et al., In Vivo AAV Delivered Allele Specific shRNA for the Knockdown of Alpha-1 Antitrypsin. Molecular Therapy May 2010;18(1):522. Abstract 53.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., The pros and cons of immunomodulatory IL-10 gene therapy with recombinant AAV in a Cftr-/--dependent allergy mouse model. Gene Ther. Feb. 2009;16(2):172-83. Epub Sep. 25, 2008.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
Nagai et al., Astrocytes expressing ALS-linked mutated SOD1 release factors selectively toxic to motor neurons. Nat Neurosci. May 2007;10(5):615-22.
Nakabayashi et al., Growth of human hepatoma cells lines with differentiated functions in chemically defined medium. Cancer Res. Sep. 1982;42(9):3858-63.
O'Reilly et al., RNA interference-mediated suppression and replacement of human rhodopsin in vivo. Am J Hum Genet. Jul. 2007;81(1):127-35. Epub May 23, 2007.
Papaioannou et al., Efficacy of tribromoethanol anesthesia in mice. Lab Anim Sci. Apr. 1993;43(2):189-92.
Powell-Braxton et al., A mouse model of human familial hypercholesterolemia: markedly elevated low density lipoprotein cholesterol levels and severe atherosclerosis on a low-fat chow diet. Nat Med. Aug. 1998;4(8):934-8. Erratum in: Nat Med Oct. 1998;4(10):1200.
Propst et al., Prevalence of hepatocellular carcinoma in alpha-1-antitrypsin deficiency. J Hepatol. Dec. 1994;21(6):1006-11.
Ralph et al., Silencing mutant SOD1 using RNAi protects against neurodegeneration and extends survival in an ALS model. Nat Med. Apr. 2005;11(4):429-33. Epub Mar. 13, 2005.
Raoul et al., Lentiviral-mediated silencing of SOD1 through RNA interference retards disease onset and progression in a mouse model of ALS. Nat Med. Apr. 2005;11(4):423-8. Epub Mar. 13, 2005.
Rayner et al., MiR-33 contributes to the regulation of cholesterol homeostasis. Science. Jun. 18, 2010;328(5985):1570-3. doi: 10.1126/science.1189862. Epub May 13, 2010.
Remington's Pharmaceutical Sciences. 15th Edition.1035-1038 and 1570-1580.
Roy et al., Characterization of a family of chimpanzee adenoviruses and development of molecular clones for gene transfer vectors. Hum Gene Ther. May 2004;15(5):519-30.
Sambrook et al, "Molecular Cloning. A Laboratory Manual", 2d ed., Cold Spring Harbor Laboratory, New York (1989).
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Schnepp et al., Characterization of adeno-associated virus genomes isolated from human tissues. J Virol. Dec. 2005;79(23):14793-803.
Schwarz et al., Designing siRNA that distinguish between genes that differ by a single nucleotide. PLoS Genet. Sep. 8, 2006;2(9):e140, 1307-1318. Epub Jul. 24, 2006.
Seiler et al., Adeno-associated virus types 5 and 6 use distinct receptors for cell entry. Hum Gene Ther. Jan. 2006;17(1):10-9.
Sen et al., Micromanaging vascular biology: tiny microRNAs play big band. J Vasc Res. 2009;46(6):527-40. doi: 10.1159/000226221. Epub Jun. 30, 2009.
Sivasothy et al., Pathogenic alpha 1-antitrypsin polymers are formed by reactive loop-beta-sheet A linkage. J Biol Chem. Oct. 27, 2000;275(43) 33663-8.
Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.
Soutar et al., Mechanisms of disease: genetic causes of familial hypercholesterolemia. Nat Clin Pract Cardiovasc Med. Apr. 2007;4(4):214-25.
Stein et al., Systemic and central nervous system correction of lysosomal storage in mucopolysaccharidosis type VII mice. J Virol. Apr. 1999;73(4):3424-9.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Tannous, Gaussia luciferase reporter assay for monitoring biological processes in culture and in vivo. Nat Protoc. 2009;4(4):582-91. doi: 10.1038/nprot.2009.28.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.
Vermeulen et al., Double-stranded regions are essential design components of potent inhibitors of RISC function. RNA. May 2007;13(5):723-30. Epub Mar. 30, 2007.
Virella-Lowell et al., Enhancing rAAV vector expression in the lung. J Gene Med. Jul. 2005;7(7):842-50.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., Vascular endothelial growth factor overexpression delays neurodegeneration and prolongs survival in amyotrophic lateral sclerosis mice. J Neurosci. Jan. 10, 2007;27(2):304-7.
Wu et al., Alpha2,3 and alpha2,6 N-linked sialic acids facilitate efficient binding and transduction by adeno-associated virus types 1 and 6. J Virol. Sep. 2006;80(18):9093-103.
Wu et al., Chronic lumbar catheterization of the spinal subarachnoid space in mice. J Neurosci Methods. Feb. 15, 2004;133(1-2):65-9.
Wu et al., Nerve injection of viral vectors efficiently transfers transgenes into motor neurons and delivers RNAi therapy against ALS. Antioxid Redox Signal. Jul. 2009;11(7):1523-34.

(56) References Cited

OTHER PUBLICATIONS

Xia et al., Allele-specific RNAi selectively silences mutant SOD1 and achieves significant therapeutic benefit in vivo. Neurobiol Dis. Sep. 2006;23(3):578-86. Epub Jul. 20, 2006.

Xia et al., Multiple shRNAs expressed by an inducible pol II promoter can knock down the expression of multiple target genes. Biotechniques. Jul. 2006;41(1):64-8.

Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.

Xie et al., Characterization of positioning effect of pol III-shRNA transcription unit in scAAV vector genome on the packaging efficiency and functionality of shRNA silencing. Molecular Therapy. May 2010;18(1): 5262. Abstract 671.

Xie et al., MicroRNA regulated tissue specific transduction by rAAV vector. Molecular Therapy. May 2009;17(1): 5279. Abstract 732.

Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1): 5140. Abstract 362.

Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.

Yan et al., Unique biologic properties of recombinant AAV1 transduction in polarized human airway epithelia. J Biol Chem. Oct. 6, 2006;281(40):29684-92. Epub Aug. 9, 2006.

Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.

Yu et al., let-7 regulates self renewal and tumorigenicity of breast cancer cells. Cell. Dec. 14, 2007;131(6):1109-23.

Zabner et al., Adeno-associated virus type 5 (AAV5) but not AAV2 binds to the apical surfaces of airway epithelia and facilitates gene transfer. J Virol. Apr. 2000;74(8):3852-8.

Zern et al., A novel SV40-based vector successfully transduces and expresses an alpha 1-antitrypsin ribozyme in a human hepatoma-derived cell line. Gene Ther. Jan. 1999;6(1):114-20.

Zhang et al., Characterization of 12 AAV vectors for intravascular delivery to target CNS and detarget non-CNS tissues by mirna regulation: implications in treatment of canavan disease. Molecular Therapy. May 2010;18(1): 5174. Abstract 450.

Zhong et al., Chimpanzee-derived novel natural variants of aav9: vector development and interrogation of correlations between capsid structure and vector biology. Molecular Therapy. May 2010;18(1): S24. Abstract 58.

Zolotukhin et al., Production and purification of serotype 1, 2, and 5 recombinant adeno-associated viral vectors. Methods. Oct. 2002;28(2):158-67.

Arbuthnot et al., Hepatic delivery of RNA interference activators for therapeutic application. Curr Gene Ther. Apr. 2009;9(2):91-103.

Haussecker et al., miR-122 continues to blaze the trail for microRNA therapeutics. Mol Ther. Feb. 2010;18(2):240-2. doi: 10.1038/mt.2009.313.

Kota et al., AAV8-Mediated Delivery of miR-26a inhibits cancer cell proliferation and induces tumor-specific apoptosis in a liver cancer model. Mol. Therapy. May 2009. 17(1):5300. Abstract 783.

Li et al., Intronic microRNA: discovery and biological implications. DNA Cell Biol. Apr. 2007;26(4):195-207.

Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.

Wang et al., The design of vectors for RNAi delivery system. Curr Pharm Des. 2008;14(13):1327-40.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

* cited by examiner

A. TuD miR-122 Inhibitor Derepresses Reporter Gene Expression in 293 cells

B. TuD miR-122 Inhibitor Derepresses Reporter Gene Expression in Huh-7 cells

C. rAAV Expressed TuD miR-122 Inhibitor effectively knocks down mature free miR-122 in mouse liver

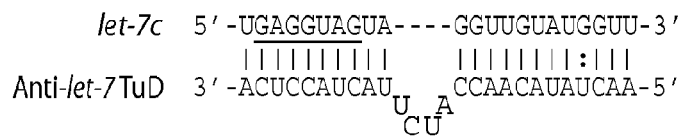
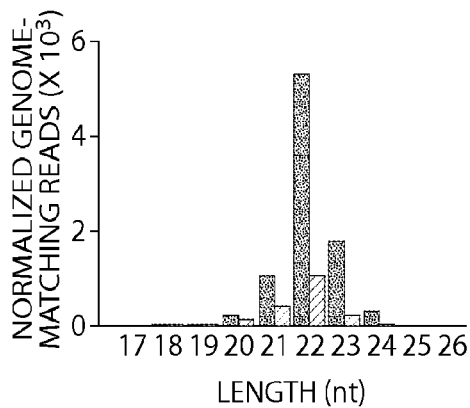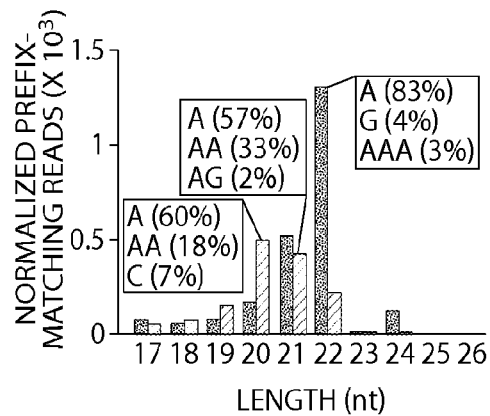
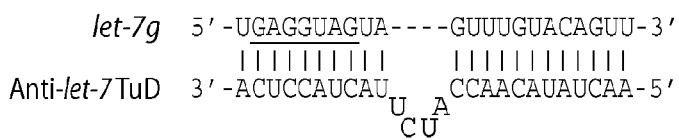
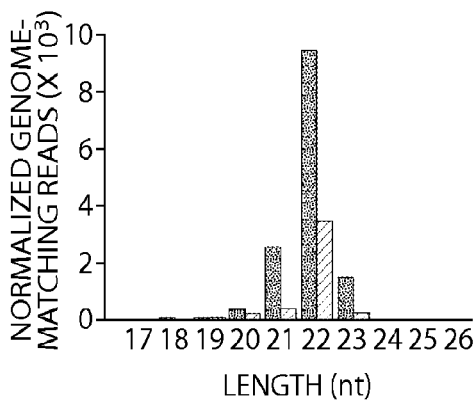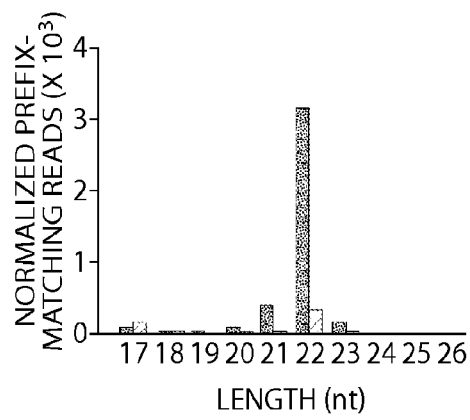
Fig. 13-4

US 9,272,053 B2

AAV-BASED TREATMENT OF CHOLESTEROL-RELATED DISORDERS

RELATED APPLICATIONS

This application is a National Stage Application of PCT/US2011/033628, filed on Apr. 22, 2011, and entitled "AAV-Based Treatment of Cholesterol-Related Disorders," which claims priority under 35 U.S.C. §119(e) of U.S. provisional application U.S. Ser. No. 61/327,383, filed Apr. 23, 2010, and entitled "AAV-based treatment of cholesterol-related disorders," the entire contents of which are incorporated herein by reference.

GOVERNMENT SUPPORT

This work was supported under grant nos. P01 HL59407-11, 2R37GM62862 and 2R01GM65236 awarded by the National Institutes of Health. The U.S. government as certain rights in the invention.

FIELD OF THE INVENTION

The invention in some aspects relates to methods and compositions for assessing the effectiveness of miRNA inhibitors. In other aspects of the invention, methods and compositions for treating cholesterol related disorders are provided.

BACKGROUND OF INVENTION

Dyslipidemia is associated with defects in cholesterol metabolism and represents a major risk factor for cardiovascular disease, the most common cause of morbidity and mortality in the US. One common inherited form of dyslipidemia is the metabolic defect in low density lipoproteins (LDL) [familial hypercholesterolemia (FH)] caused by genetic mutations in the LDL receptor (LDLR) gene. MicroRNAs (miRNAs) are small regulatory RNAs that are important in development and progression of disease. It is understood that certain microRNAs have a role cholesterol metabolism. A highly abundant miRNA in the liver, miR-122, which does not directly target LDLR mRNA, regulates cholesterol metabolism by an unknown mechanism. A locked nucleic acid based oligonucleotide inhibitor of miR-122 has been shown to reduce total plasma cholesterol levels in a dose dependent manner (See, e.g., Elmen J, et al. Nature, 2008, 452: 896-900.) However, such oligonucleotide based inhibitors require doses impractical for a therapeutic agent. Furthermore, since the oligonucleotides are administered in finite quantities, repeated administration is required to maintain a long term inhibitory effects, which are necessary for many cholesterol-related disorders, like FH. Notwithstanding the link between miRNAs and cholesterol, and prospects of effective therapeutic agents that treat cholesterol-related disorders by modulating miRNA function, the development of effective and safe approaches for miRNA inhibition in the treatment of cholesterol related disorders has been a significant scientific and therapeutic challenge (See, e.g., Czech, M P. N Engl. J. Med. 354; 11 pg. 1144-1145. (2006).)

SUMMARY OF INVENTION

Aspects of the invention are based on molecular sensing systems that enable the assessment and characterization of miRNA inhibitor function and thereby facilitate the discovery of miRNA inhibitors that are useful for treating and studying disease, e.g., cholesterol-related disorders. According to some aspects of the invention, miRNA inhibitors are identified herein that are useful for treating cholesterol-related disorders. In some embodiments, rAAV-based miRNA inhibitor compositions are used to effect sustained, tissue specific miRNA inhibition in a subject. In some aspects, a rAAV of the invention harbors at least one transgene that expresses a miRNA inhibitor that inhibits the function, processing and/or expression of miR-122 in the subject. An exemplary miRNA inhibitor of the invention has a sequence as set forth in SEQ ID NO: 1.

According to some aspects of the invention, methods are provided for treating a high cholesterol-related disorder in a subject. In some embodiments, the methods involve administering to a subject an effective amount of a rAAV that harbors at least one transgene that expresses a miRNA inhibitor that inhibits the expression of miR-122 in the subject. In some embodiments, the miRNA inhibitor comprises an miR-122 binding site. In some embodiments, the miR-122 binding site is flanked by two stem sequences. In some embodiments, the miR-122 binding site comprises a non-binding, central portion that is not complementary with miR-122, flanked by two portions that are complementary with miR-122. In some embodiments, the miRNA inhibitor comprises a first miR-122 binding site and a second miR-122 binding site, each binding site flanked by two stem sequences, wherein a first stem sequence flanks the first miR-122 binding site at its 5'-end, a second stem sequence flanks the first miR-122 binding site at its 3'-end and the second miR-122 binding site at its 5'-end, and a third stem sequence flanks the second miR-122 binding site at its 3'-end. In some embodiments, each of the two miR-122 inhibitor binding sites comprises a non-binding, central portion that is not complementary with miR-122. In some embodiments, the non-binding, central portion of the first miR-122 binding site is at least partially complementary with the non-binding, central portion of the second miR-122 binding site. In some embodiments, the non-binding, central portion of the first miR-122 binding site is complementary with the non-binding, central portion of the second miR-122 binding site at 1 to 5 nucleotides. In some embodiments, the non-binding, central portion of the first miR-122 binding site is complementary with the non-binding, central portion of the second miR-122 binding site at 3 nucleotides. In some embodiments, the non-binding, central portion of the first miR-122 binding site has a length in a range of 1 to 10 nucleotides. In some embodiments, the non-binding, central portion of the first miR-122 binding site has a length in a range of 3 to 5 nucleotides. In some embodiments, the non-binding, central portion of the first miR-122 binding site has a length in a range of 4 nucleotides. In some embodiments, the non-binding, central portion of the second miR-122 binding site has a length in a range of 1 to 10 nucleotides. In some embodiments, the non-binding, central portion of the second miR-122 binding site has a length in a range of 3 to 5 nucleotides. In some embodiments, the non-binding, central portion of the second miR-122 binding site has a length in a range of 4 nucleotides. In some embodiments, the first miR-122 binding and the second miR-122 binding site are complementary at a sequence of 2 to 10 nucleotides in length. In some embodiments, the first miR-122 binding and the second miR-122 binding site are complementary at a sequence of 4 nucleotides in length. In some embodiments, the miRNA inhibitor comprises two or more miR-122 binding sites. In certain embodiments, the miRNA inhibitor has a sequence as set forth in SEQ ID NO: 1.

In certain embodiments, the rAAV has a capsid of the AAV9 serotype, which has a sequence as set forth in SEQ ID NO: 3. In some embodiments, the rAAV has a capsid that is a variant of the capsid of the AAV9 serotype. In certain embodiments, the rAAV has a capsid of the AAV9 serotype variant, Csp-3, which has a sequence as set forth in SEQ ID NO: 4. In some embodiments, the rAAV targets liver tissue. In some embodiments, the rAAV transduces hepatocytes. In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

In some embodiments, administering is performed intravenously. In some embodiments, administering is performed by injection into the hepatic portal vein. In some embodiments, the subject is a mouse, a rat, a rabbit, a dog, a cat, a sheep, a pig, or a non-human primate. In some embodiments, the subject is a human. In some embodiments, the subject is an animal model of a high cholesterol-related disorder. In some embodiments, the high cholesterol-related disorder is Type I, Type IIa, Type IIb, Type III, Type IV, or Type V Hyperlipoproteinemia. In some embodiments, the high cholesterol-related disorder is associated with diabetes mellitus, metabolic syndrome, kidney disease (nephrotic syndrome), hypothyroidism, Cushing's syndrome, anorexia nervosa, sleep deprivation, Zieve's syndrome, antiretroviral drugs, diet, high body weight, or low physical activity. In some embodiments, the subject is a human and the high cholesterol-related disorder is characterized by total serum cholesterol level greater than or equal to 200 mg/dl. In some embodiments, the subject is a mouse and the high cholesterol-related disorder is characterized by total serum cholesterol level greater than or equal to 100 mg/dl. In some embodiments, the subject is a rat and the high cholesterol-related disorder is characterized by total serum cholesterol level greater than or equal to 70 mg/dl.

According to some aspects of the invention a nucleic acid vector is provided for assessing the function of a miRNA inhibitor. In some embodiments, the nucleic acid vectors comprise: (a) a first promoter operably linked with a transgene that comprises: (i.) a protein coding region, and (ii.) at least one binding site of a test miRNA; and (b) a second promoter operably linked with a miRNA inhibitor coding region, wherein the miRNA inhibitor hybridizes with the test miRNA. In some embodiments, the first promoter is a RNA Polymerase II promoter. In some embodiments, the second promoter is a RNA Polymerase III promoter. In some embodiments, the nucleic acid vector further comprises a first untranslated region between the first promoter and at least a portion of the protein coding region, wherein the second promoter and the miRNA inhibitor coding region are positioned within the first untranslated region. In some embodiments, the first untranslated region is positioned at the 5' end of the complete protein coding region. In some embodiments, the first untranslated region is positioned within an intron of the protein coding region. In some embodiments, the transgene further comprises a second untranslated region, wherein the at least one binding site of the test miRNA is in the second untranslated region. In some embodiments, the second untranslated region is positioned at the 3' end of the complete protein coding region. In some embodiments, the nucleic acid vector further comprises a pair of inverted terminal repeats that flank the first promoter and the transgene. In some embodiments, the pair of inverted terminal repeats further flank the second promoter and the miRNA inhibitor coding region. In some embodiments, the protein coding region encodes a reporter protein selected from: a fluorescent protein, luciferase, β-galactosidase, secreted alkaline phosphatase, β-glucuronidase, chloramphenicol acetyltransferase (CAT), and β-lactamase.

In some aspects of the invention, a molecule sensing system is provided. In some embodiments, the molecular sensing system comprises a nucleic acid vector for assessing the function of a miRNA inhibitor. In some embodiments, the nucleic acid vector of the molecular sensing system comprises a promoter operably linked with a transgene that is regulated by a test miRNA and a promoter operably linked with a miRNA inhibitor coding region.

According to some aspects of the invention, methods are provided for assessing the effectiveness of a miRNA inhibitor. In some embodiments, the methods comprise (a) transfecting a cell with any of the foregoing nucleic acid vectors, wherein the miRNA inhibitor coding region encodes the miRNA inhibitor; and (b) determining the level of expression of the protein encoded by the protein coding region in the cell, wherein the level of expression of the protein is indicative of the effectiveness of the miRNA inhibitor. In some embodiments, the methods further comprise contacting the cell with the test miRNA. In some embodiments, the cell expresses the test miRNA. In some embodiments, the methods comprise (a) transfecting a first cell with any one of the foregoing nucleic acid vectors, wherein the miRNA inhibitor coding region encodes the miRNA inhibitor; (b) transfecting a second cell with the nucleic acid vector, wherein levels of the test miRNA are lower in the second cell compared with the first cell; and (c) comparing the level of expression of the protein encoded by the protein coding region in the first cell with the level of expression of the protein encoded by the protein coding region in the second cell, wherein the results of the comparison in (c) are indicative of the effectiveness of the miRNA inhibitor. In some embodiments, the methods comprise (a) transfecting a cell with any one of the foregoing nucleic acid vectors, wherein the miRNA inhibitor coding region encodes the miRNA inhibitor; (b) determining a first level of expression of the protein encoded by the protein coding region in the cell; (c) contacting the cell with the test miRNA; (d) determining a second level of expression of the protein encoded by the protein coding region in the cell; and (e) comparing the first level of expression of the protein with the second level of expression, wherein the results of the comparison in (e) are indicative of the effectiveness of the miRNA inhibitor. In some embodiments, the methods comprise (a) transfecting a cell with any one of the foregoing nucleic acid vectors, wherein the miRNA inhibitor coding region encodes the miRNA inhibitor; (b) determining a first level of expression of the protein encoded by the protein coding region in the cell; and (c) comparing the first level of expression of the protein with a control level of expression, wherein the results of the comparison in (c) are indicative of the effectiveness of the miRNA inhibitor.

In some aspects of the invention, kits are provided for assessing the function of a miRNA inhibitor. In some embodiments, the kits comprise a container housing any of the foregoing nucleic acid vectors. In some embodiments, the kits comprise a container housing a component of a molecular sensing system.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

FIG. 2c reports the quantification of these data.

DETAILED DESCRIPTION

Figure 1:
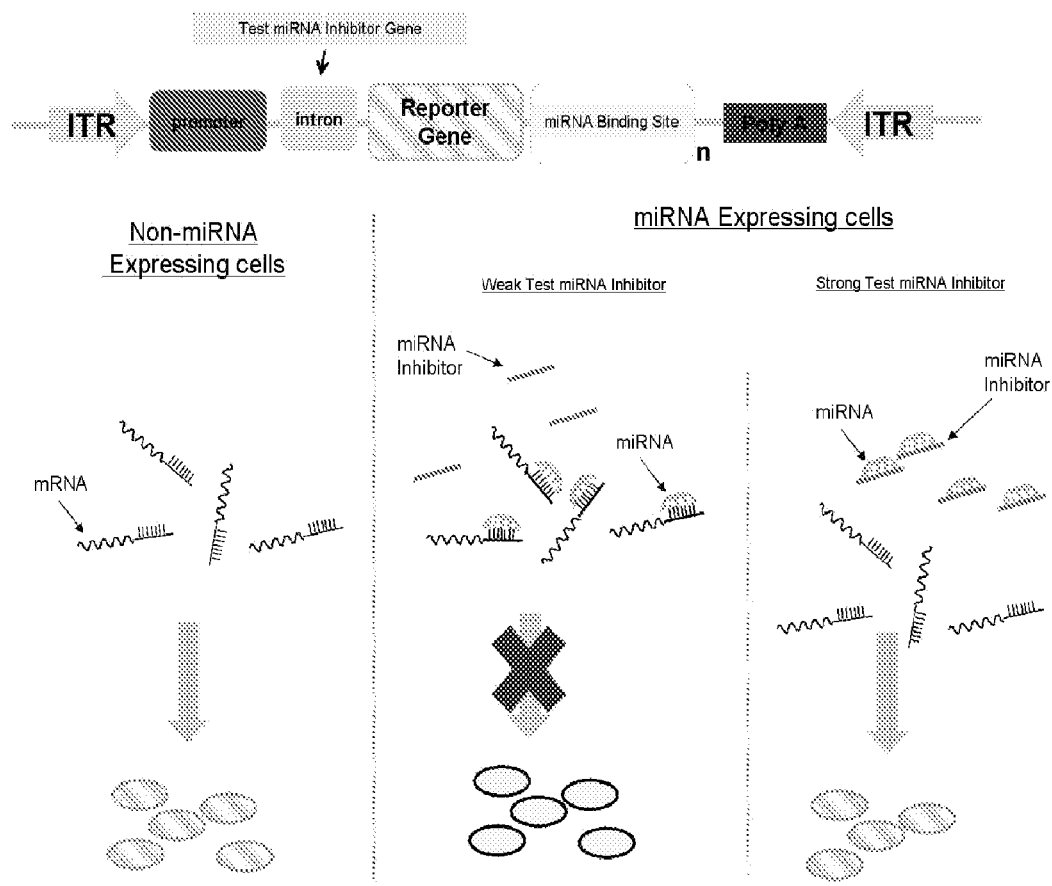
FIG. 1 depicts a molecular sensing system for evaluating miRNA inhibitor function.

Aspects of the invention are based on the discovery of miRNA inhibitors that are useful for treating and studying cholesterol-related disorders. In some aspects of the invention, a nucleic acid encoding a microRNA inhibitor is packaged in a recombinant AAV (rAAV) for gene transfer to a subject. Recombinant AAVs comprising miRNA inhibitor genes of the invention are useful for therapeutic purposes as well as for research purposes. According to some aspects of the invention, methods are provided for treating a cholesterol-related disorder in a subject. In some embodiments, methods of the invention involve administering an effective amount of a rAAV to a subject. A rAAV may harbor at least one transgene that expresses a miRNA inhibitor that inhibits the expression of miR-122 in the subject. An exemplary miRNA inhibitor has a sequence as set forth in SEQ ID NO: 1.

Cholesterol-Related Disorders

As used herein, a "cholesterol-related disorder" is a condition or disease that results in a pathological change in cholesterol levels (e.g., pathologically low or pathologically high) in a subject. A subject may be a mouse, a rat, a rabbit, a dog, a cat, a sheep, a pig, or a non-human primate, for example. A subject may be a human, e.g., a subject having a cholesterol related disorder. In some embodiments, the subject is an animal model of a high cholesterol-related disorder. A cholesterol-related disorder may be associated with changes in levels of total serum cholesterol, serum HDL cholesterol, or serum LDL cholesterol. A cholesterol related disorder may also be associated with alterations in the ratio between serum LDL and HDL (e.g., an LDL/HDL ratio). Examples of normal cholesterol ranges for different species are provided below in Table 1. As is evident from Table 1, normal ranges are species dependent. Cholesterol-related disorder associated with abnormally high levels of cholesterol are referred to herein as "high cholesterol-related disorders." For human subjects a high cholesterol-related disorder may be characterized by total serum cholesterol level greater than 200 mg/dl. For mouse subjects a high cholesterol-related disorder may be characterized by total serum cholesterol level greater than 100 mg/dl. For rat subjects a high cholesterol-related disorder may be characterized by total serum cholesterol level greater than or equal to 70 mg/dl. Other cholesterol levels that are abnormal will be apparent to the skilled artisan.

TABLE 1

Exemplary ranges of normal cholesterol levels.

| | Human | Rat | Mouse |
|---|---|---|---|
| Total cholesterol (mg/dL) | 140~199 | 50~70 | ~100 |
| LDL (mg/dL) | 105~120 | 7~11 | 5~20 |
| HDL (mg/dL) | 30~59 | 29~40 | 50~100 |

Examples of cholesterol-related disorders that may be treated according to aspects of the invention include, but are not limited to, Type I, Type II (a and b), Type III, Type IV, and Type V Hyperlipoproteinemia. Further disorders that may be treated according to aspects of the invention include cholesterol-related disorders associated with diabetes mellitus, metabolic syndrome, kidney disease (nephrotic syndrome), hypothyroidism, Cushing's syndrome, anorexia nervosa, sleep deprivation, Zieve's syndrome, antiretroviral drugs, diet, high body weight, or low physical activity. Other cholesterol-related disorders will be apparent to the skilled artisan.

Certain cholesterol-related disorders that may be treated according to aspects of the invention are disorders of a genetic origin (e.g., inherited, arising from somatic mutations). Familial hypercholesterolemia (FH) (Type II Hyperlipoproteinemia), for example, is a cholesterol-related disorders of genetic origin characterized by high cholesterol levels, specifically very high low-density lipoprotein (LDL) levels, in the blood and early cardiovascular disease. Many subjects with FH have mutations in the LDLR gene that encodes the LDL receptor protein, which normally removes LDL from the circulation, or apolipoprotein B (ApoB), which is the part of LDL that binds with the receptor; mutations in other genes are rare. Subjects who have one abnormal copy (are heterozygous) of the LDLR gene may have premature cardiovascular disease at the age of 30 to 40.

MiRNA Inhibitors

Micro RNAs (miRNAs) appear to play a role in regulating a broad range of cellular processes, and changes in miRNA expression have been implicated in human disease. It is understood that microRNAs have a role in the development and progression of certain cholesterol-related disorders. The most abundant miRNA in the liver, miR-122 regulates cholesterol metabolism by an unknown mechanism and does not directly target LDLR mRNA. Although miR-122 represents a potential therapeutic target for high cholesterol-related disorders, the prospect of therapeutically effective inhibitors of miR-122 has been largely unfulfilled.

As used herein, the term "miRNA Inhibitor" refers to an agent that blocks miRNA expression, processing and/or function. A variety of miRNA Inhibitor have been disclosed in the art. Non-limiting examples of miRNA inhibitors include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex. (See, e.g., Ebert, M. S. Nature Methods, Epub Aug. 12, 2007; Takeshi Haraguchi, et al., Nucleic Acids Research, 2009, Vol. 37, No. 6 e43, the contents of which relating to TuD RNAs are incorporated herein by reference).

Molecular Sensing System for miRNA Inhibitors

A molecular sensing system was designed to quantitatively evaluate the inhibitory function of different miRNA inhibitor designs and to enable discovery of miRNA inhibitors having superior properties compared with miRNA inhibitors of the art (See FIG. 1 for a schematic of a molecular sensing system). Various miRNA inhibitors were developed and tested using this system (See, e.g., Example 1). According to some aspects of the invention a miRNA inhibitor of miR-122 is identified that effectively reduces serum cholesterol levels.

A molecular sensing system of the invention typically includes components for expressing RNA transcripts of a reporter gene (e.g., a protein coding gene, e.g., EGFP, Luciferase), the expression of which is sensitive to a miRNA that binds to the RNA transcript. Typically, the RNA transcript is an mRNA transcript encoding a protein. Thus, reporter gene activity is often assessed by detecting levels of a protein encoded by an mRNA transcript of the transgene. However, the RNA transcript of the reporter gene may itself serve as a reporter of transgene activity. For example, the RNA may be detected using any one of a variety of standard RNA detection strategies, e.g. RT-PCR, and thus, may serve as a reporter for activity of the transgene. Typically, the RNA transcript of the transgene bears one or more miRNA binding sites. Thus, when expressed in a cell, RNA transcripts of a molecular sensing system are typically sensitive to the presence of miRNA molecules of the cell that bind to them at miRNA binding sites. The miRNA binding sites are typically in the 3' end of the transcript. However, a miRNA binding site may be in a coding region or in any untranslated region of the transgene provided that when a miRNA binds to the site in a cell having a functional miRNA gene silencing pathway, or a in vitro system that recapitulates miRNA activity, expression of the transcript is inhibited. The molecule sensing system also typically comprises components for expressing a test miRNA inhibitor. When mRNA transcripts bearing binding sites for a miRNA are expressed in the presence of the miRNA, the miRNA hybridizes to the binding sites and inhibits expression of a reporter protein encoded by the mRNA. However, when a miRNA inhibitor is expressed that blocks function of the miRNA, expression of the reporter protein is not inhibited (or inhibition of expression is attenuated). Thus, molecular sensing systems of the invention enable efficient screening and identification of miRNA inhibitors with effective inhibitory properties based on levels of reporter gene expression.

A molecule sensing system often includes a nucleic acid vector comprising a promoter operably linked with a transgene that is regulated by a miRNA and a promoter operably linked with an miRNA inhibitor coding region. The transgene of the nucleic acid vector typically includes, at a minimum, a protein coding region (e.g., a reporter protein coding region) and at least one binding site of a miRNA. The protein coding region may encode a reporter protein such as, for example, a fluorescent protein, (e.g., GFP, dsRed, etc.) luciferase, β-galactosidase, secreted alkaline phosphatase, β-glucuronidase, chloramphenicol acetyltransferase (CAT), and to β-lactamase. The promoter for the transgene and the promoter for the miRNA inhibitor coding region may be the same promoter or may be different promoters. The promoter for the transgene is typically a RNA Polymerase II promoter. The promoter for the miRNA inhibitor may be a RNA Polymerase II promoter or an RNA Polymerase III promoter (e.g., a U6 promoter).

The skilled artisan will appreciate that the promoter operably linked with the transgene may be positioned anywhere within the nucleic acid vector provided that the transgene is capable of being expressed in an appropriate expression system, e.g., in a cell or an in vitro transcription/translation system. Similarly, the skilled artisan will appreciate that the promoter operably linked with the miRNA inhibitor coding region may be positioned anywhere within the nucleic acid vector provided that the miRNA inhibitor coding region is capable of being expressed in an appropriate expression system, e.g., in a cell or an in vitro transcription/translation system. For example, the second promoter operably linked with a miRNA inhibitor coding region may be positioned upstream of the first promoter operably linked with the transgene (5-prime relative to the first promoter operably linked with the transgene.) The second promoter operably linked with a miRNA inhibitor coding region may be positioned downstream of the first promoter operably linked with the transgene (3-prime relative to the first promoter operably linked with the transgene.) The second promoter operably linked with a miRNA inhibitor coding region may be positioned between the first promoter and the transgene coding region (e.g., within an intron). The second promoter operably linked with a miRNA inhibitor coding region may be positioned within any intron of the transgene. The second promoter operably linked with a miRNA inhibitor coding region may be positioned within a untranslated region upstream of the transgene coding region (e.g., a 5'-UTR) or downstream of the transgene coding region (e.g., a 3'-UTR).

A molecule sensing system may include, for example, a nucleic acid vector comprising a first promoter operably linked with a transgene that is regulated by a test miRNA and a second promoter operably linked with a miRNA inhibitor coding region. The nucleic acid vector may be a recombinant viral genome. For example, the nucleic acid vector may be a recombinant AAV vector. Accordingly, the nucleic acid vector further may include a pair of inverted terminal repeats that flank the promoter operably linked with transgene. The pair of inverted terminal repeats may further flank the promoter operably linked with the miRNA inhibitor coding region.

Methods are provided for assessing the effectiveness of a miRNA inhibitor using a molecular sensing system of the invention. The methods typically involve (a) transfecting a cell with a nucleic acid vector, which comprises a first promoter operably linked with a transgene that comprises a protein coding region and at least one binding site of a miRNA and a second promoter operably linked with a coding region for a miRNA inhibitor that hybridizes with the miRNA, and (b) determining the level of expression of the protein encoded by the protein coding region in the cell. The level of expression of the protein is indicative of the effectiveness of the miRNA inhibitor. For example, when the nucleic acid vector is transfected in a cell that expresses the miRNA, the miRNA will bind to its cognate binding site(s) in the mRNA transcribed from the transgene and inhibit expression of the mRNA. If the miRNA inhibitor is effective, it will block (or decrease) the activity of the miRNA, e.g., by hybridizing with the miRNA, and relieve (or attenuate) repression of expression of the mRNA. Changes in expression of the mRNA are typically observed by assessing levels of the reporter protein encoded by the mRNA. Thus, different miRNA inhibitors can be compared based on reporter protein levels. As will be appreciated by the skilled artisan, the system can be tuned in various ways to identify inhibitors having desired levels of effectiveness. For example, the quality of the miRNA binding site on the transgene mRNA can be designed or selected. High quality binding sites, e.g., binding sites that bind to the test miRNA with high affinity can be designed or selected. Binding sites can be designed de novo or selected from miRNA bindings sites of known genes (e.g., an miR-122 binding site on Cyclin G may be selected). The number of miRNA binding sites in the transgene mRNA can also be altered. For example, multiple binding sites can be used or a single binding site can be used. By adjusting parameters such as the affinity of the miRNA for binding to its miRNA and the number of bindings sites, it becomes possible to increase or decrease the stringency with which miRNA inhibitors are selected. For example, high quality miRNA inhibitors can be selected by using a transgene having multiple high-quality bindings sites for a test miRNA. The molecule sensing system may be used in an in vitro expression system or in cells.

The level of the miRNA is another example of a parameter that can be modulated to increase or decrease the stringency with which miRNA inhibitors are selected. Thus, the methods may further comprise contacting cells with the miRNA or adding miRNA to an in vitro expression system. Multiple experiments may be performed, e.g., in parallel, using different doses of the miRNA to enable an evaluation of the dose dependent inhibition properties of the miRNA inhibitors.

Any of a variety of control values or experiments may be obtained or performed to assess the effectiveness of a test miRNA inhibitor. The methods may comprise (a) transfecting a first cell with a nucleic acid vector of a molecular sensing system, wherein the miRNA inhibitor coding region of the vector encodes the miRNA inhibitor; (b) transfecting a second cell with the nucleic acid vector, wherein levels of the test miRNA are lower in the second cell compared with the first cell; and (c) comparing the level of expression of the protein encoded by the protein coding region in the first cell with the level of expression of the protein encoded by the protein coding region in the second cell, wherein the results of the comparison in (c) are indicative of the effectiveness of the miRNA inhibitor. The methods may comprise (a) transfecting a cell with any one of the foregoing nucleic acid vectors, wherein the miRNA inhibitor coding region encodes the miRNA inhibitor; (b) determining a first level of expression of the protein encoded by the protein coding region in the cell; (c) contacting the cell with the test miRNA; (d) determining a second level of expression of the protein encoded by the protein coding region in the cell; and (e) comparing the first level of expression of the protein with the second level of expression, wherein the results of the comparison in (e) are indicative of the effectiveness of the miRNA inhibitor.

MiRNA Inhibitor Structure

Aspects of the invention are based on the discovery of miRNA inhibitors that target miR-122 and block its function. For example, high quality miRNA inhibitors have been discovered using a molecular sensing system of the invention.

The typical miRNA inhibitor of the invention is a nucleic acid molecule that comprises at least one miRNA binding site, e.g., an miR-122 binding site. The miRNA inhibitors may comprise 1 miRNA binding site, 2 miRNA binding sites, 3 miRNA binding sites, 4 miRNA binding sites, 5 miRNA binding sites, 6 miRNA binding sites, 7 miRNA binding sites, 8 miRNA binding sites, 9 miRNA binding sites, 10 miRNA binding sites, or more miRNA binding sites. As used herein, the term "miRNA binding site," with reference to a miRNA inhibitor, refers to a sequence of nucleotides in a miRNA inhibitor that are sufficiently complementary with a sequence of nucleotides in a miRNA to effect base pairing between the miRNA inhibitor and the miRNA. Typically, a miRNA binding site comprises a sequence of nucleotides that are sufficiently complementary with a sequence of nucleotides in a miRNA to effect base pairing between the miRNA inhibitor and to thereby inhibit binding of the miRNA to a target mRNA.

As used herein the term "complementary" or "complementarity" refers to the ability of a nucleic acid to form hydrogen bond(s) with another RNA sequence by either traditional Watson-Crick or other non-traditional base pairing. In reference to the nucleic molecules of the present invention, the binding free energy for a nucleic acid molecule with its target or complementary sequence is sufficient to allow the relevant function of the nucleic acid to proceed, e.g., miRNA inhibition. Determination of binding free energies for nucleic acid molecules is well known in the art (see, e.g., Turner et al., 1987, CSH Symp. Quant. Biol. LII pp. 123 133; Frier et al., 1986, Proc. Nat. Acad. Sci. USA 83:9373 9377; Turner et al., 1987, J. Am. Chem. Soc. 109:3783-3785). A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. In some embodiments the nucleic acids have 90%, 91%, 92%, 93%, 94%, 95%, 96%, 97%, 98%, 99% or 100% complementarity.

For a miRNA inhibitor having two miRNA binding sites, the first miRNA binding site and the second miRNA binding site may be complementary, e.g., at a sequence of 2 to 10 nucleotides in length. In one example, the first miRNA binding and the second miRNA binding site are complementary at a sequence of 4 nucleotides in length. Each miRNA binding site of a miRNA inhibitor may be any of a variety of lengths. For example, the miRNA binding site of a miRNA inhibitor may be 5 nucleotides to 35 nucleotides, 10 nucleotides to 30 nucleotides, or 15 nucleotides to 25 nucleotides. Typically the length of the miRNA binding site depends on the length and/or structure of the miRNA to which it binds.

Often a miRNA binding site of a miRNA inhibitor of the invention is flanked by one or more stem sequence. As used herein the term "stem sequence" refers to a sequence of a nucleic acid that results in intramolecular base pairing. In some embodiments, stem sequences are not complementary with a target miRNA. Intramolecular base pairing may occur when two stem sequence regions of a miRNA inhibitor, usually palindromic sequences, base-pair to form a double helix, which may end in an unpaired loop. Thus, based pairing may form within a stem sequence or between two stem sequences. A stem sequence may be of a variety of lengths. For example, a stem sequence may be in range 3 nucleotides to 200 nucleotides, 3 nucleotides to 100 nucleotides, 3 nucleotides to 50, 3 nucleotides to 25 nucleotides, 10 nucleotides to 20 nucleotides, 20 nucleotides to 30 nucleotides, 30 nucleotides to 40 nucleotides, 40 nucleotides to 50 nucleotides, or 50 nucleotides to 100 nucleotides. A stem sequence may be up to 5 nucleotides, up to 10 nucleotides, up to 20 nucleotides, up to 50 nucleotides, up to 100 nucleotides, up to 200 nucleotides, or more. Linker sequences may also be included in a miRNA inhibitor. The miRNA inhibitor may comprise a first miRNA binding site and a second miRNA binding site, each binding site flanked by two stem sequences. A first stem sequence may flank the first miRNA binding site at its 5'-end, a second stem sequence may flank the first miRNA binding site at its 3'-end and the second miRNA binding site at its 5'-end, and a third stem sequence may flank the second miRNA binding site at its 3'-end. The skilled artisan will readily envision other configurations of binding sites and flanking stem sequences.

The miRNA binding site of a miRNA inhibitor of the invention may comprise a non-binding, central portion that is not complementary with the target miRNA (e.g., miR-122), flanked by two portions that are complementary with the target miRNA. A non-binding, central portion that is not complementary with the target miRNA need not be perfectly centered within the miRNA binding site. For example, a non-binding central portion may be flanked on either side by portions that are complementary with the target miRNA that are of different lengths. A miRNA inhibitor of the invention may comprise multiple miRNA binding sites that have a non-binding, central portion that is not complementary with the target miRNA. The non-binding, central portion of a miRNA binding site may have any of a variety of lengths. For example, a non-binding, central portion of a miRNA binding site may be in a range of 1 nucleotide to 20 nucleotides, 1 nucleotide to 10 nucleotides, 1 nucleotide to 5 nucleotides. The non-binding, central portion of a miRNA binding site may have a length in a range of 3 to 5 nucleotides. In one example, the non-binding, central portion of a miRNA binding site has a length of 4 nucleotides. The length of the non-binding, central portion will typically depend on the length of the miRNA binding site.

Often the non-binding, central portion of a first miRNA binding site is at least partially complementary with the non-binding, central portion of a second miRNA binding site of the inhibitor. Thus, two binding sites of an inhibitor may base pair (hybridize) with each other. The non-binding, central portion of a first miRNA binding site of an inhibitor may be complementary with the non-binding, central portion of a second miRNA binding site of an inhibitor at, for example, 2 nucleotides to 10 nucleotides, depending on the length of the binding site and the non-binding central portion. The non-binding, central portion of a first miRNA binding site of an inhibitor may be complementary with the non-binding, central portion of a second miRNA binding site at, for example, 2 nucleotides, 3 nucleotides, 4 nucleotides, 5 nucleotides, 10 nucleotides, or more nucleotides, typically depending on the length of the binding site and the non-binding central portion.

Some aspects of this invention provide miRNA inhibitors that target a plurality of miRNAs. In some embodiments, targeting a plurality of miRNAs circumvents the problem of inhibition of an individual miRNA being compensated for by related miRNAs. In some embodiments, the plurality of miRNAs belong to a family of miRNAs, for example, the let-7 family. In some embodiments, the plurality of miRNAs share at least some sequence identity. For example, in some embodiments, the plurality of miRNAs each comprise at least one stretch of 5 or more nucleotides that is identical across all of the plurality of miRNAs. In some embodiments, the plurality of miRNAs each comprise at least one stretch of 5 or more nucleotides that is at least 70%, at least 80%, at least 90%, at least 95%, or at least 98% identical to the consensus sequence of that stretch of nucleotides of the plurality of target miRNAs.

The term "consensus sequence," as used herein, refers to a sequence of nucleotides that reflects the most common nucleotide shared by multiple nucleotide sequences at a specific position. In some embodiments, the multiple nucleotide sequences are related nucleotide sequences, for example, sequences of members of the same miRNA family. In some embodiments, a consensus sequence is obtained by aligning two or more sequences and determining the nucleotide most commonly found or most abundant in the aligned sequences at a particular position. Methods and algorithms for sequence alignment for obtaining consensus sequences from a plurality of sequences are well known to those of skill in the art and the invention is not limited in this respect.

In some embodiments, the miRNA inhibitor targeting a plurality of miRNAs is TuD comprising at least one miRNA binding site complementary to a consensus sequence of the plurality of miRNAs. In some embodiments, the consensus sequence is at least 5, at least 6, at least 7, at least 8, at least 9, at least 10, at least 11, at least 12, at least 13, at least 14, at least 15, at least 16, at least 17, at least 18, at least 19, or at least 20 nucleotides in length. In some embodiments, the miRNA inhibitor comprises a first miRNA binding site and a second miRNA binding site, wherein a first stem sequence flanks the first miRNA binding site at its 5'-end, a second stem sequence flanks the first miRNA binding site at its 3'-end and the second miRNA binding site at its 5'-end, and a third stem sequence flanks the second miRNA binding site at its 3'-end, wherein at least one of the miRNA binding sites comprises a nucleotide sequence complementary to a consensus sequence of the plurality of target miRNAs. In some embodiments, the first and the second miRNA binding sites are complementary to a consensus sequence of the plurality of target miRNAs. In some embodiments, the first and/or the second miRNA binding site is at least 7-%, at least 80%, at least 90%, at least 95%, or at least 98% complementary to a consensus sequence of the plurality of target miRNAs. In some embodiments, the consensus sequence the first miRNA binding site is complementary to is directly adjacent to the consensus sequence the second miRNA binding site is complementary to.

In some embodiments, a miRNA inhibitor is provided that targets a plurality of let-7 family member miRNAs. In some embodiments, the miRNA inhibitor comprises a sequence of at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or 26, contiguous nucleotides of SEQ ID NO: 18. In some embodiments, the miRNA inhibitor comprises or consists of the nucleotide sequence of SEQ ID NO: 18, SEQ ID NO: 20, SEQ ID NO: 22, or SEQ ID NO: 24. In some embodiments, methods are provided that comprise contacting a cell with an miRNA inhibitor. The cell may be in vitro or may be in vivo. Accordingly, in some embodiments, the methods involve adding a miRNA inhibitor to a culture of cells in vitro. In other embodiments, the methods involve administering a miRNA inhibitor to a subject.

Some aspects of this invention provide a method of generating a miRNA inhibitor targeting a plurality of miRNAs, wherein the method comprises obtaining a consensus sequence of the plurality of target miRNAs, and generating a miRNA inhibitor, for example, a miRNA inhibitor described herein (e.g., a TuD), comprising a miRNA binding site able to bind to the consensus sequence, and, thus, targeting the plurality of miRNAs. In some embodiments, the miRNA inhibitor so generated comprises a first miRNA binding site and a second miRNA binding site, wherein a first stem sequence flanks the first miRNA binding site at its 5'-end, a second stem sequence flanks the first miRNA binding site at its 3'-end and the second miRNA binding site at its 5'-end, and a third stem sequence flanks the second miRNA binding site at its 3'-end, wherein the miRNA inhibitor comprises a nucleotide sequence complementary to the consensus sequence of the plurality of target miRNAs. In some embodiments, the method further comprises synthesizing the miRNA inhibitor targeting a plurality of miRNAs.

Recombinant AAVs

It has been discovered that the miRNA inhibitors of the invention when expressed from a recombinant AAV vector achieve long-term miRNA inhibitory effects in a subject. For example, it has been discovered that a miRNA inhibitor against miR-122 delivered using a rAAV to a normal subject (who does not have a cholesterol-related disorder) significantly reduces total serum cholesterol in the subject for a sustained period of time, e.g., up to at least 14 weeks. It has further been discovered that a miRNA inhibitor against miR-122 delivered using a rAAV to a subject having a high cholesterol-related disorder also significantly reduces total serum cholesterol in the subject for a sustained period of time, e.g., up to at least 14 weeks.

AAVs are natural inhabitants in mammals. AAVs isolated from mammals, particularly non-human primates, are useful for creating gene transfer vectors for clinical development and human gene therapy applications. In aspects of the invention, a recombinant AAV9 achieves efficient and stable miR-122 antagonism in normal C57BL/6 mice by expressing an optimized miR-122 inhibitor (also referred to herein as an miR-122 antagonist (Antag)). A single intravenous injection of a rAAV9 comprising a rAAV vector encoding an miR-122 inhibitor (rAAV9-miR-122Antag) produced an significant decrease in the level of mature miR-122 and significant up-regulation of miR-122 target genes. A reduction in total serum cholesterol, HDL, and LDL of up to about 50% was observed in a normal subject who was fed a regular diet.

In some aspects, the invention provides isolated AAVs. As used herein with respect to AAVs, the term "isolated" refers to an AAV that has been isolated from its natural environment (e.g., from a host cell, tissue, or subject) or artificially produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, a rAAV having a capsid appropriate for the tissue being targeted can be selected. Typically, the rAAV has a capsid that has a tropism for (that targets) liver tissue, particularly hepatocytes of liver tissue. For example, the rAAV capsid may be of the AAV9 serotype, which has a sequence as set forth in SEQ ID NO: 3, or a variant thereof. The rAAV has a capsid of the AAV9 serotype variant, Csp-3, which has a sequence as set forth in SEQ ID NO: 4. Examples of AAV9 serotype variants are disclosed in U.S. Provisional Application Ser. No. 61/182,084, filed May 28, 2009, the contents of which relating to AAV capsid sequences are incorporated herein by reference. Still, in some embodiments the AAV serotype is selected from: AAV1, AAV2, AAV3, AAV4, AAV5, AAV6, AAV7, AAV8, and AAVrh.10. In other embodiments the AAV serotype is a variant of an AAV serotype is selected from: AAV1, AAV2, AAV3, AAV4, AAV5, AAV6, AAV7, AAV8, and AAVrh.10.

>gi|46487805|gb|AAS99264.1| capsid protein VP1
[Adeno-associated virus 9]
(SEQ ID NO: 3)
MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

QEPDSSAGIGKSGAQPAKKRLNFGQTGDTESVPDPQPIGEPPAAPSGVGS

LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR

LINNNWGFRPKRLNFKLFNIQVKEVTDNNGVKTIANNLTSTVQVFTDSDYQ

LPYVLGSAHEGCLPPFPADVFMIPQYGYLTLNDGSQAVGRSSFYCLEYFP

SQMLRTGNNFQFSYEFENVPFHSSYAHSQSLDRLMNPLIDQYLYYLSKTI

NGSGQNQQTLKFSVAGPSNMAVQGRNYIPGPSYRQQRVSTTVTQNNNSEF

AWPGASSWALNGRNSLMNPGPAMASHKEGEDRFFPLSGSLIFGKQGTGRD

NVDADKVMITNEEEIKTTNPVATESYGQVATNHQSAQAQAQTGWVQNQGI

LPGMVWQDRDVYLQGPIWAKIPHTDGNFHPSPLMGGFGMKHPPPQILIKN

TPVPADPPTAFNKDKLNSFITQYSTGQVSVEIEWELQKENSKRWNPEIQY

TSNYYKSNNVEFAVNTEGVYSEPRPIGTRYLTRNL

>capsid protein VP1 [Adeno-associated virus] CSp3
(SEQ ID NO: 4)
MAADGYLPDWLEDNLSEGIREWWALKPGAPQPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVEQSP

```
QEPDSSAGIGKSGAQPAKKRLNFGQTGDTESVPDPQPIGEPPAAPSGVGS

LTIASGGGAPVADNNEGADGVGSSSGNWHCDSQWLGDRVITTSTRTWALP

TYNNHLYKRISNSTSGGSSNDNAYFGYSTPWGYFDFNRFHCHFSPRDWQR

LINNNWGFRPKRLNFKLFNIRVKEVTDNNGVKTITNNLTSTVQVFTDSDY

QLPYVLGSAHEGCLPPFPADVFMIPQYGYLTLNDGSQAVGRSSFYCLEYF

PSQMLRTGNNFQFSYEFENVPFHSSYAHSQSLDRLMNPLIDQYLYYLSKT

INGSGQNQQTLKFSVAGPSNMAVQGRNYIPGPSYRQQRVSTTVTRNNNSE

FAWPGASSWALNGRNSLMNPGPAMASHKEGEDRFFPLSGSLIFGKQGTGR

DNVDADKVMITNEEEIKTTNPVATESYGQVATNHQSAQAQAQTGWVQNQG

ILPGMVWQDRDVYLQGPIWAKIPHTDGNFHPSPLMGGFGVKHPPPQILIK

NTPVPADPPTAFNKDKLNSFITQYSTGQVSVEIEWELQKENSKRWNPEIQ

YTSNYYKSNNVEFAVNTEGVYSEPRPIGTRYLTRNL
```

Recombinant AAVs: Production Methods

Methods for obtaining recombinant AAVs having a desired capsid protein are well known in the art. (See, for example, US 2003/0138772, the contents of which are incorporated herein by reference in their entirety). Typically the methods involve culturing a host cell which contains a nucleic acid sequence encoding an AAV capsid protein or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the invention may be delivered to the packaging host cell using any appropriate genetic element (vector). The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present invention include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpes virus (other than herpes simplex virus type-1), and vaccinia virus.

In some aspects, the invention provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells. Transfection may be achieve for example by infecting a cell with a rAAV harboring a rAAV vector.

A "host cell" refers to any cell that harbors, or is capable of harboring, a substance of interest. Often a host cell is a mammalian cell. A host cell may be used as a recipient of an AAV helper construct, an AAV transgene plasmid, e.g., comprising a promoter operably linked with a miRNA inhibitor, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA, miRNA inhibitor) from a transcribed gene.

The foregoing methods for packaging recombinant vectors in desired AAV capsids to produce the rAAVs of the invention are not meant to be limiting and other suitable methods will be apparent to the skilled artisan.

Recombinant AAV Vectors

"Recombinant AAV (rAAV) vectors" of the invention are typically composed of, at a minimum, a transgene, e.g., encoding a miRNA inhibitor or a nucleic acid of a molecular sensing system, and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a miRNA inhibitor. The nucleic acid coding sequence is operatively linked to regulatory components in a manner which permits transgene transcription, translation, and/or expression in a cell of a target tissue. Recombinant AAV based vectors may be developed for targeting the miRNA inhibitors to liver tissue to interfere with miR-122 function and reduced cholesterol levels. Recombinant AAV based vectors may also be developed for targeting a nucleic vector of a molecular sensing system to cell for evaluating or screening miRNA inhibitors in the cell.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not interfere with the ability of the promoter region to direct the transcription of the coding sequences or interfere with the function of the corresponding RNA transcript. Thus, a promoter region would be operably linked to a nucleic acid sequence if the promoter region were capable of effecting transcription of that DNA sequence such that the resulting transcript might become a functional RNA molecule (e.g., a properly folded miRNA inhibitor).

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Often, a miRNA inhibitor is expressed from a polymerase III promoter, such as, for example, a U6 promoter. However, other appropriate promoters, e.g., RNA polymerase II promoters, may be used.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject, such as, for example, a human, mouse, rat, cat, dog, sheep, rabbit, horse, cow, goat, pig, guinea pig, hamster, chicken, turkey, or a non-human primate (e.g., Macaque).

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs.

Delivery of the rAAVs to a mammalian subject may be by intravenous injection. In some embodiments, the mode of administration of rAAVs is by portal vein injection. Administration into the bloodstream may be by injection into a vein, an artery, or any other vascular conduit. In some embodiments, administration of rAAVs into the bloodstream is by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the rAAVs into the vasculature of an isolated limb to potentially enhance transduction into muscle cells or tissue. Routes of administration may be combined, if desired.

Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the invention may comprise a rAAV alone, or in combination with one or more other viruses (e.g., a second rAAV encoding having one or more different transgenes, e.g., one or more different miRNA inhibitors). In some embodiments, a compositions comprise 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a subject having a particular disease or disorder based on the aforementioned factors, as well as other factors that are well known in the art.

An effective amount of a rAAV is an amount sufficient to target infect an animal, target a desired tissue. In some embodiments, an effective amount of a rAAV is an amount sufficient to produce a stable somatic transgenic animal model. The effective amount will depend primarily on factors such as the species, age, weight, health of the subject, and the tissue to be targeted, and may thus vary among animal and tissue. For example, a effective amount of the rAAV is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain preferred embodiments, $10^{12}$ rAAV genome copies is effective to target heart, liver, and pancreas tissues. In certain embodiments, the dosage of rAAV is $10^{10}$, $10^{11}$, $10^{12}$, $10^{13}$, or $10^{14}$ genome copies per kg. In certain $10^{12}$, embodiments, the dosage of rAAV is $10^{10}$, $10^{11}$, $10^{12}$, $10^{13}$, $10^{14}$, or $10^{15}$ genome copies per subject. In some cases, stable transgenic animals are produced by multiple doses of a rAAV.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described; (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trails examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 .ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. In some embodiments, the kit comprises a container(s) housing agents (components) of a molecular sensing system. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, ampule or other container. The kit may have one or more or all of the components required to administer the agents to an animal, such as a syringe, topical application devices, or iv needle tubing and bag, particularly in the case of the kits for producing specific somatic animal models.

EXAMPLES

Example 1 rAAV-Mediated Delivery of microRNA Scavengers Leads to Efficient and Stable Knock-Down of Cognate microRNA, Upregulation of their Natural Target Genes and Phenotypic Changes in Mice The use of rAAV for the delivery of miRNA antagonists (miR-Antags) in adult mice was investigated. Different designs of vector backbone (ss versus sc), promoter (Pol II versus Pol III) and miRNA antagonist (Sponge, Zip, TuD, etc.) were evaluated for efficient somatic inhibition of specific miRNAs. Different designs of miRNA antagonists (inhibitors) were also evaluated, e.g., bulged binding sites, multiple-tandem copy sponges, etc. MiR-122, which has been reported to regulate cholesterol biosynthesis in the liver, and an anti-oncogenic miRNA, Let-7, were used as targets for inhibition. In order to select high function inhibitors, a chemiluminescent miRNA sensor was developed (See FIG. 1). The chemiluminescent miRNA sensor contained a Polymerase II promoter driving expression of a reporter gene in a rAAV vector. The reporter gene had an intron just downstream of the promoter and a series of miRNA binding sites (sponges) upstream of a poly-A tail. The polymerase II promoter and reporter gene were flanked by inverted terminal repeat sequences. A U6 promoter driving expression of the test miRNA inhibitor was present in the intron of the reporter gene. Thus, the miRNA sensor comprises dual miRNA regulators for sequential repression and de-repression of the reporter gene and target validation.

Figure 2:
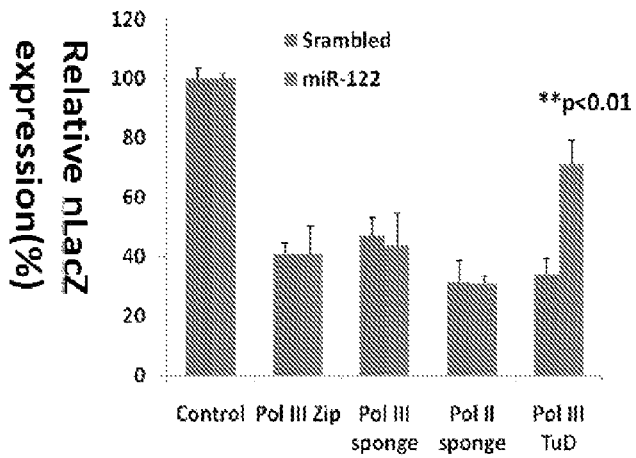
FIG. 2A depicts results from a molecular sensing system assay showing that TuD miR-122 Inhibitor expressed from a polymerase III promoter is highly effective at derepressing reporter gene expression in 293 cells compared with other putative miRNA inhibitors.
FIG. 2B depicts results from a molecular sensing system assay showing that TuD miR-122 Inhibitor expressed from a polymerase III promoter completely restored reporter gene expression in Huh-7 cells from a nucleic acid vector having a single miR122 and substantially derepressed reporter gene expression in Huh-7 cells from a nucleic acid vector having three miR122 binding sites compared with other putative miRNA inhibitors.
FIG. 2C depicts results from an in vivo assay showing that rAAV vector expressing a TuD miR-122 Inhibitor effectively knocks down mature free miR-122 in the liver of mice infected with a rAAV9 containing the vector.
Figure 2:
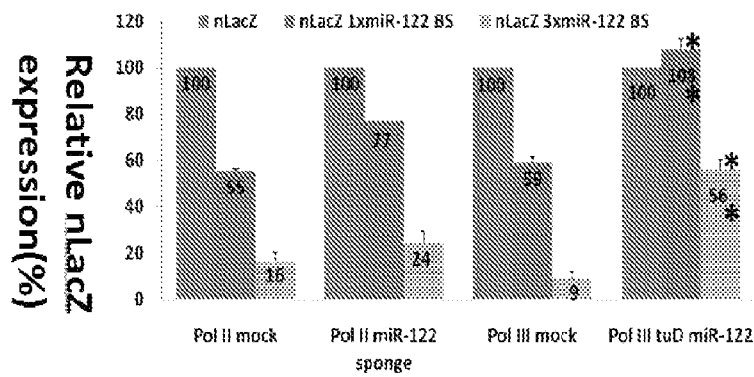
Figure 2:
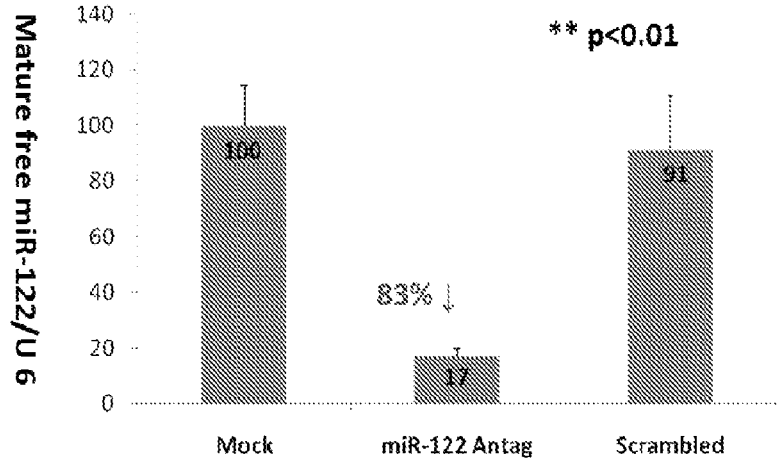

The effectiveness of miR-122 tough decoy RNA designs were assessed. 293 cells were infected with a miRNA sensor encoding β-galactosidase and expressing miR122 tough decoy RNAs. A control miRNA sensor was also transfected that did not express miR122 decoys RNAs. The test and control miRNA sensors each had 3 miR-122 binding sites. The 293 cells were transfected with 0 ng, 50 ng, 100 ng, 200 ng, and 400 ng. LacZ staining was performed using standard techniques to evaluate reporter gene expression. A dose dependent inhibition of reporter gene expression was observed in the control miRNA sensor. However, the test miRNA sensor which expressed miR122 inhibitor exhibited significant attenuation of inhibition of the reporter gene expression at all doses. In contrast, cells infected with a miRNA sensor encoding β-galactosidase and expressing miR122 sponge RNAs did not attenuate reporter gene expression compared with control miRNA sensors. Thus, the TuD miR122 design was superior to the sponge design. Similar experiments where performed in Huh7 cells which expressed steady-state levels of about $1.6 \times 10^4$ miR-122 molecules per cell. In Huh7 cells, the effect of miRNA binding site number was evaluated. The test and control miRNA sensors each had either 1 or 3 miR-122 binding sites. It was found that TuD miR-122 RNA (SEQ ID NO: 1) completely rescued the down-regulation associated with one copy of a miR-122 binding site behind the LacZ reporter gene in Huh-7 cells. Different combinations of promoters (Pol II and Pol III) and miRNA inhibitors were evaluated. Polymerase III driving expression of TuD miR-122 inhibitors has superior results in both 293 and Huh-7 cells (FIGS. 2A and B). A similar miRNA sensor having a firefly luciferase (Fluc) reporter gene was developed and tested in Huh-7 cells. Again, TuD miR-122 RNA efficiently rescued the down-regulation of Fluc mediate by miR-122 binding sites in Huh-7 cells.

Figure 3:
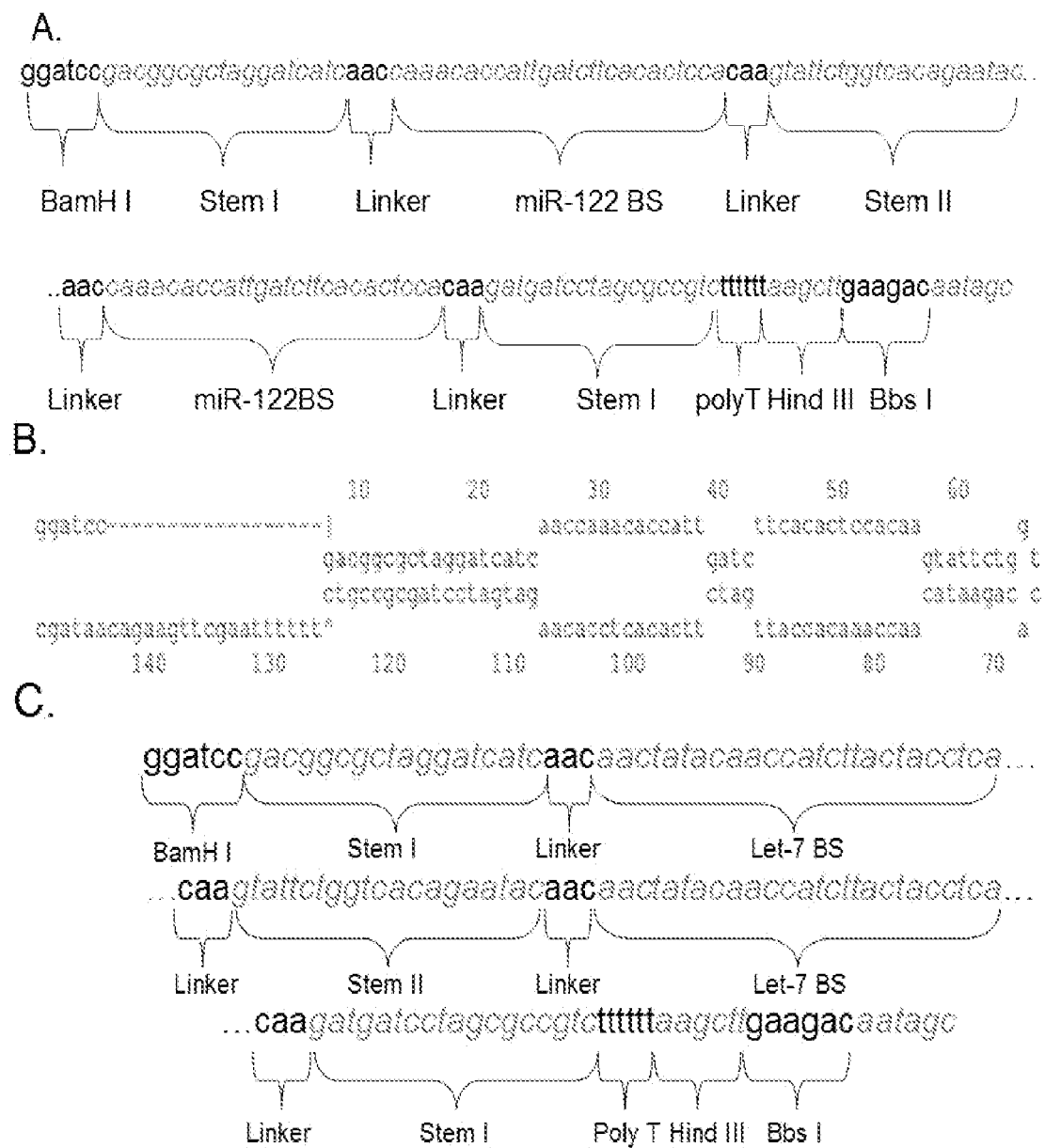
FIG. 3A depicts the sequence and structural features of the TuD miR-122 Inhibitor (SEQ ID NO: 1).
FIG. 3B depicts the predicted secondary structure of the TuD miR-122 Inhibitor (SEQ ID NO: 1). Structure predicted using MFOLD (mobyle.pasteur.fr/cgi-bin/portal.py?form=mfold)
FIG. 3C depicts the sequence and structural features of the TuD Let-7 Inhibitor (SEQ ID NO: 2).

Mice (adult B6) infected with rAAV (Serotype 9) harboring TuD miR-122 inhibitor genes (for up to 7 weeks post infection) exhibited no adverse effects on liver function, as assessed by liver enzymes levels. Effective induction of miR-122 target genes was observed in mice infected with rAAV (Serotype 9) harboring TuD miR-122 inhibitor genes after 1 month post infection, compared with control mice which were infected with rAAV9 harboring scrambled inhibitors. The target genes evaluated include Aldolase A, Cyclin G1, Tmed3 and Hfe2. MiR-122 inhibitors delivered by rAAV9 had no effect on these target genes in the mouse heart, the cells of which do not express miR122. A single IV injection of rAAVmiR-122-Antag to C57BL/6 mice produced an 80% decrease in the level of mature miR-122 (FIG. 2C) and a 3-fold increase in the mRNA levels of miR-122 target genes. Inhibition of miR-122 reduced total serum cholesterol, HDL, and LDL by 50% in mice fed a regular diet. The sequence and secondary structure of the TuD miR-122 inhibitor is shown in FIGS. 3A and 3B, respectively.

Similar experiments were performed to evaluate miRNA inhibitors of Let-7. TuD Let-7 inhibitors were identified that can de-repress luciferase expression mediated by up to 7 copies of Let-7 sponge sequences (Let-7 binding sites). A 2-fold increase in the expression of Dicer mRNA, a Let-7 target, was also observed. Similarly, TuD Let-7, but not Let-7 sponges, induced Dicer protein levels in HeLa cells. Induction of Dicer gene expression was also observed in mice liver and heart infected with rAAV (Serotype 9) harboring TuD Let-7 inhibitor genes (for up to 7 weeks post infection) with no adverse effects on liver function observed. Administration of rAAV-Let-7-Antag increased by 2-fold the mRNA levels of Dicer, the enzyme that produces miRNAs from pre-miRNAs and which is normally repressed by Let-7. The results of this study indicate that rAAV-miR-Antags mediate efficient and stable somatic inhibition of miRNAs and will provide both an efficient tool to study miRNA function as well as a potential therapeutic for dyslipidemia, in the case of miR122, and other diseases caused by miRNA deregulation.

Figure 4:
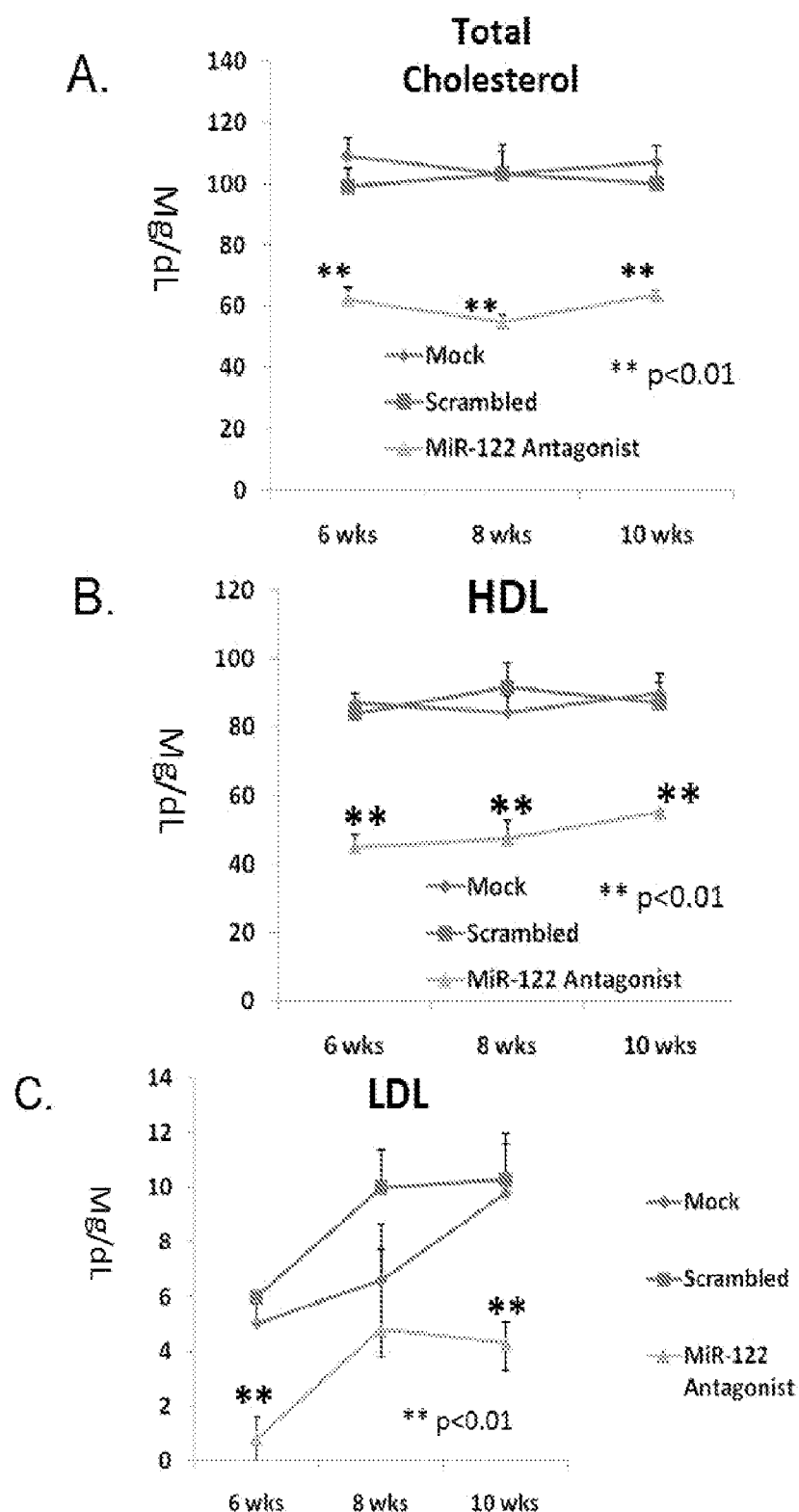
FIG. 4A depicts results from an in vivo assay showing that rAAV vector expressing a TuD miR-122 Inhibitor effectively reduced total serum cholesterol levels for up to 10 weeks in mice infected with a rAAV9 containing the vector and fed a normal chow diet.
FIG. 4B depicts results from an in vivo assay showing that rAAV vector expressing a TuD miR-122 Inhibitor effectively reduced serum HDL levels for up to 10 weeks in mice infected with a rAAV9 containing the vector and fed a normal chow diet.
FIG. 4C depicts results from an in vivo assay showing that rAAV vector expressing a TuD miR-122 Inhibitor effectively reduced serum LDL levels for up to 2 weeks in mice infected with a rAAV9 containing the vector and fed a normal chow diet.
Figure 5:
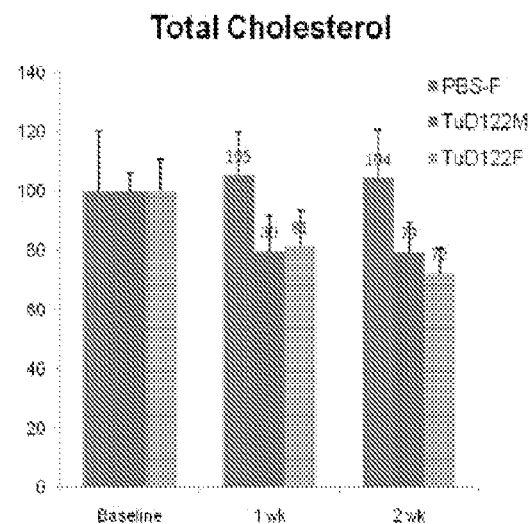
FIG. 5A depicts results from an in vivo assay showing that rAAV vector expressing a TuD miR-122 Inhibitor effectively reduced total serum cholesterol levels for up to 10 weeks in LDLR$^{-/-}$ Apobec1$^{-/-}$ mice (a model Familial hypercholesterolemia) infected with a rAAV9 containing the vector.
FIG. 5B depicts results from an in vivo assay showing that rAAV vector expressing a TuD miR-122 Inhibitor effectively reduced serum HDL levels for up to 2 weeks in LDLR$^{-/-}$ Apobec1$^{-/-}$ mice infected with a rAAV9 containing the vector.
FIG. 5C depicts results from an in vivo assay showing that rAAV vector expressing a TuD miR-122 Inhibitor effectively reduced serum LDL levels for up to 2 weeks in LDLR$^{-/-}$ Apobec1$^{-/-}$ mice for infected with a rAAV9 containing the vector.
Figure 5:
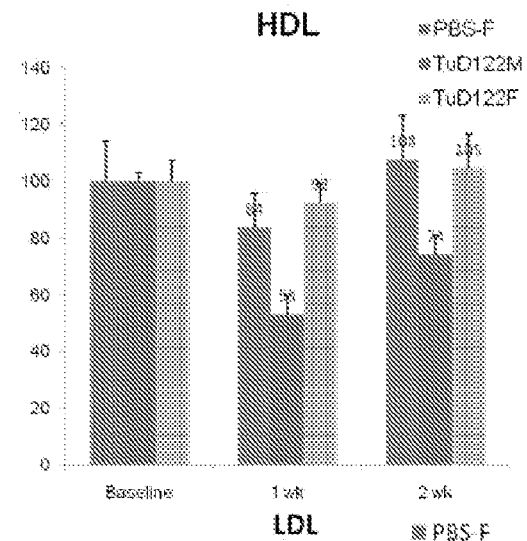
Figure 5:
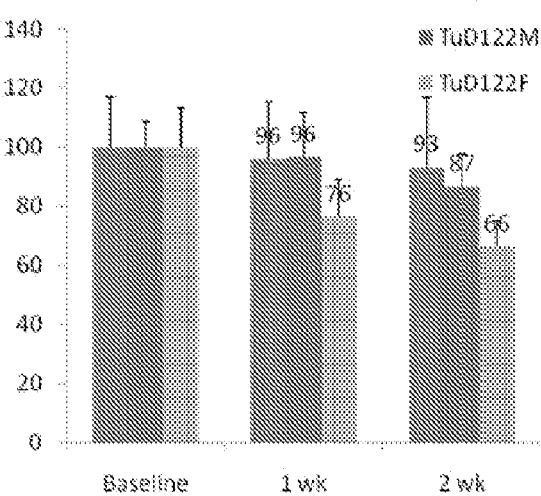

Example 2 rAAV-Mediated Therapeutic Silencing of miR-122 Leads to Rapid and Significant Reduction of LDL in DLDR$^{-/-}$/Apobec 1$^{-/-}$ Mice MicroRNA (miRNA) regulation was evaluated as an alternative to FH gene therapy. miRNAs play critical roles in regulating most cellular processes. The most abundant miRNA in the liver, miR-122 regulates cholesterol metabolism by an unknown mechanism(s) and does not directly target LDLR mRNA. Recombinant AAV9 was examined for efficient and stable miR-122 antagonism in normal C57BL/6 mice by expressing an optimized miRNA-122 antagonist (Antag). A single intravenous injection of rAAV9-miR-122Antag (SEQ ID NO: 1) produced an 80% decrease in the level of mature miR-122 and 3-fold up-regulation of four miR-122 target genes as well as a 50% reduction in total serum cholesterol, HDL, and LDL in male mice fed a regular diet (FIGS. 4A, 4B, and 4C). This inhibition was observed for up to 14 weeks post infection with no significant impact on liver function as assessed by Alanine aminotransferase (ALT) and aspartate aminotransferase (AST) gene expression levels. ALT and AST are enzymes located in liver cells that leak out into the general circulation when liver cells are injured. To assess the therapeutic potential of miR-122 inhibition, the same vector was administered to adult male and female LDLR−/−/Apobec 1A−/− mice, the most comparable mouse model of human FH with the normal chow diet (Powell-Braxton L, et al., Nature Medicine, Volume 4, Number 8, August 1998.) One week after dosing, a 20% decrease in total serum cholesterol was observed in both males and females. Interestingly, the decreases in males were exclusively in the HDL fraction, whereas the declines in females were exclusively in LDL. By the second week, total cholesterol and LDL in the treated females had declined about 30% but HDL levels remained unchanged. (See, FIGS. 5A, 5B, and 5C.) The reduction of total cholesterol in males remained at 20%, reflecting a 50% increase in HDL and a 13% drop in LDL as compared to the mice in week 1. The observed sex-specific differences in miR-122 inhibition may reflect the previously reported lower efficiency of rAAV-mediated liver transduction in female mice, suggesting that doses may be optimized for rAAV-mediated therapeutic inhibition of miR-122 for the treatment of FH (Davidoff A M, et al., Blood. 2003; 102:480-488). The results of this study indicate that rAAV can achieve efficient and stable somatic miRNA inhibition providing basis for a therapy for dyslipidemia and other diseases caused by miRNA deregulation.

Example 3

AAV Vector-Mediated In Vivo miRNA Antagonism for Treating Hyperlipidemia

Genetic disruption of a miRNA gene represents a powerful strategy to study miRNA function, but many miRNA genes share the same seed sequence—the 6-8 nt miRNA region that defines its target repertoire—and therefore one member of a miRNA family can compensate for loss of another. Creation of an animal model in which all members of a miRNA family are deleted is daunting. Moreover, humans and mice share more than 276 miRNAs, requiring hundreds of conditional knockout strains to assess the function and contribution to disease of each conserved miRNA in adult mice. Chemically modified anti-miRNA oligonucleotides (AMO) complementary to mature miRNAs are widely available tools for miRNA inhibition in vitro and in vivo[3-9]. Effective AMOs typically employ expensive or proprietary chemical modifications such as 2'-O-methyl, 2'-O-methoxyethyl, or 2',4'-methylene (locked nucleic acid; LNA), and current chemistries and formulations do not permit safe and effective delivery of AMOs to many tissues or organs. Additionally, miRNA inhibition with AMOs requires repeated administrations to suppress expression of the cognate miRNA[3,7-11].

As an alternative to AMOs, plasmid DNA vectors that express miRNA "sponges"-multiple, tandem miRNA binding sites designed to competitively inhibit miRNA function and expressed from an RNA polymerase II promoter—have been used to study miRNA function in cultured cells[12] and in vivo in flies[13]. Depletion of miR-223 in hematopoietic cells using a sponge-expressing lentiviral vector to stably modify hematopoietic stem cells ex vivo, followed by bone marrow reconstitution in mice, produced a phenotype similar to that observed in a genetic miRNA knockout[14]. However, the risk of insertional mutagenesis and the requirement for ex vivo manipulation may limit the use of the lentiviral vector-based miRNA inhibition for functional genomics studies and therapeutic applications. More recently, compact, RNA polymerase III-driven miRNA decoys have been reported, including "Tough Decoy" (TuD) RNAs and miRZips, both of which enable stable and permanent inhibition of miRNA in cultured cells and in vivo[16]. Nevertheless, a method to stably and efficiently antagonize miRNAs for studying miRNA-target interactions in adult mammals remains to be developed.

The 4.7 kb single-stranded DNA parvovirus Adeno-associated virus[17] (AAV) is a widespread, nonpathogenic resident in primates, including humans[18,19]. In the past decade, new recombinant AAV (rAAV) vectors have been created from natural AAV serotypes, providing efficient gene transfer vehicles that target diverse tissues in mice and non-human primates[20-23].

Here, the use of rAAV vectors in mice to inhibit miR-122, a miRNA highly abundant in liver[24], and let-7, a miRNA with functions in cancer and development[25] is reported. Different promoters (RNA polymerase II versus RNA polymerase III) and designs of miRNA antagonists (sponge, TuD, and miRZip) were evaluated in cultured cells, and RNA polymerase III-driven TuD was identified as the most potent miRNA antagonist. rAAV9 vectors were engineered expressing anti-miR-122 and anti-let-7 TuD RNAs and were used to achieve efficient, sustained and target-specific miR-122 or let-7 inhibition in vivo. Each miRNA inhibitor increased the expression of the corresponding miRNA target genes in adult mice. High throughput sequencing of liver miRNAs from the treated mice confirmed that the targeted miRNA, but no other miRNAs, were depleted. Moreover, miRNA depletion in vivo was accompanied by the 3' addition of non-templated nucleotides as well as 3'-to-5' shortening of the miRNA, a degradation pathway previously observed in vivo in *Drosophila melanogaster* and in vitro in transformed, cultured human cells[33]. Importantly, sustained phenotypic changes were observed in the serum cholesterol profiles of both wild-type C57BL/6 and low density lipoprotein (LDL) receptor-deficient mice treated with rAAV9-expressing the anti-miR-122, but not the anti-let-7, TuD RNA. The data provided herein suggest that rAAV-expressing TuD RNAs could enable stable therapy for hypercholesterolemia and other disorders caused by miRNA expression.

Evaluation of Transcribed miRNA Antagonists in Cultured Cells

Figure 6:
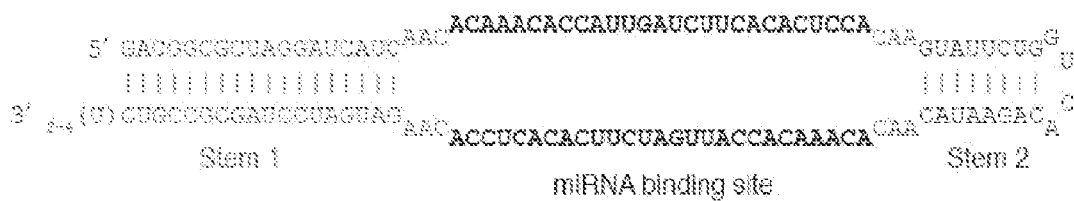
FIG. 6 Structure of a Tough Decoy miR-122 (TuD) RNA (SEQ ID NO: 5). TuD RNAs contain two single-stranded miRNA binding sites flanked by double-stranded stems intended to enhance stability and promote nuclear export.
Figure 7:
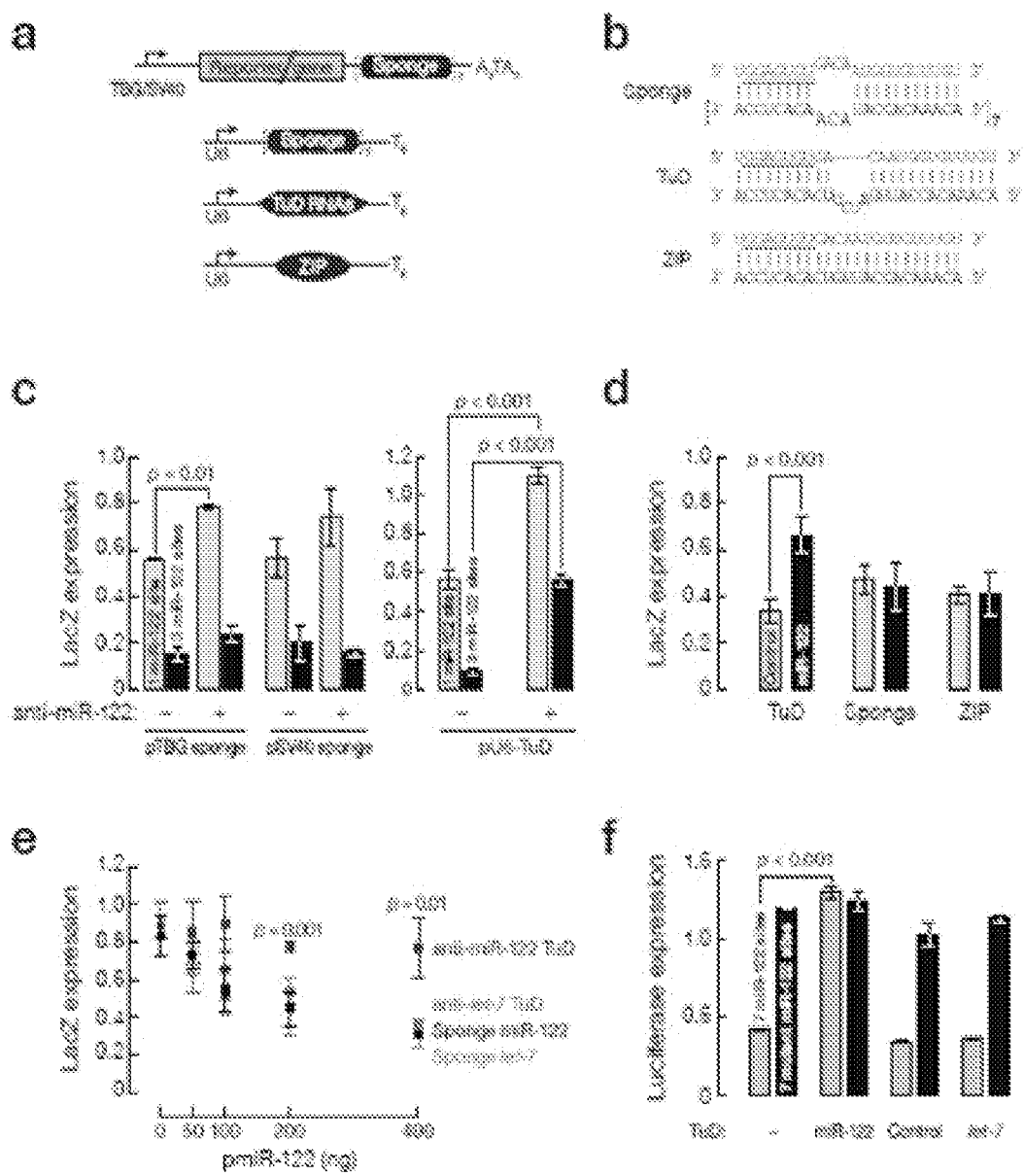
FIG. 7 Comparison of miR-122 inhibitor strategies in cultured cells. (a) miRNA inhibitor constructs. (b) Pairing of antagonists to miR-122. Upper sequence in all three panels: miR122 fragment (SEQ ID NO: 6). Sponge: SEQ ID NO: 7. TuD: SEQ ID NO: 8. ZIP: SEQ ID NO: 9. (c) Plasmid harboring nLacZ reporter gene with one or three sites complementary to miR-122 was co-transfected with pTBG Fluc and either control plasmid, anti-miR-122 sponge plasmid or U6-driven anti-miR-122 TuD plasmid. The cells were stained for LacZ expression 48 h after transfection, and blue cells were counted. Data are reported relative to a control reporter plasmid lacking miR-122-binding sites. (d) Reporter plasmid expressing nLacZ mRNA containing 3 miR-122-binding sites was co-transfected into HuH-7 cells with a U6-driven sponge-, miRZip- or TuD-expressing plasmid. The empty plasmid served as the control. (e) HEK 293 cells were transfected with a nLacZ reporter plasmid containing three fully complementary miR-122-binding sites, together with the constructs expressing anti-let-7 or anti-miR-122 TuD transcribed from a U6 promoter or anti-miR122 sponge or anti-let-7 sponge transcribed from an SV40 promoter, as well as different amounts of a plasmid producing pri-miR-122 RNA. Forty-eight hours later, the cells the percentages of nLacZ positive cells, relative to the control (nLacZ without miR-122binding sites), were determined (c, d, and e). (f) HuH-7 cells were transfected with reporter plasmid expressing control luciferase, luciferase bearing seven miR-122 binding sites, or seven mutant sites, as well as control plasmid or plasmid expressing anti-miR-122-, anti-let-7 or scrambled TuD RNA. Twenty-four hours later, crude cell lysates were prepared and luciferase activity assayed. The data are presented as mean±standard deviation for firefly luciferase activity normalized to Renilla luciferase activity.

To test different transcribed miRNA antagonists, a highly abundant miRNA, miR-122, which regulates cholesterol biosynthesis in the liver, and an anti-oncogenic miRNA, let-7, were chosen as targets for inhibition. A series of miR-122 and let-7 antagonists were designed including miRNA sponges, TuD RNAs (FIG. 6) and miRZips[12,15] (www.systembio.com/microrna-research/microrna-knockdown/mirzip/) (Table 2). miRNA sponges were expressed using the RNA polymerase II simian vacuolating virus (SV40) promoter, or the liver-specific, human thyroid hormone-binding globulin (TBG) promoter, or, alternatively, the RNA polymerase III U6 promoter; the U6 promoter was used to drive TuD and miRZip expression (FIGS. 7a and b).

TABLE 2

| Oligonucleotide | Sequence (5' to 3') |
| --- | --- |
| anti-miR-122 TuD | GGATCCGACGGCGCTAGGATCATCAACCAAACA CCATTGATCTTCACACTCCACAAGTATTCTGGT CACAGAATACAACCAAACACCATTGATCTTCAC ACTCCACAAGATGATCCTAGCGCCGTCTTTTTT GAATTC (SEQ ID NO: 19) |
| anti-let-7 TuD | GGATCCGACGGCGCTAGGATCATCAACAACTAT ACAACCATCTTACTACCTCACAAGTATTCTGGT CACAGAATACAACAACTATACAACCATCTTACT ACCTCACAAGATGATCCTAGCGCCGTCTTTTTT GAATTC (SEQ ID NO: 20) |
| miR-122 miRZip | GGATCCTGGTCAGTGACAATGTTTGCTTCCTGT CAGACAAACACCATTGTCACACTCCATTTTTAA GCTTGAAGACAATAGC (SEQ ID NO: 21) |
| anti-let-7 miRZip | GGATCCTCTCGTAGTAGGTTGTATAGTTCTTCC TGTCAGAAACTATACAACCTACTACCTCATTTT TAAGCTTGAAGACAATAGC (SEQ ID NO: 22) |
| anti-miR-122 sponge | TCTAGACAAACACCATACAACACTCCACAAACA CCATACAACACTCCACAAACACCATACAACACT CCACAAACACCATACAACACTCCACAAACACCA TACAACACTCCACAAACACCATACAACACTCCA CAAACACCATACAACACTCCAGGGCCC (SEQ ID NO: 23) |
| anti-let-7 sponge | TCTAGAAACTATACAAAACCTACCTCAAACCAC ACAAAACCTACCTCAAACCATACAAAACCTACC TCAAACTATGCAAAACCTACCTCTAACTATACA AAACCTACCTCAAACTGTACAAAACCTACCTCA AACCATACAAAACCTACCTCAGCCCTAGA (SEQ ID NO: 24) |
| Mutant anti-miR-122 sponge | TCTAGACAAACACCATACAACAAGAAACAAACA CCATACAACAAGAAACAAACACCATACAACAAG AAACAAACACCATACAACAAGAAACAAACACCA TACAACAAGAAACAAACACCATACAACAAGAAA CAAACACCATACAACAAGAAAGGGCCC (SEQ ID NO: 25) |
| Mutant anti-let-7 sponge | TCTAGAAACTATACAAAACCTAAAGAAAACCAC ACAAAACCTAAAGAAAACCATACAAAACCTAAA GAAAACTATGCAAAACCTAAAGATAACTATACA AAACCTAAAGAAAACTGTACAAAACCTAAAGAA AACCATACAAAACCTAAAGAAGGGCCC (SEQ ID NO: 26) |
| (miR-122)1 sense | pCGAAACAAACACCATTGTCACACTCCATT (SEQ ID NO: 27) |
| (miR-122)1 antisense | pCGAATGGAGTGTGACAATGGTGTTTGTTT (SEQ ID NO: 28) |
| (miR-122)3 sense | pCGAAACAAACACCATTGTCACACTCCAACAAA CACCATTGTCACACTCCAA CAAACACCATTGT CACACTCCATT (SEQ ID NO: 29) |
| (miR-122)3 anti-sense | pCGAATGGAGTGTGACAATGGTGTTTGTTGGAG TGTGACAATGGTGTTTGTT GGAGTGTGACAAT GGTGTTTGTTT (SEQ ID NO: 30) |
| XbaI-ApaI linker F | CTAGATTCCGAGATATCGGTAATGGGCC (SEQ ID NO: 31) |
| XbaI-ApaI linker R | GGCCCATTACCGATATCTCGGAATCTAG (SEQ ID NO: 32) |
| pri-miR-122 F | ATCGGGCCCGACTGCAGTTTCAGCGTTTG (SEQ ID NO: 33) |
| pri-miR-122 R | CGCGGGCCCGACTTTACATTACACACAAT (SEQ ID NO: 34) |
| Nras F | TGGACACAGCTGGACAAGAG (SEQ ID NO: 35) |
| Nras R | CTGTCCTTGTTGGCAAGTCA (SEQ ID NO: 36) |
| Kras F | CAAGAGCGCCTTGACGATACA (SEQ ID NO: 37) |
| Kras R | CCAAGAGACAGGTTTCTCCATC (SEQ ID NO: 38) |
| Hras1 F | CGTGAGATTCGGCAGCATAAA (SEQ ID NO: 39) |
| Hras1 R | GACAGCACACATTTGCAGCTC (SEQ ID NO: 40) |
| Mm-Dicer F | GCAGGCTTTTTACACACGCCT (SEQ ID NO: 41) |
| Mm-Dicer R | GGGTCTTCATAAAGGTGCTT (SEQ ID NO: 42) |
| c-MYC F | CAACGTCTTGGAACGTCAGA (SEQ ID NO: 43) |
| c-MYC R | TCGTCTGCTTGAATGGACAG (SEQ ID NO: 44) |

TABLE 2-continued

| Oligonucleotide | Sequence (5' to 3') |
| --- | --- |
| Hfe2 F | GGGGACCTTGCTTTCCACTC (SEQ ID NO: 45) |
| Hfe2 R | GCCTCATAGTCACAGGGATCT (SEQ ID NO: 46) |
| Tmed3 F | AGCAGGGCGTGAAGTTCTC (SEQ ID NO: 47) |
| Tmed3 R | TTGTACGTGAAGCTGTCATACTG (SEQ ID NO: 48) |
| Aldolase A F | TGGGAAGAAGGAGAACCTGA (SEQ ID NO: 49) |
| Aldolase A R | AGTGTTGATGGAGCAGCCTT (SEQ ID NO: 50) |
| CAT-1 F | TACCAGTGGCCGTGTTTGTA (SEQ ID NO: 51) |
| CAT-1 R | GCTGTTGCCAAGCTTCTACC (SEQ ID NO: 52) |
| Cyclin G1 F | AATGGCCTCAGAATGACTGC (SEQ ID NO: 53) |
| Cyclin G1 R | AGTCGCTTTCACAGCCAAAT (SEQ ID NO: 54) |
| Mm-Actin F | ATGCCAACACAGTGCTGTCTGG (SEQ ID NO: 55) |
| Mm-Actin R | TGCTTGCTGATCCACATCTGCT (SEQ ID NO: 56) |
| miR-122 probe | TGGAGTGTGACAATGGTGTTTG (SEQ ID NO: 57) |
| Let-7 probe | AACTATACAACCTACTACCTCA (SEQ ID NO: 58) |
| miR-26a probe | AGCCTATCCTGGATTACTTGAA (SEQ ID NO: 59) |
| miR-22 Probe | ACAGTTCTTCAACTGGCAGCTT (SEQ ID NO: 60) |
| U6 probe | CTCTGTATCGTTCCAATTTTAGTATA (SEQ ID NO: 61) |
| IDT miRNA cloning linker-1 | AppCTGTAGGCACCATCAAT/ddC/ (SEQ ID NO: 62) |
| 5' Illumina RNA Adapter | GUUCAGAGUUCUACAGUCCGACGAUC (SEQ ID NO: 63) |
| Small RNA RT primer | ATTGATGGTGCCTACAG (SEQ ID NO: 64) |
| Small RNA PCR Primer 1 | CAAGCAGAAGACGGCATACGAATTGATGGTGCC TACAG (SEQ ID NO: 65) |
| Small RNA PCR Primer2 | AATGATACGGCGACCACCGACAGGTTCAGAGTT CTACAGTCCGA (SEQ ID NO: 66) |

To evaluate the efficiency of each miRNA antagonist, the ability of the expression constructs to de-repress a nuclear-targeted E. coli β-galactosidase (nLacZ) reporter mRNA containing 1 or 3 copies of fully complementary miR-122-binding sites in the 3' untranslated region (UTR) was tested. The nLacZ reporter plasmid was co-transfected with the various miR-122 inhibitor constructs or a control plasmid into HuH-7 cells[27], a human hepatoma cell line expressing ~16,000 miR-122 molecules per cell[27]. As expected, reporter expression was reduced ~50% when one miR-122-binding site was present in the nLacZ 3' UTR and >80% when three sites were present (FIG. 7c). Among the RNA polymerase II-driven anti-miR-122 sponges, only the TBG promoter, a strong liver-specific promoter, detectably increased expression of nLacZ bearing a single miR-122binding site, indicating that the sponge partially inhibited miR-122. However, nLacZ expression was not significantly increased by this sponge when the reporter contained three miR-122-binding sites (FIG. 7c), suggesting that the change in miR-122 activity or concentration was too small to overcome the greater repression conferred by three miRNA target sites.

In contrast, both the one- and three-site reporters were de-repressed by the RNA polymerase III-driven anti-miR-122 TuD RNA. For the one-site reporter, the TuD restored nLacZ expression to that observed when no miR-122 target sites were present in the reporter (FIG. 7c). The greater efficacy of the TuD RNA might reflect the higher level of transcription possible with RNA polymerase III compared to RNA polymerase II, greater miRNA inhibition by the TuD design, or both. To distinguish among these possibilities, the ability of three different U6-driven miR-122 antagonist constructs—sponge, TuD, and miRZip—to de-repress the nLacZ reporter containing three miR-122-binding sites was compared. Again, only the TuD significantly (p-value ≤0.001) derepressed nLacZ repression by miR-122 in HuH-7 cells (FIG. 7d). The anti-miR-122 TuD expression construct was similarly effective in human embryonic kidney (HEK) 293 cells. Because HEK 293 cells express little miR-122, pri-miR-122 was expressed from a plasmid, which was co-transfected along with the nLacZ reporter with or without three miR-122-binding sites and the TuD-expressing plasmid. nLacZ expression was scored 48 h later. The anti-miR-122 TuD, but not an anti-let-7 TuD or an anti-miR-122 or anti-let-7 sponge, significantly derepressed reporter expression in the presence of the miR-122 expression plasmid (FIG. 7e).

miRNAs that are extensively complementary to their targets direct Argonaute2 protein to cleave the mRNA, whereas less extensive complementarity generally decreases mRNA stability. To test if the TuD RNA can also inhibit repression directed by a miRNA with imperfect complementarity to its target, a firefly luciferase (Fluc) reporter mRNA was designed with seven copies of a bulged miR-122-binding site in its 3' UTR; Fluc with seven7 mutant sites served as a control. The miR-122-responsive Fluc reporter, anti-miR-122, anti-let-7 or control TuD plasmid, and, as an internal control, a Renilla reniformis luciferase (Rluc) expression plasmid, were introduced into HuH-7 cells by transfection. The anti-miR-122 TuD, but not the control or anti-let-7 TuDs, fully de-repressed Fluc expression (FIG. 7f). it is concluded that TuD RNAs are potent and specific miRNA inhibitors.

Figure 8:
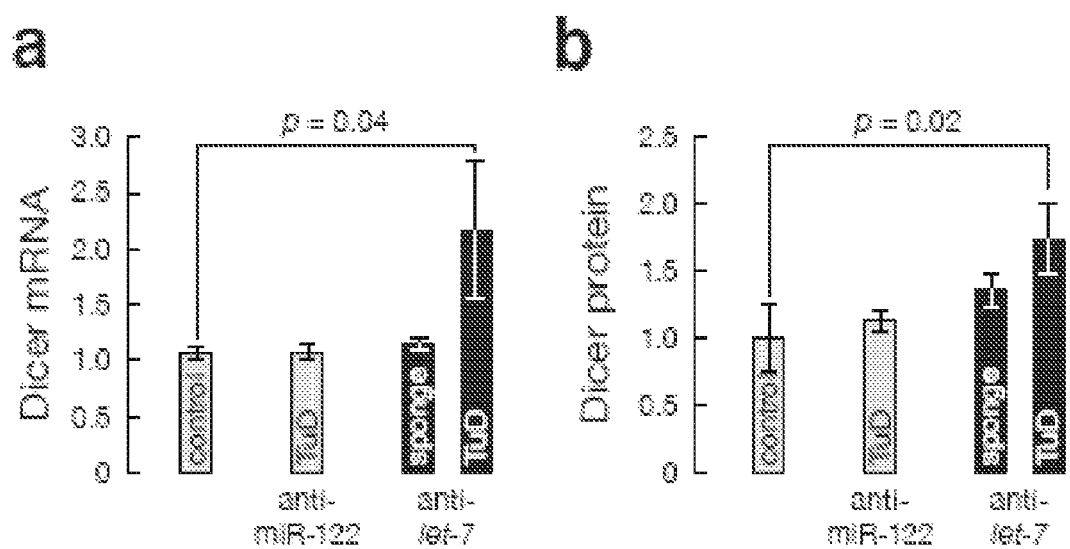
FIG. 8 Evaluation of let-7 antagonist constructs in HeLa cells. (a,b) Total RNA and protein were prepared from HeLa cells transfected with the constructs expressing either anti-miR-122 or anti-let-7 TuD, anti-let-7 sponge or control plasmid. The relative levels of Dicer mRNA was measured by qRT-PCR (a) and of Dicer protein by Western blotting (b). The figure reports mean±standard deviation.
Figure 9:
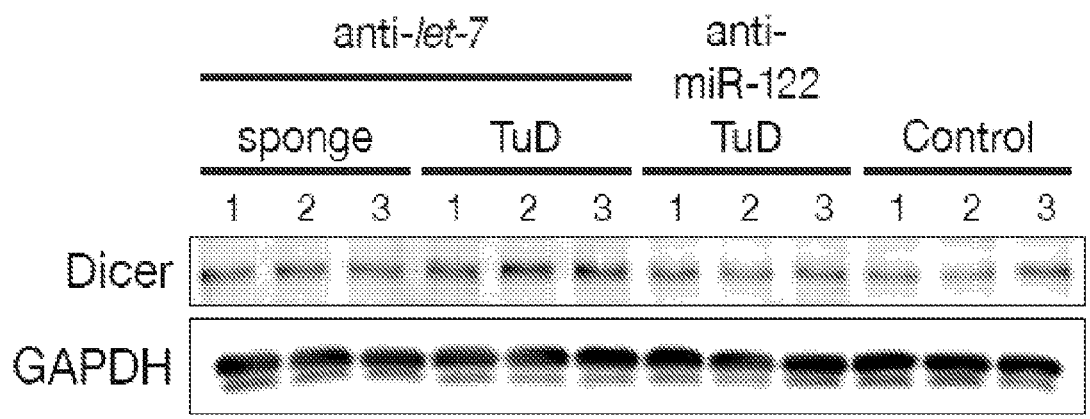
FIG. 9 Western blot analysis of HeLa cells transfected with the constructs expressing either anti-miR-122 or anti-let-7 TuD, anti-let-7 sponge or plasmid control. Three biological replicates are shown.

Finally, the anti-let-7 TuD increased expression of both the Dicer mRNA and protein; dicer is an endogenous let-7 target[28,29] (FIG. 8a, 8b, and FIG. 9). Together, the in vitro data suggest that the TuD RNA transcribed from a U6 promoter was the most potent of the miRNA antagonists surveyed.

Real-Time Monitoring of Specific Endogenous miRNA Activities in Live Animals

To test the ability of TuD RNAs to inhibit miRNA function in vivo, a series of rAAV vector genomes expressing a miRNA-responsive Gaussia luciferase (Gluc)[30] mRNA was constructed (FIG. 10a). Gluc is a secreted protein, enabling detection of the reporter in the blood or urine of live animals. Seven bulged miR-122 or let-7 target sites were inserted into the 3' UTR of the Gluc mRNA to render it miRNA responsive. A U6 promoter-driven expression cassette for either an anti-miR-122 or an anti-let-7 TuD RNA was inserted into the intron of the Gluc transcription unit. Reporter lacking either the seven miRNA-binding sites or the TuD expression cassette or both served as controls. miR-122 comprises 70% of total miRNAs in liver[27], posing a stringent test for the ability of TuD RNAs to inhibit the function of even the most abundant miRNA species. In vitro in HuH-7 cells, the anti-miR-122, but not anti-let-7, TuD RNA derepressed the Gluc reporter bearing seven miR-122-binding sites (FIG. 10b). Similarly, in HeLa cells anti-let-7 TuD RNA derepressed the Gluc reporter bearing seven let-7binding sites (FIG. 10c).

Both miR-122 and let-7 are present in liver[27], and let-7 is also found in heart[31]. The rAAV genomes were packaged with the AAV9 capsid, which preferentially transduces liver and heart. To further improve transduction, all rAAVs were prepared as self-complementary (sc) genomes[32]. The vectors were administered intravenously to adult male C57B/6 mice and Gluc activity was monitored in blood. Initially, Gluc activity was comparable among the animals injected with vectors expressing the miR-122-regulated reporters, irrespective of the presence of a TuD RNA expression cassette (days 3 and 7). By week 2, Gluc activity declined in the mice that received vectors lacking the antimiR-122 TuD, while Gluc activity increased in the mice treated with the anti-miR-122 TuD expressing vector (FIG. 10d). Similarly, Gluc activity was low in mice that received the let-7-regulated reporter and was high in mice that received the same reporter containing the anti-let-7 TuD expression cassette. One notable difference between the miR-122- and let-7-regulated Gluc reporters was that the let-7-regulated reporter was silenced at the earliest time point (day 3), whereas the miR-122-regulated reporter showed an initial lag in achieving silencing (FIG. 10d.e). De-repression of Gluc expression by either anti-miR-122 or anti-let-7 TuD RNA was sustained for the duration of the study, 18 weeks (FIG. 10d, e).

scAAV9-Delivered TuD RNAs Mediate Specific miRNA Depletion in Mouse Liver

Figure 11:
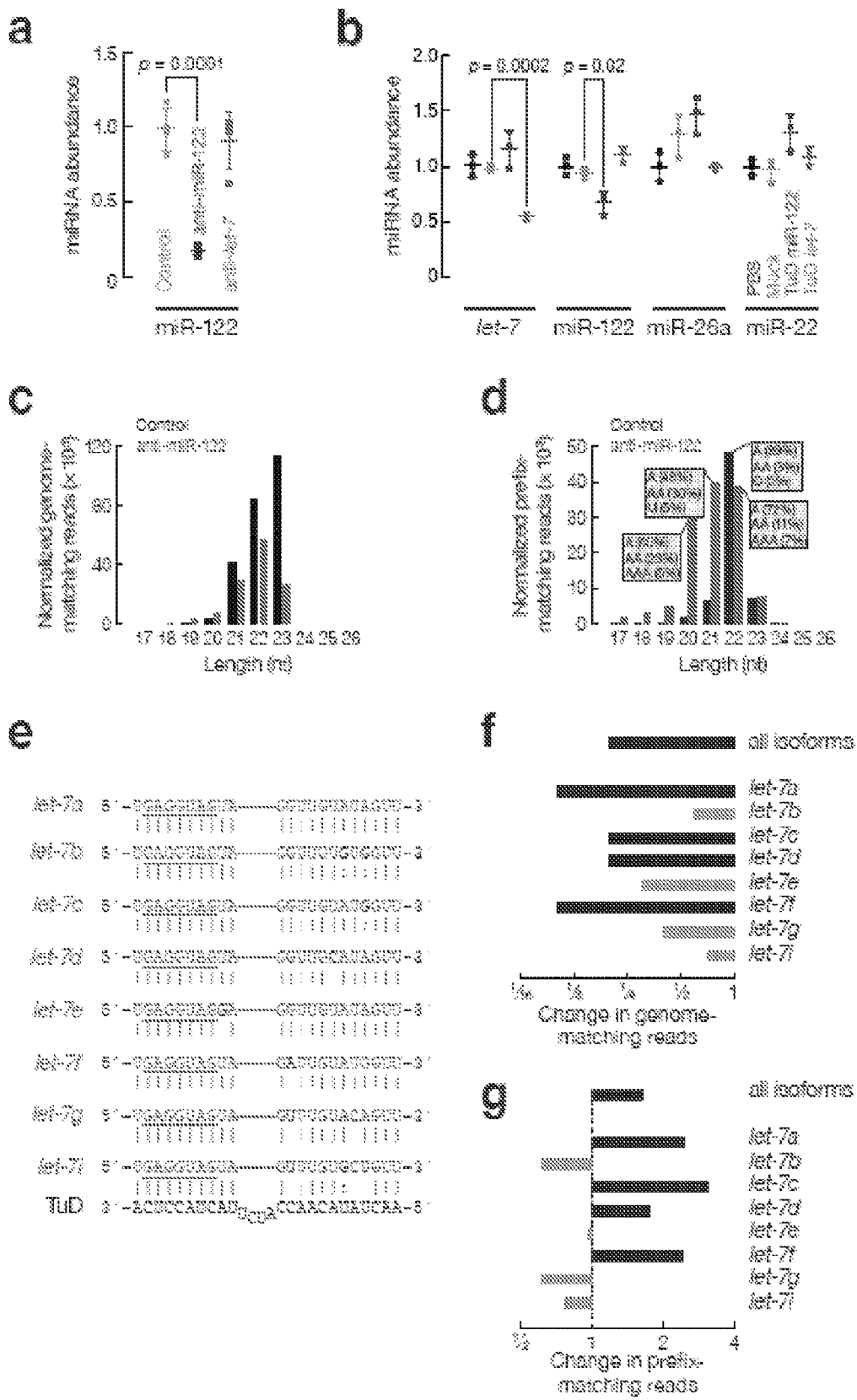
FIG. 11 Analysis of miRNA expression in liver from mice administered scAAV9 expressing anti-miRNA TuD. C57BL/6 mice were injected via tail vein with 1×10$^{12}$ genome copies of control, anti-miR-122 or anti-let-7 TuD expressing vectors. The animals were sacrificed four weeks later, and total liver RNA was prepared for qRT-PCR (a) and Northern blot (b) analyses of let-7, miR-122, miR-26a, miR-22 and U6. Data are presented as mean±standard deviation. U6 RNA provided a loading control. (c, d) High throughput sequencing of total liver small RNA was used to determine the length distribution and abundance of genome-matching miR-122 (c) or prefix-matching miR-122 (d) four weeks after scAAV injection. The most abundant non-genome matching nucleotides added to the 3' end of miR-122 fragments are indicated in the grey boxes. (e) Eight let-7 isoforms are expressed in mouse liver. Nucleotide differences among the let-7 isoforms are indicated in black and their pairing to anti-let-7 TuD RNA is shown. The "seed" sequence, an important feature for miRNA-directed target RNA recognition, is underlined. Let-7a: SEQ ID NO: 10, Let-7b: SEQ ID NO: 11, Let-7c: SEQ ID NO: 12, Let-7d: SEQ ID NO: 13, Let-7e: SEQ ID NO: 14, Let-7f: SEQ ID NO: 15, Let-7g: SEQ ID NO: 16, Let-7i: SEQ ID NO: 17, TuD: SEQ ID NO: 18. (f) The anti-let-7 TuD decreased the abundance of full-length let-7 and increased the number of prefix-matching let-7 sequence reads, relative to the control. Isoforms that decreased more than four-fold in genome-matching reads and increase in prefix-matching reads are shown in black.
Figure 12:
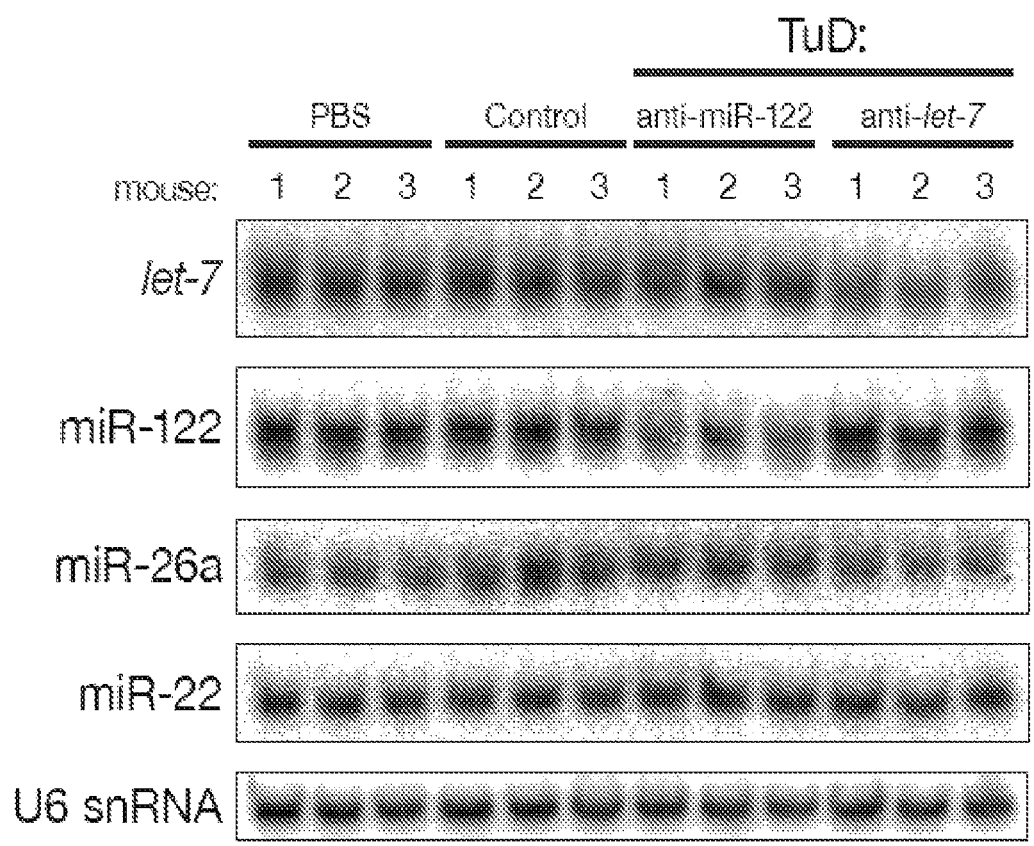
FIG. 12 Northern blot analysis of let-7, miR-122, miR-26a, miR-22 and U6 small nucleolar RNA (U6 snoRNA) in total RNA from liver of C57BL/6 mice injected with $1 \times 10^{12}$ genome copies of scAAV9CBGluc (mock), scAAV9CBGlucTuDmiR-122 (anti-miR-122 TuD) or scAAV9CBGlucTuDlet-7 (anti-let-7 TuD) via tail vein injection. The animals were sacrificed 4 weeks after injection and total liver RNA was prepared. Three biological replicates are shown and analyzed to generate FIG. 4b.

Four weeks after the administration of scAAV9 vectors, miRNA expression was analyzed in the liver using quantitative RT-PCR. An ~80% reduction in miR-122 was observed in the mice that received the anti-miR-122 TuD expressing vector, compared to vector expressing anti-let-7 TuD or control vector lacking a TuD (FIG. 11a). Northern blot analysis confirmed the reduction of miR-122 in the mice that received anti-miR-122 TuD (FIG. 11b and FIG. 12). let-7 was similarly reduced in the mice treated with scAAV9 vectors expressing the anti-let-7 TuD (the let-7 Northern probe employed cannot distinguish among the eight mouse let-7 isoforms). In contrast, no reduction was detected for miR-26a or miR-22, two other abundant liver miRNAs (FIG. 11b and FIG. 12).

High throughput sequencing of miRNAs from the treated livers further supports the view that scAAV9-delivered TuD RNAs effectively and specifically trigger the destruction of complementary miRNAs. The TuD targeting miR-122 (FIG. 7b) reduced the abundance of full-length, 23 nt miR-122 by 4.3-fold (FIG. 11c), consistent with the qRT-PCR results (FIG. 11a). The 21 and 22 nt miR-122 isoforms decreased less, whereas 20 and 19 nt isoforms increased, suggesting that the TuD triggered 3'-to-5' exonucleolytic trimming of miR-122 (FIG. 11c). Like antagomir-directed destruction of miRNAs in human cell culture[33] the anti-miR-122 TuD promoted the addition of nontemplated nucleotides to the 3' end of miR-122 (FIG. 11d). Prefix-matching reads—sequences that initially match the mouse genome but then end with non-templated nucleotides—doubled in the mouse expressing the anti-miR-122 TuD, compared to the control (FIG. 11d). The 3' non-templated nucleotides comprised one or more adenosines. Even in the absence of the TuD, 30% of miR-122 was tailed with adenosine, suggesting that miR-122 undergoes post-transcriptional modification, perhaps as part of its natural turnover.

Figures 1, 13:
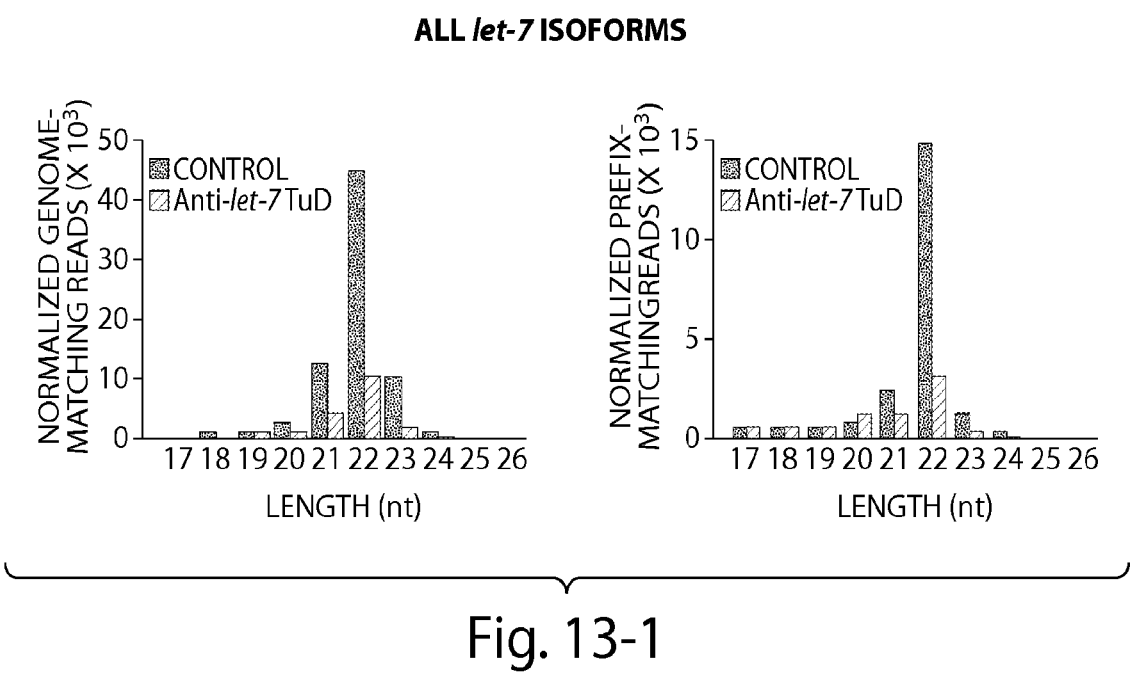
FIG. 13 Length distribution and abundance of genome-matching or prefix-matching let-7 isoform sequence reads in liver of mice 4 weeks after injection of scAAV9CBGluc (mock), scAAV9CBGlucTuD let-7 (anti-let-7 TuD). The most abundant non-templated nucleotides added to the 3' end of the miR-122 prefixes are indicated in the grey boxes. Let-7a: SEQ ID NO: 10, Let-7b: SEQ ID NO: 11, Let-7c: SEQ ID NO: 12, Let-7d: SEQ ID NO: 13, Let-7e: SEQ ID NO: 14, Let-7f: SEQ ID NO: 15, Let-7g: SEQ ID NO: 16, Let-7i: SEQ ID NO: 17, TuD: SEQ ID NO: 18.
Figures 2, 13:
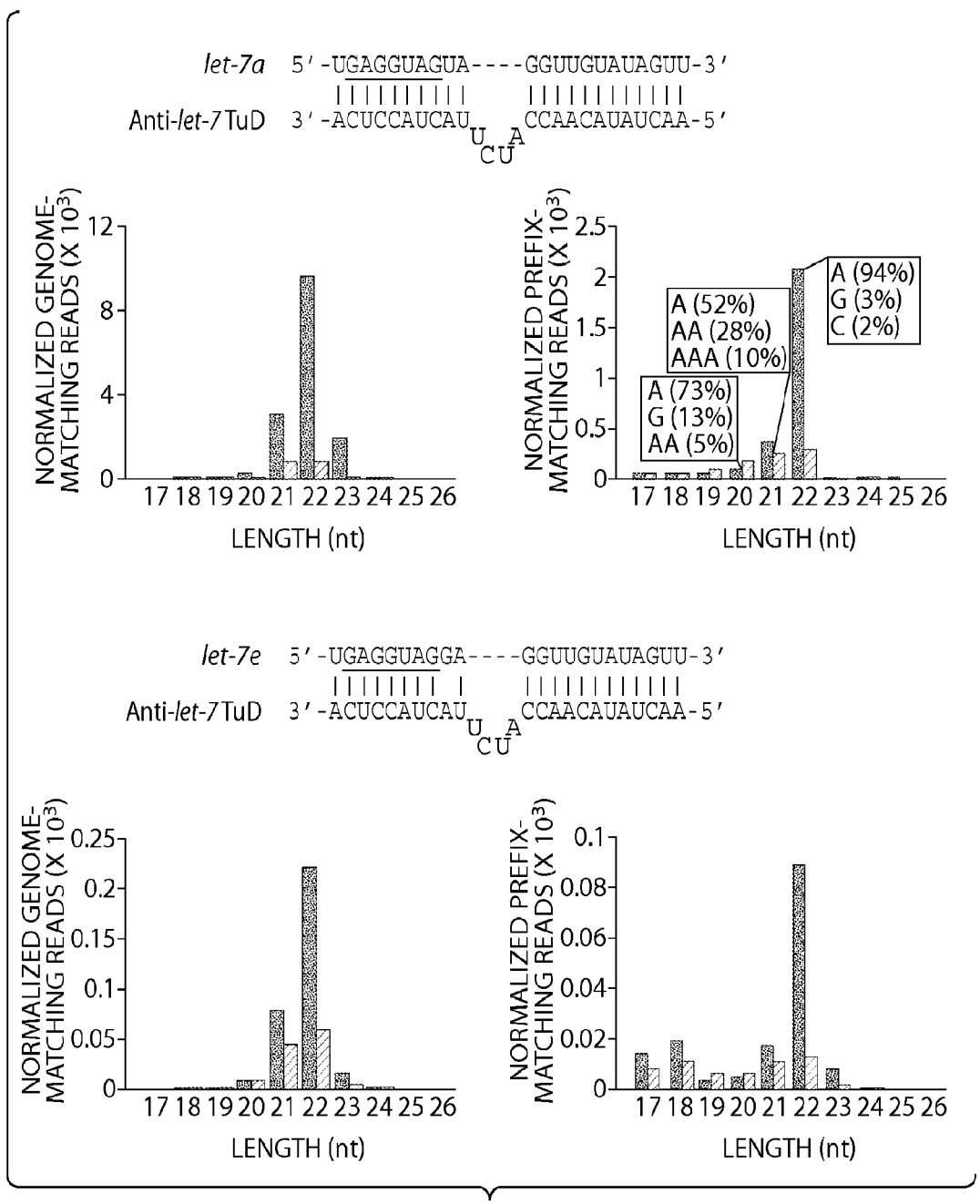
Figures 3, 13:
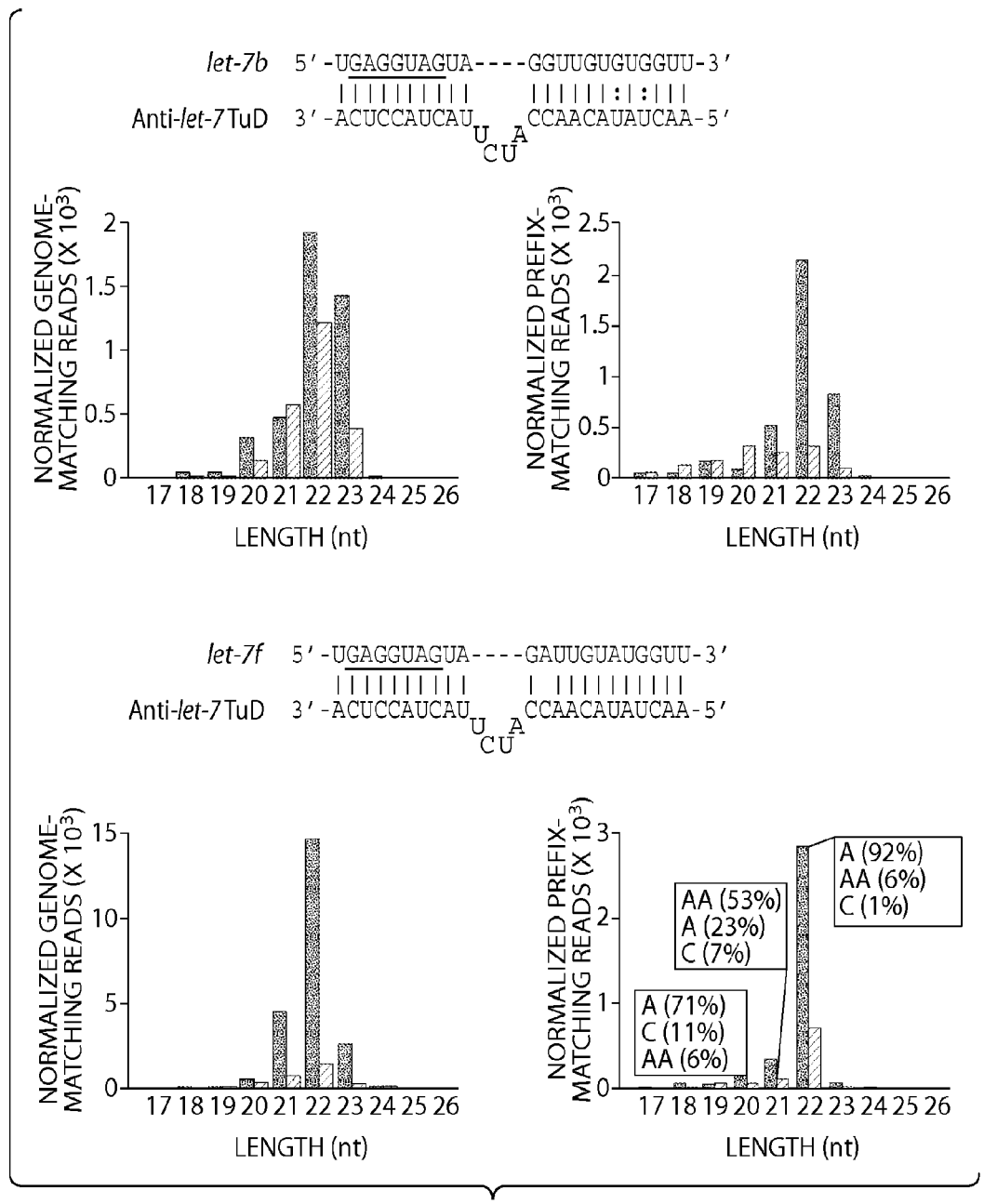
Figures 5, 13:
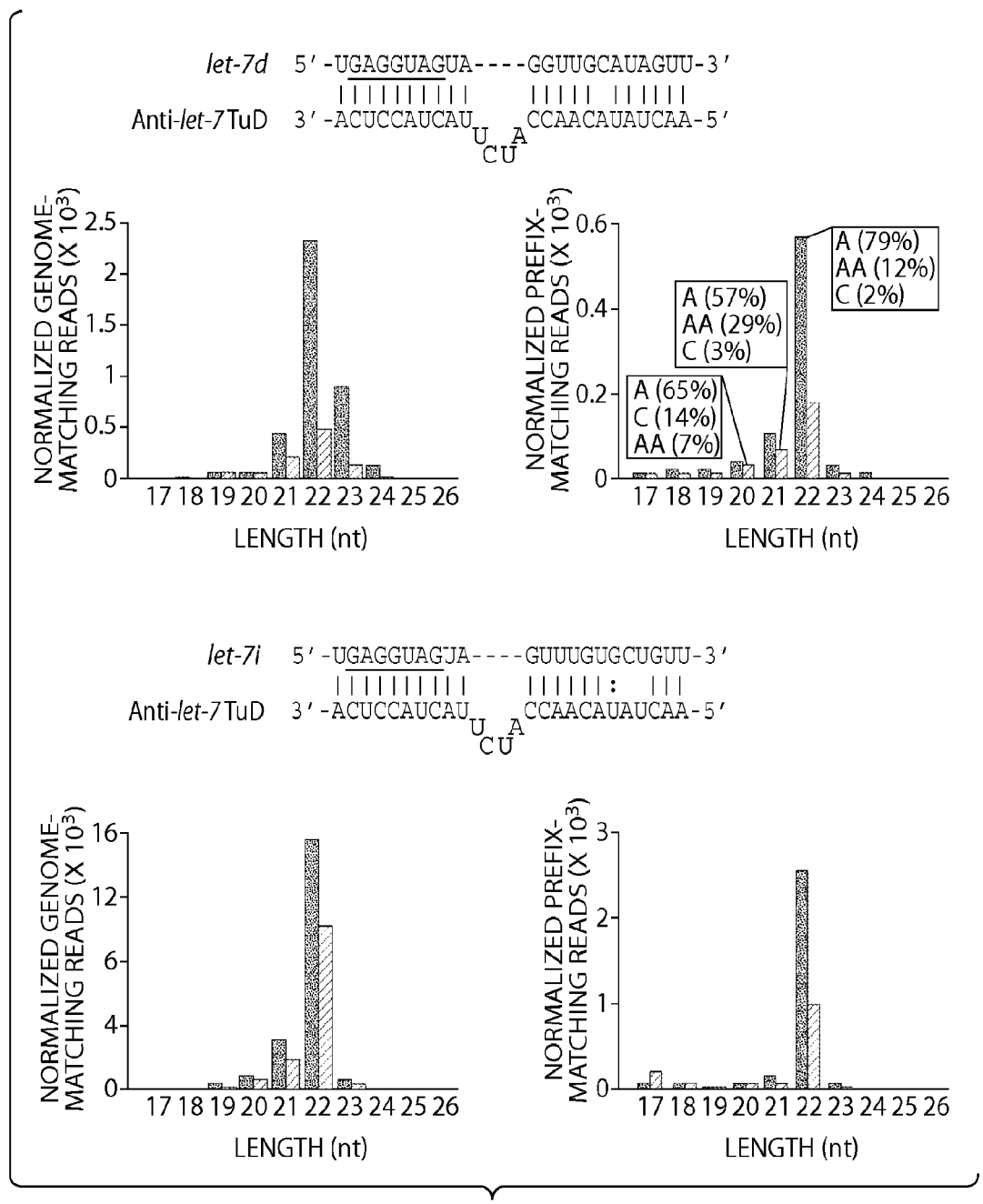
Figure 14:
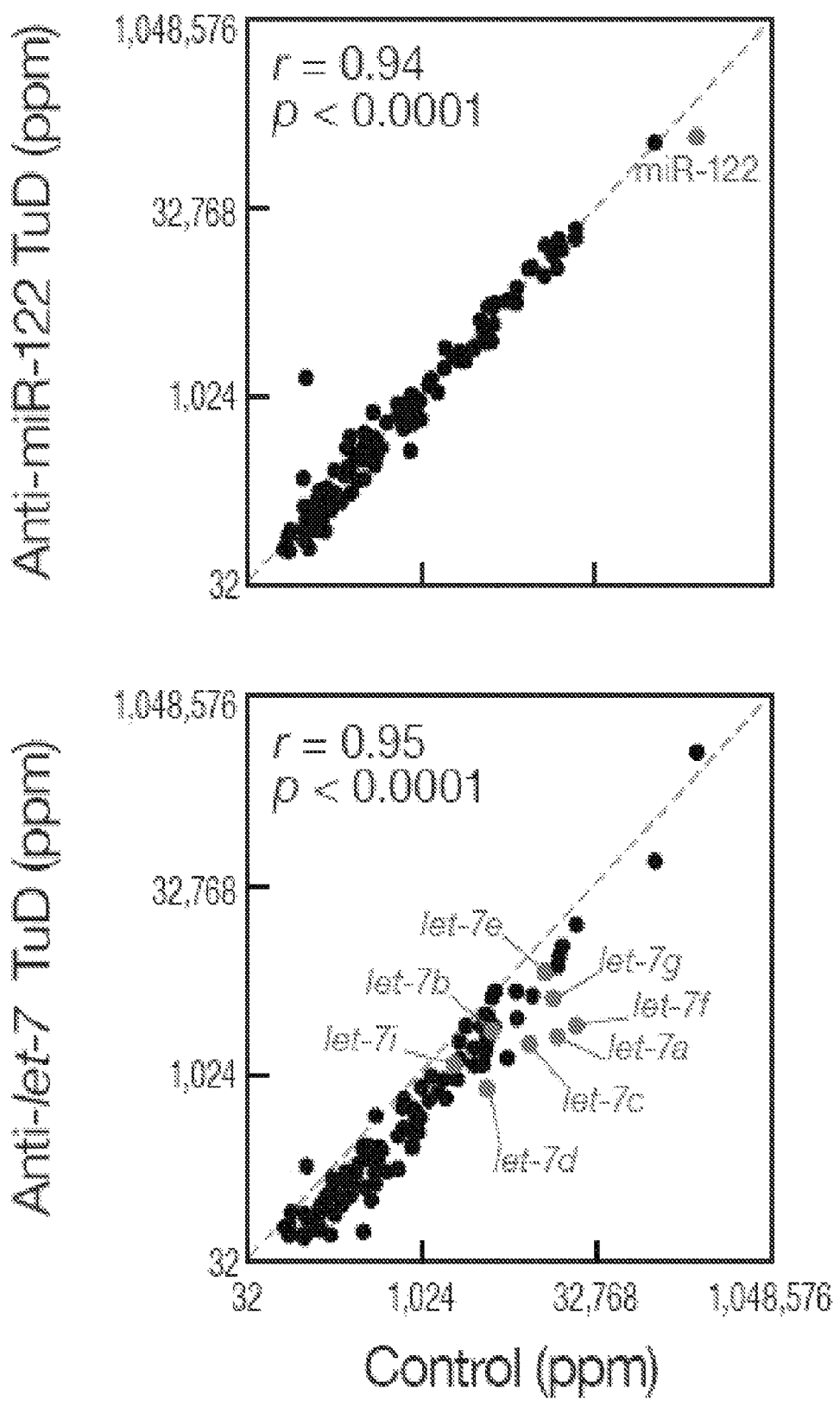
FIG. 14 Abundance of miRNAs in liver of mice 4 weeks after injection of scAAV9CBGluc (mock), scAAV9CBGlucTuD let-7 (anti-let-7 TuD) or scAAV9CBGlucTuDmiR-122 (anti-miR-122 TuD). Pearson correlation analysis was performed using GraphPad Prism V5.0b (GraphPad Software, Inc.). The correlation coefficient (r) and p-value are indicated. miRNAs targeted by TuDs are red.
Figure 15:
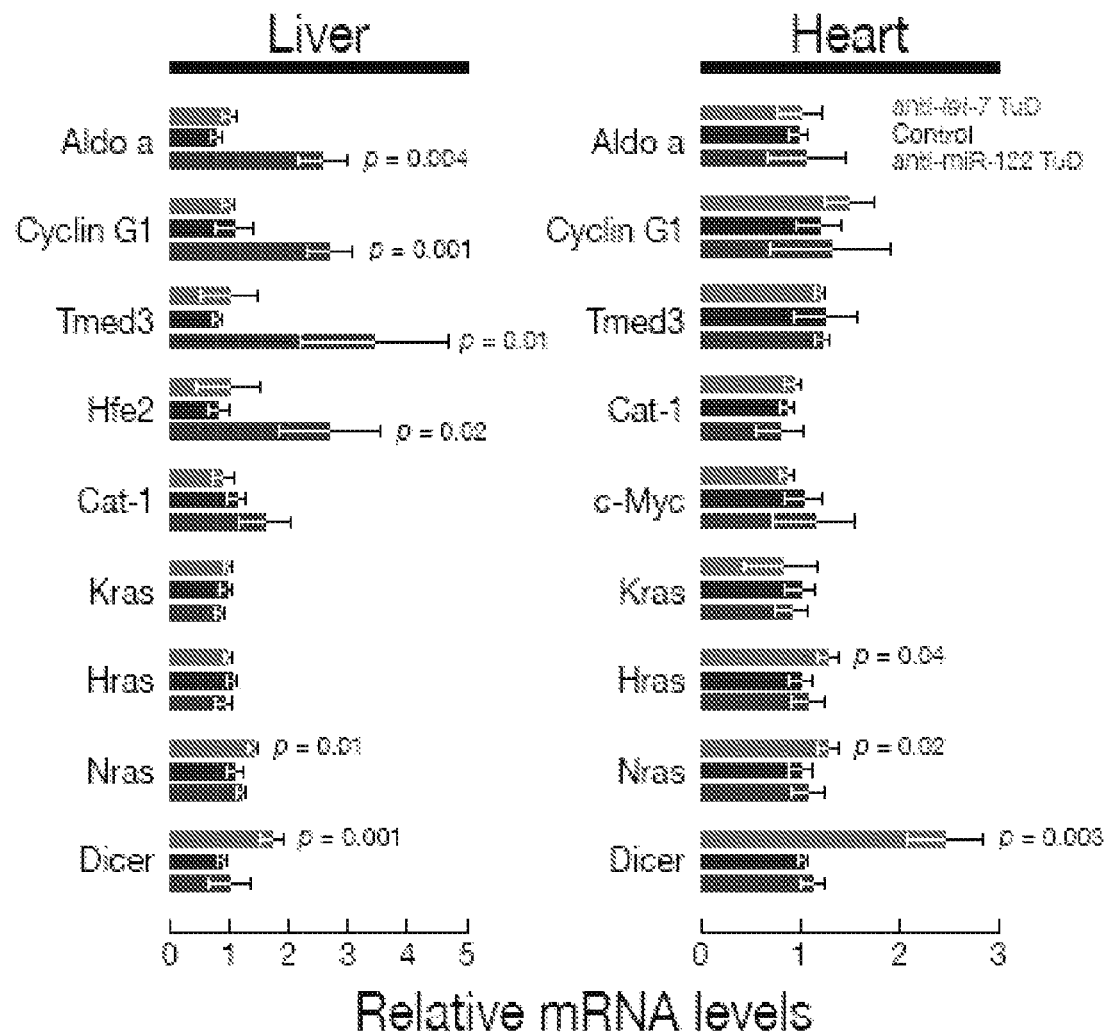
FIG. 15 Expression of natural targets of miR-122 and let-7 in TuD-treated mice. C57BL/6 mice were administered with $1 \times 10^{12}$ genome copies of control, anti-miR-122 TuD or anti-let-7 TuD scAAV9 vector via tail vein injection. The animals were sacrificed four weeks later and total liver (left panel) or heart (right panel) RNA analyzed by qRT-PCR for representative endogenous targets of miR-122 (Aldolase A, Cyclin G1, Tmed3, Hfe2, and Cat-1 mRNA) and let-7 (Kras, Hras, Nras, and Dicer mRNA). The data are presented as the mean percentage (±standard deviation) of the expression in the mice treated with the control scAAV vector.

Mouse liver expresses all eight let-7 isoforms (FIG. 13). These isoforms differ by 1-4 nucleotides outside their common seed sequence (FIG. 11e). Anti let-7 TuD strongly decreased the abundance of those full-length let-7 isoforms that were fully complementary to the TuD sequence (let-7a, 12.1-fold) or contained only a single non-seed mismatch to the TuD (let-7c, 5.1-fold; let-7d, 5.0-fold; and let-7f, 11.0-fold). In contrast, the decrease was smaller for let-7b (1.6-fold) and let-7g (2.7-fold), which contain two 3' mismatches to the TuD, let-7i (1.5-fold), which contains three 3' mismatches to the TuD, and let-7e (3.6-fold), which contains a purine:purine mismatch to the TuD at position 9, immediately flanking the seed sequence (FIG. 11e, 11f). Prefix-matching reads increased more for let-7a, c, d, and f—the let-7 isoforms that decreased the most in response to the anti-let-7 TuD—whereas let-7 b, e, g and i, which decreased least showed no increase in such trimmed-and-tailed species (FIG. 11g). These findings indicate that anti-let-7 TuD-directed miRNA decay requires nearly perfect complementarity between TuD-RNA and the miRNA. For both the anti-miR-122 and the anti-let-7 TuDs, the overall abundance of other miRNAs was unaltered (FIG. 14).

scAAV9-Delivered Anti-miRNA TuD RNAs Specifically Increase Expression of Endogenous miRNA-Regulated mRNAs When delivered using scAAV9, anti-miRNA TuD RNAs also de-repress miR-122- and let-7-regulated endogenous mRNAs (FIG. 15). qRT-PCR was used to analyze the expression of validated targets of miR-122 and let-7 in liver and heart four weeks after injection of the TuD-expressing scAAV9 vectors. Mice injected with scAAV9 expressing the Gluc reporter but with no TuD RNA served as a control. For mice treated with the vector expressing anti-miR-122 TuD RNA, a 2.5 to 3.5-fold increase in Aldolase A (3.3±0.5; p-value ≤0.04), Tmed3 (4.2±1.5; p-value ≤0.01), Hfe2 (3.3±1.0; p-value ≤0.02), and Cyclin G1 (2.5±0.4; p-value ≤0.001) mRNAs[7,34] was detected in the liver, four genes previously shown to be regulated by miR-122; expression of these four mRNAs was unaltered in the heart, which lacks miR-122 (FIG. 15). No statistically significant change in the expression of the four miR-122-regulated mRNAs was found in either liver or heart from mice that received the vector expressing anti-let-7 TuD RNA (FIG. 15).

The miRNA-producing enzyme Dicer[29] itself is repressed by let-7 family miRNAs. qRT-PCR was used to measure Dicer mRNA abundance in mice that received scAAV9 vector expressing either anti-miR-122 or anti-let-7 TuD RNA (FIG. 15). When let-7 was inhibited, Dicer mRNA was increased in both liver (1.9±0.2; p-value ≤0.001) and heart (2.4±0.4; p-value ≤0.003). The RAS family genes, HRAS, NRAS and KRAS, have been reported also to be repressed by the let-7 miRNA[35-37]. Increased expression of Nras was observed in both liver (1.3±0.1; p-value ≤0.01) and heart (1.3±0.1; p-value ≤0.02) and of HrasI (1.3±0.1; p-value ≤0.04) in heart in the mice that received scAAV9 expressing the anti-let-7, but not the anti-miR-122 TuD RNA, relative to the control (FIG. 15).

Anti-miR-122 TuD RNA Reduces Cholesterol Levels miR-122 is required for normal cholesterol biosynthesis; inhibition of miR-122 with AMOs decreases cholesterol metabolism in adult mice[7,9,11] and non-human primates[8,10]. In wild-type mice, a single intravenous injection of scAAV9 expressing anti-miR-122 RNA significantly reduced total serum cholesterol (45±5%; p-value ≤0.001) and high-density lipoprotein (HDL, 42±5%; p-value ≤0.001) levels beginning two weeks after injection, and this reduction was sustained for the 18 week duration of the study. LDL levels were also reduced (88±102%; p-value ≤0.05) by the third week and lasted for the duration of the study (FIG. 16a). Total serum cholesterol, HDL, and LDL levels were unaltered in mice that received the anti-let-7 TuD. The body weight and liver function of the mice were normal throughout the study: no weight loss (FIG. 17) or statistically significant increase in serum alanine aminotransferase (ALT) or aspartate aminotransferase (AST) levels was detected (FIG. 16b).

High cholesterol is a major risk factor for cardiovascular disease, the most common cause of morbidity and mortality in the United States. Mutations in the LDL receptor (LDLR) gene cause the common inherited dyslipidemia, familial hypercholesterolemia[38]. rAAV-mediated replacement of the LDL receptor represents a promising approach for the treatment of this genetic disorder, but may be limited by host immunity against the therapeutic gene product[39,40]. Sustained miR-122 inhibition could provide an alternative therapy for familial hypercholesterolemia. scAAV9-delivered anti-miR-122 TuD RNA was evaluated as potential treatment for familial hypercholesterolemia using a mouse model of the human disease: $LDLR^{-/-}$, Apobec $1A^{-/-}$ double mutant mice fed a normal chow diet[41]. One month after a single intravenous dose of scAAV9 expressing anti-miR-122 TuD RNA, total serum cholesterol was reduced by 34±3% (p-value ≤0.0006), serum HDL decreased 18±2% (p-value ≤0.02), and serum LDL, which is the therapeutic target for familial hypercholesterolemia in female mice, decreased 53±6% (p-value ≤0.006), compared to mice that received the scrambled TuD control (FIG. 16c). In male mice, a 21±1% (p-value ≤0.05) reduction in total cholesterol, a 26±2% (p-value ≤0.004) reduction in HDL, and a 20±1% (p-value ≤0.02) reduction in LDL was measured (FIG. 16c). The observed sex specific differences in lowering cholesterol in the $LDLR^{-/-}$, Apobec $1A^{-/-}$ mice warrant further investigation.

DISCUSSION

The large number of mammalian miRNAs makes identifying their biological functions a daunting challenge. Inhibitors of miRNA function promise to accelerate the understanding of miRNA biology, especially in adult mammals. Strategies to inhibit miRNAs include complementary chemically modified oligonucleotides and transcribed miRNA-binding competitor RNAs. While effective miRNA inhibitors, chemically modified oligonucleotides are currently expensive, some modifications are not commercially available, and require repeated dosing that risks long-term toxicity. Moreover, many tissues are not currently accessible to delivery of oligonucleotides.

Transcribed miRNA-binding RNAs provide an alternative to oligonucleotides. The small size of their transcripts makes them readily incorporated into a variety of gene transfer vectors. Primate AAV-derived vectors represent attractive tools for this application because of their unique tissue tropism, high efficiency of transduction, stability of in vivo gene transfer, and low toxicity[22,42].

Figure 16:
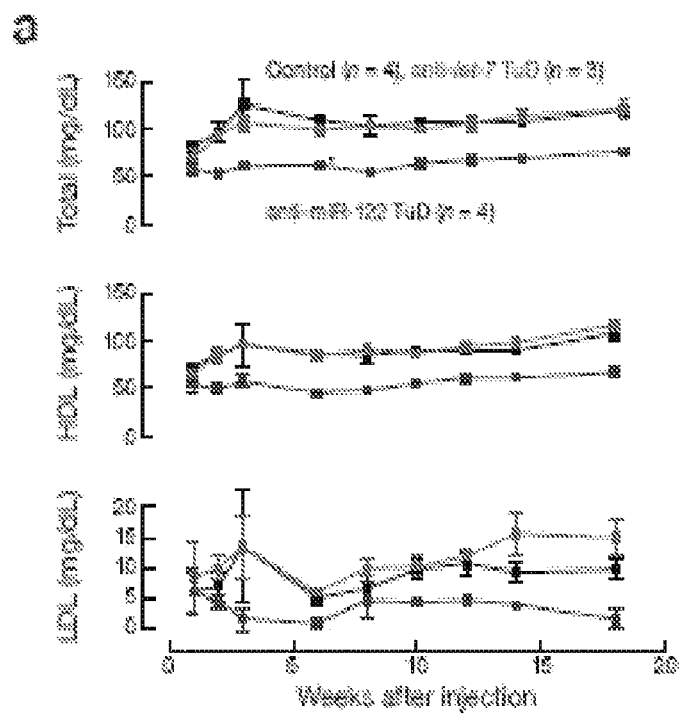
FIG. 16 Change in cholesterol profiles of wild-type C57BL/6 and hypercholesterolemic mice (LDLR$^{-/-}$, Apobec 1$^{-/-}$) after miR-122 antagonist treatment, relative to control mice. (a) Four-to-six week old male wild-type C57BL/6 mice were intravenously injected with $1 \times 10^{12}$ genome copies of scAAV9 per mouse. Serum levels of total cholesterol, high-density lipoprotein (HDL) and low-density lipoprotein (LDL) in the treated C57B/6 were measured at different time points after injection. (b) The serum transaminases aspartate, aminotransferase (ASL) and alanine aminotransferase (ALT) were assayed to assess liver toxicity. (c) Adult male (n=5 for scrambled and n=6 for anti-miR-122 TuD) and female (n=9 for scrambled and n=8 for anti-miR-122 TuD) LDLR$^{-/-}$, Apobec1$^{-/-}$ mice were administered 3×10" genome copies of scAAV9 expressing antimiR-122 by tail vein injection. The changes in total cholesterol, HDL, and LDL, relative to the control, were measured one month later. The figure reports mean±standard deviation.
Figure 16:
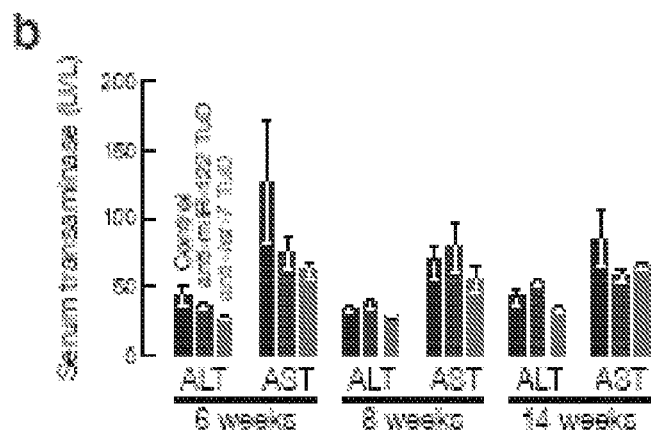
Figure 16:
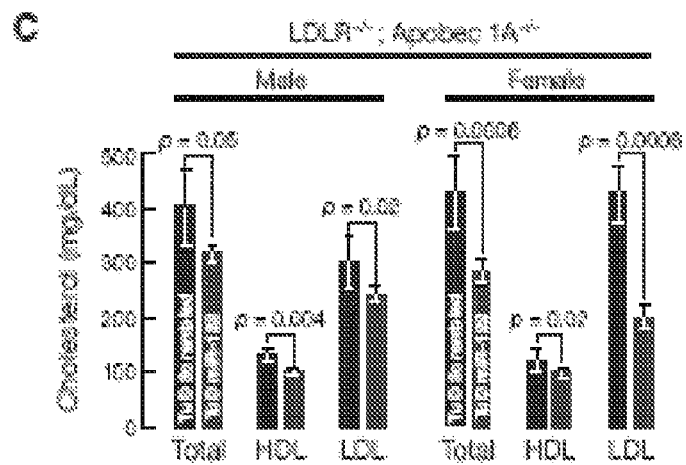
Figure 17:
FIG. 17 Body weights of the study animals. The C57BL/6 wild-type mice treated with $1 \times 10^{12}$ genome copies of scAAV9CBGluc (mock), scAAV9CBGlucTuDmiR-122 (anti-miR-122 TuD) or scAAV9CBGlucTuDlet-7 (anti-let-7 TuD) via tail vein injection were weighed 10, 12, 14, 16 and 18 weeks later. The data are mean±standard deviation.

Recently, several designs of miRNA antagonists—sponges, TuD RNAs, and miRZips—have been developed and tested in lentiviral vectors in vitro[12,15] and in genetic knockout animal models in vivo[13,14,16]. These miRNA antagonists were compared in vitro, and the most effective design, the TuD RNAs, was used in vivo to inhibit miR-122 and let-7 by incorporating TuD expression cassettes into scAVV9. The data provided herein demonstrate that a single administration of rAAV9 expressing a TuD RNA provides a stable and efficient reduction in the level of the targeted miRNA (FIG. 11), leading to an increase in expression of its endogenous target mRNAs (FIGS. 8 and 15), and a corresponding phenotypic change in metabolism (FIG. 16). The high throughput sequencing data provided herein suggest that, in mice, TuD RNAs inhibit their miRNA targets via the same target-RNA directed tailing and trimming pathway as recently described in flies for engineered[33] and endogenous mRNAs[43] and for synthetic oligonucleotide "antagomirs" in cultured human HeLa cells[33] (FIG. 11). The data presented here, which are the first observations of target RNA-directed miRNA tailing, trimming, and destruction in a living mammal, suggest that this pathway may be widely conserved among animals.

Figure 10:
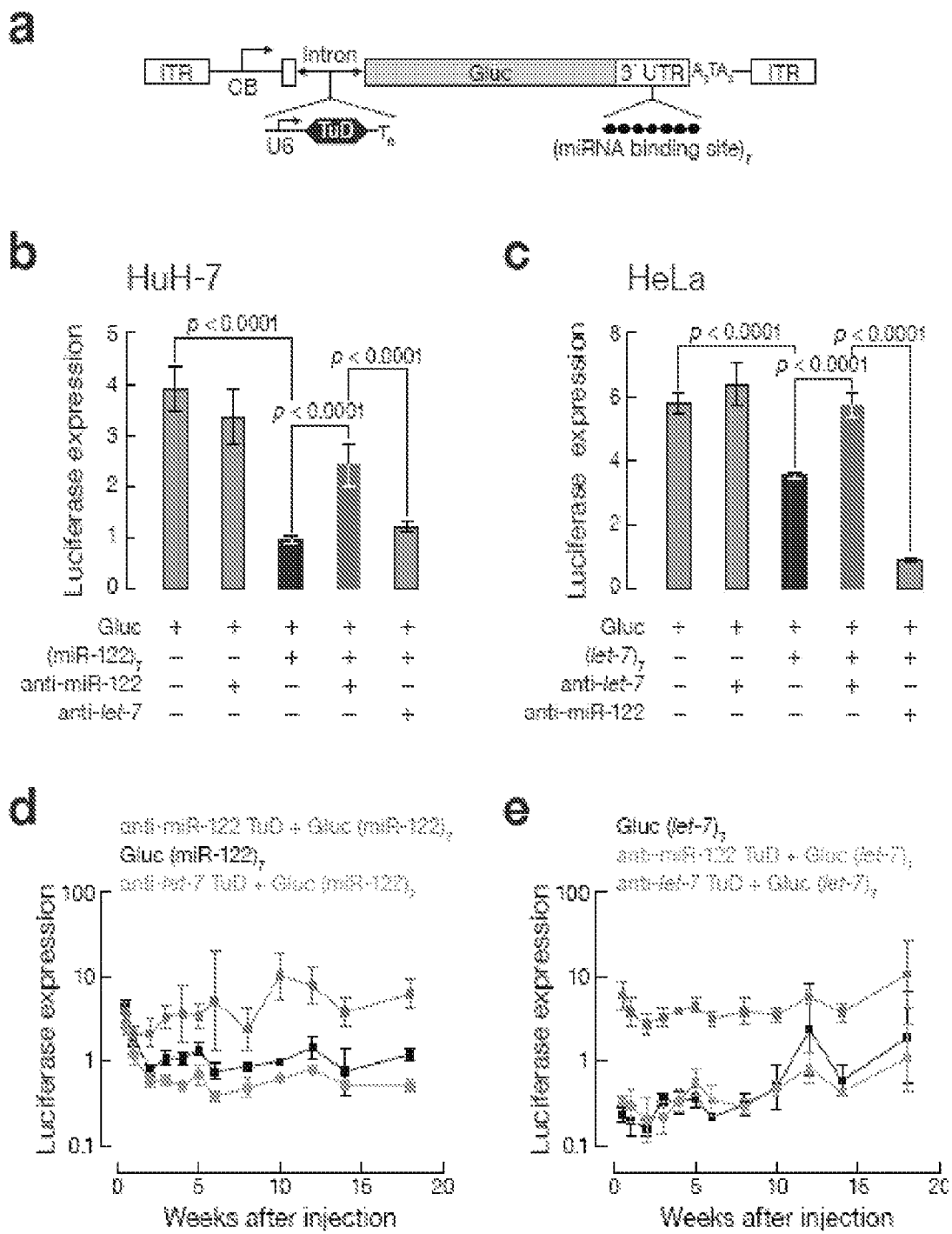
FIG. 10 Real-time monitoring of endogenous miRNA activity using miRNA sensor system. (a) Schematic presentation of Gaussia luciferase-(Gluc) expressing vectors. CB, chicken β actin promoter with CMV enhancer. AAV vector plasmids were transfected into HuH-7 (b) or HeLa cells (c). Forty-eight hours later, Gluc activity was measured. (d, e) C57BL/6 mice were administered 1×10$^{12}$ genome copies of scAAV9 per animal by tail vein injection. Blood was collected at the indicated times and assayed for Gluc activity. Gluc expression is reported as mean±standard deviation, relative to samples from mice injected with a scAAV9 vector expressing Gluc but lacking both the TuD expression cassette and the 3' UTR miRNA-binding sites. Each group had four mice.

To date, methods to monitor miRNA function in live adult mammals have not been described. The in vivo Gluc sensor system described here provides a simple means to detect changes in specific miRNA function, such as those caused by miRNA inhibitors (FIG. 10). This system allows one to assess the activity of a specific miRNA in vitro in a cell line or in vivo in a tissue or organ, providing a quantitative measure of the effectiveness of a miRNA antagonist in live animals across time.

Retrospective profiling has linked aberrant miRNA expression to a variety of diseases, suggesting that miRNAs may provide new targets for therapy[44-48]. Indeed, miR-122 inhibition by AMOs[7-11] or scAAV-delivered TuD RNA (FIG. 16) lowers both HDL and LDL. However, the current view that HDL protects against heart attack[49] argues that therapy for dyslipidemia should lower LDL but raise HDL levels. Recently, miR-33 was identified as a repressor of HDL biogenesis; miR-33 inhibition raises serum HDL level[16]. Perhaps simultaneous inhibition of miR-122 and miR-33 by a pair of TuD RNAs expressed from a single scAAV vector may achieve a more balanced and healthy cholesterol profile and provide long-lasting therapy for familial hypercholesterolemia.

Low miR-122 levels have been associated with hepatocellular carcinoma in rodents and humans[50-52], although no direct causal link has been established[51,52]. Because AAV vector expression is stable for years in rodent and primate models, animals treated with scAAV9 expressing anti-miR-122 should enable testing the safety of prolonged miR-122 inhibition in general and the increased risk of developing hepatocellular carcinoma in particular.

Materials and Methods
Construction of miRNA Antagonist and Sensor Plasmids siFluc fragment in pRNA-U6.1/Neo-siFluc (GenScript, Piscataway, N.J.) was replaced with TuD miR-122, TuD let-7, miR-122Zip, let-7Zip, miR-122 sponge and let-7 sponge that were designed as previously described[12,15] (http://www.systembio.com/microrna-research/microrna-knockdown/mirzip/) to generate U6-driven expression cassettes for expression of different miRNA antagonists. The design of let-7 antagonist was based on the consensus sequence of all let-7 family members. The XbaI-ApaI linker was generated by annealing oligonucleotide pairs, XbaI-ApaI linker F and XbaI-ApaI linker R (Table 2) followed by cloning into the ApaI site after Fluc gene in pGL3-control plasmid. The chemically synthesized miR-122 or let-7 sponge sequence flanked with XbaI and ApaI sites was digested and cloned into pGL3-XbaI-ApaI linker plasmid to create SV40 promoter-driven sponge expression cassettes. Then, the fragment containing Fluc gene and miR-122 or let-7 sponge was isolated by NcoI and ApaI double digestions from pGL3 miR-122 sponge or pGL3 let-7 sponge and cloned into the KpnI site of pAAVCBPI vector plasmid or between PstI and MluI sites of pAAVTBGPI vector plasmid to generate CB promoter and TBG promoter driven sponge expression vectors, respectively.

One or three copies of perfectly complementary miRNA target sites were designed based on the annotated miRNA sequences in miRBase[53] and inserted into the BstBI restriction site in the 3' UTR of the nLacZ expression cassette of the ubiquitously-expressed pAAVCB nuclear-targeted β-galactosidase (nLacZ) plasmid using synthetic oligonucleotides (Table 2). To express miR-122, pri-miR-122 fragment was amplified by PCR from mouse genomic DNA with specific oligonucleotides (Table 2), cloned into the XbaI restriction site right after a firefly luciferase cDNA in the pAAVCB Fluc plasmid. The identity of pri-miR-122 was verified by sequencing. scAAV9 vectors used in this study were generated, purified, and titered as previously described[18].

To create AAV vectors, seven copies of bulged target sites for miR-122 or let-7 were synthesized and cloned into BclI site after the Gluc reporter gene in the pscAAVCBPI Gluc plasmid. The EcoRI and HindIII fragment harboring U6-TuDmiR-122 or U6-TuD let-7 expression cassette was isolated from pRNA-U6.1/Neo-TuDmiR-122 or pRNA-U6.1/Neo-TuD let-7 plasmid and cloned into PpuMI site in the intron region of pscAAVCBPI Gluc with or without bulged target sites for miR-122 or let-7.

Cell Culture

HEK 293, HuH-7 and HeLa cells were cultured in Dulbecco's Modified Eagle Medium supplemented with 10% FBS and 100 mg/L of penicillin-streptomycin (HyClone, South Logan, Utah). Cells were maintained in a humidified incubator at 37° C. and 5% CO2. Plasmids were transiently transfected into cells using Lipofectamine 2000 (Invitrogen, Carlsbad, Calif.) in accordance with the manufacturer's instructions.

Luciferase Reporter Assay

Cells were lysed with passive lysis buffer (Dual-Glo Luciferase Assay System, Promega, Madison, Wis.) and 10 µl of lysis was used for the assay. Firefly and Renilla luciferase activities were assessed using the Dual-Glo Luciferase Assay System (Promega, Madison, Wis.) in accordance with the manufacturer's instructions. The Gaussia luciferase (Gluc) assay was performed following the procedure described previously[30]. Briefly, 10 µl each of culture media from the indicated transfections was used for the in vitro Gluc assay. To monitor Gluc expression in vivo, the study animals were bled from a superficial cut on facial vein made by a 5.5 mm animal lancet (MEDIpoint, Mineola, N.J.) at different time points after AAV9 vector treatment. Five µl each of blood samples was used for the Gluc assay.

Mice

C57BL/6 mice (Charles River Laboratories) and LDLR$^{-/-}$/Apobec 1A$^{-/-}$ mice (Dr. James Wilson, University of Pennsylvania) were maintained and used for the study according to the guidelines of the Institutional Animal Care and Use Committee of the University of Massachusetts Medical School. Four-to-six weeks old wild type C57BL/6 male mice were treated with AAV vectors at $1\times10^{12}$ genome copies/mouse or $5\times10^{13}$ genome copies/kg by tail vein injection. To evaluate therapeutic potential of scAAV9TuDmiR122, 4 to 6 weeks old LDLR$^{-/-}$/Apobec 1A$^{-/-}$ mice were treated with TuD-miR-122 or Scrambled vector at a dose of $3\times10^{11}$ genome copies/mouse or $1.5\times10^{13}$ genome copies/kg by tail vein injection. To monitor lipid profiles of the study animals, the serum samples were collected at different times after AAV9 vector injection and analyzed for total cholesterol, HDL and LDL on a COBAS C 111 analyzer (Roche Diagnostics, Lewes, UK). For RNA analyses, the animals were necropsied at 4 weeks after the treatment; liver and heart tissues were harvested for RNA preparation.

qRT-PCR Analysis

RNA was extracted using Trizol (Invitrogen Carlsbad, Calif.), according to the manufacturer's instructions. Total RNA (0.5-1 µg) was primed with random hexamers and reverse-transcribed with MultiScribe Reverse Transcriptase (Applied Biosystems, Foster City, Calif.). Quantitative PCR reactions were performed in triplicate with 0.3 µM gene specific primer pairs (Table 2) using the GoTaq qPCR master mix (Promega, Madison, Wis.) in a StepOne Plus Real-time PCR device (Applied Biosystems, Foster City, Calif.). The expression of mature miR-122 and U6 was assayed using the TaqMan microRNA Assay (Applied Biosystems, Foster City, Calif.).

Northern Blot Analysis

To detect miR-122, miR-26a, miR-22 and let-7 in total liver RNA, 10 µg of total RNA was resolved by denaturing 15% polyacrylamide gels, transferred to Hybond N+ membrane (Amersham BioSciences, Pittsburgh, Pa.), and cross-linked with 254 nm light (Stratagene, La Jolla, Calif.). Synthetic DNA oligonucleotides (Table 2), 5' end-labeled with γ-$^{32}$P ATP using T4 polynucleotide kinase (NEB, Beverly, Mass.), were used as probes for miR-122, miR-26a, miR-22 and let-7 and U6 (Table 2) and hybridized in Church buffer (0.5 M NaHPO4, pH 7.2, 1 mM EDTA, 7% [w/v] SDS) at 37° C. Membranes were washed using 1×SSC, 0.1% (w/v) SDS buffer, and then visualized using a FLA-5100 Imager (FUJIFILM, Tokyo, Japan).

Small RNA Sequencing

Small RNA libraries were constructed and sequenced as described[33]. Briefly, 50 µg total RNA was isolated with the mirVana kit (Ambion Foster City, Calif.), 19-29 nt small RNAs were separated and isolated through gel electrophoresis using 15% polyacrylamide/urea gel (SequaGel, National Diagnostics, Atlanta, Ga.). IDT miRNA cloning linker-1 was ligated to the 3' of small RNAs using truncated T4 RNA ligase 2 (NEB, Beverly, Mass.) and gel purified; a 5' RNA adapter was ligated to the 3' ligated RNA with T4 RNA ligase (NEB, Beverly, Mass.). The ligation product was used as template for reverse transcription with Small RNA RT primer. The cDNA was amplified with small RNA PCR primer 1 and RNA PCR primer 2. The PCR product was gel-purified and submitted for high throughput sequencing. For sequencing statistics see Tables 3 and 4. Small RNA analyses were as previously described[33]. Sequence data are available through the NCBI Short Read Archive (www.ncbi.nlm.nih.gov/sites/sra) as GSE25971.

TABLE 3

Sequencing statistics: Analysis of 5' prefix-matching reads. To detect small RNAs bearing 3' terminal, non-templated nucleotides, reads matching the reference genome for only part of their entire length were identified.

| Sample | Total reads | Reads perfectly matching genome | Reads matching annotated ncRNAs | Small RNA reads (excluding ncRNAs) | Pre miRNA matching reads |
|---|---|---|---|---|---|
| Control | 3,239,264 | 2,335,379 | 8,894 | 2,326,485 | 2,174,544 |
| anti-miR-122 TuD | 3,386,944 | 2,189,155 | 16,366 | 2,172,789 | 1,917,478 |
| anti-let-7 TuD | 1,893,012 | 1,232,744 | 4,021 | 1,228,723 | 1,163,466 |

TABLE 4

| Sample | Total reads | Prefixes matching genome | Prefixes excluding internal mm | Prefixes matching annotated ncRNAs | Prefixes (excluding ncRNAs) | Pre miRNA matching prefixes |
|---|---|---|---|---|---|---|
| Control | 3,239,264 | 903,885 | 800,519 | 1,920 | 798,599 | 568,087 |
| Anti-miR-122 TuD | 3,386,944 | 1,197,478 | 1,086,409 | 2,855 | 1,083,554 | 775,181 |
| Anti-let-7 TuD | 1,893,012 | 660,268 | 574,454 | 1,008 | 573,446 | 344,092 |

Western Blot Analysis

Proteins were extracted with RIPA buffer (25 mM Tris-HCl, pH 7.6, 150 mM NaCl, 1% NP40 [v/v], 1% sodium deoxycholate [w/v], 0.1% SDS [w/v]) containing a protease inhibitor mixture (Boston BP). Protein concentration was determined using the Bradford method. Protein samples, 50 µg each, were loaded onto 10% polyacrylamide gels, electrophoresed, and transferred to nitrocellulose membrane (Amersham BioSciences). Immunoblotting was performed using the LI-COR infrared imaging system. Briefly, membranes were blocked with blocking buffer (LI-COR) at room temperature for 2 h, followed by incubation with either anti-GAPDH (Millipore), anti-Dicer (Santa Cruz) for 2 h at room temperature. After three washes with PBS plus 0.1% Tween-20 (v/v), membranes were incubated for 1 h at room temperature using secondary antibodies conjugated to LI-COR IRDye. Signals were detected using the Odyssey Imager (LI-COR).

Statistical Analysis

All results are given as mean±standard deviation and compared between groups using the two-tailed Student's t-test, except in FIG. 16c, where the p-value was calculated using the Mann-Whitney test.

REFERENCES

1. Lewis, B. P., Burge, C. B. & Bartel, D. P. Conserved seed pairing, often flanked by adenosines, indicates that thousands of human genes are microRNA targets. *Cell* 120, 15-20 (2005).
2. Lewis, B. P., Shih, I. H., Jones-Rhoades, M. W., Bartel, D. P. & Burge, C. B. Prediction of mammalian microRNA targets. *Cell* 115, 787-98 (2003).
3. Fabani, M. M. & Gait, M. J. miR-122 targeting with LNA/2'-O-methyl oligonucleotide mixmers, peptide nucleic acids (PNA), and PNA-peptide conjugates. *RNA* 14, 336-46 (2008).
4. Hutvagner, G., Simard, M. J., Mello, C. C. & Zamore, P. D. Sequence-specific inhibition of small RNA function. *PLoS Biol* 2, E98 (2004).
5. Horwich, M. D. & Zamore, P. D. Design and delivery of antisense oligonucleotides to block microRNA function in cultured *Drosophila* and human cells. *Nat Protoc* 3, 1537-49 (2008).
6. Meister, G., Landthaler, M., Dorsett, Y. & Tuschl, T. Sequence-specific inhibition of microRNA- and siRNA-induced RNA silencing. *RNA* 10, 544-50 (2004).
7. Krutzfeldt, J. et al. Silencing of microRNAs in vivo with 'antagomirs'. *Nature* 438, 685-9 (2005).
8. Elmen, J. et al. LNA-mediated microRNA silencing in non-human primates. *Nature* 452, 896-9 (2008).
9. Elmen, J. et al. Antagonism of microRNA-122 in mice by systemically administered LNA-antimiR leads to up-regulation of a large set of predicted target mRNAs in the liver. *Nucleic Acids Res* 36, 1153-62 (2008).
10. Lanford, R. E. et al. Therapeutic silencing of microRNA-122 in primates with chronic hepatitis C virus infection. *Science* 327, 198-201 (2010).
11. Esau, C. et al. miR-122 regulation of lipid metabolism revealed by in vivo antisense targeting. *Cell Metab* 3, 87-98 (2006).
12. Ebert, M. S., Neilson, J. R. & Sharp, P. A. MicroRNA sponges: competitive inhibitors of small RNAs in mammalian cells. *Nat Methods* 4, 721-6 (2007).
13. Loya, C. M., Lu, C. S., Van Vactor, D. & Fulga, T. A. Transgenic microRNA inhibition with spatiotemporal specificity in intact organisms. *Nat Methods* 6, 897903 (2009).
14. Gentner, B. et al. Stable knockdown of microRNA in vivo by lentiviral vectors. *Nat Methods* 6, 63-6 (2009).
15. Haraguchi, T., Ozaki, Y. & Iba, H. Vectors expressing efficient RNA decoys achieve the long-term suppression of specific microRNA activity in mammalian cells. *Nucleic Acids Res* 37, e43 (2009).
16. Rayner, K. J. et al. MiR-33 contributes to the regulation of cholesterol homeostasis. *Science* 328, 1570-3 (2010).
17. Berns, K. I. & Giraud, C. Biology of adeno-associated virus. *Curr Top Microbiol Immunol* 218, 1-23 (1996).
18. Gao, G. et al. Adeno-associated viruses undergo substantial evolution in primates during natural infections. *Proc Natl Acad Sci USA* 100, 6081-6 (2003).
19. Gao, G. et al. Novel adeno-associated viruses from rhesus monkeys as vectors for human gene therapy. *Proc Natl Acad Sci USA* 99, 11854-9 (2002).
20. Gao, G. et al. Erythropoietin gene therapy leads to autoimmune anemia in macaques. *Blood* 103, 3300-2 (2004).
21. Gao, G. et al. Clades of Adeno-associated viruses are widely disseminated in human tissues. *J Virol* 78, 6381-8 (2004).
22. Gao, G., Vandenberghe, L. H. & Wilson, J. M. New recombinant serotypes of AAV vectors. *Curr Gene Ther* 5, 285-97 (2005).
23. Bish, L. T. et al. Adeno-associated virus (AAV) serotype 9 provides global cardiac gene transfer superior to AAV1, AAV6, AAV7, and AAV8 in the mouse and rat. *Hum Gene Ther* 19, 1359-68 (2008).
24. Girard, M., Jacquemin, E., Munnich, A., Lyonnet, S. & Henrion-Caude, A. miR122, a paradigm for the role of microRNAs in the liver. *J Hepatol* 48, 648-56 (2008).
25. Bussing, I., Slack, F. J. & Grosshans, H. let-7 microRNAs in development, stem cells and cancer. *Trends Mol Med* 14, 400-9 (2008).
26. Nakabayashi, H., Taketa, K., Miyano, K., Yamane, T. & Sato, J. Growth of human hepatoma cells lines with differentiated functions in chemically defined medium. *Cancer Res* 42, 3858-63 (1982).
27. Chang, J. et al. miR-122, a mammalian liver-specific microRNA, is processed from her mRNA and may down-regulate the high affinity cationic amino acid transporter CAT-1. *RNA Biol* 1, 106-13 (2004).

28. Forman, J. J., Legesse-Miller, A. & Coller, H. A. A search for conserved sequences in coding regions reveals that the let-7 microRNA targets Dicer within its coding sequence. *Proc Natl Acad Sci USA* 105, 14879-84 (2008).
29. Tokumaru, S., Suzuki, M., Yamada, H., Nagino, M. & Takahashi, T. let-7 regulates Dicer expression and constitutes a negative feedback loop. *Carcinogenesis* 29, 2073-7 (2008).
30. Tannous, B. A. Gaussia luciferase reporter assay for monitoring biological processes in culture and in vivo. *Nat Protoc* 4, 582-91 (2009).
31. Sen, C. K., Gordillo, G. M., Khanna, S. & Roy, S. Micromanaging vascular biology: tiny microRNAs play big band. *J Vasc Res* 46, 527-40 (2009).
32. McCarty, D. M. Self-complementary AAV vectors; advances and applications. *Mol Ther* 16, 1648-56 (2008).
33. Ameres, S. L. et al. Target RNA-directed trimming and tailing of small silencing RNAs. *Science* 328, 1534-9 (2010).
34. Gramantieri, L. et al. Cyclin G1 is a target of miR-122a, a microRNA frequently down-regulated in human hepatocellular carcinoma. *Cancer Res* 67, 6092-9 (2007).
35. Johnson, S. M. et al. RAS is regulated by the let-7 microRNA family. *Cell* 120, 635-47 (2005).
36. Yu, F. et al. let-7 regulates self renewal and tumorigenicity of breast cancer cells. *Cell* 131, 1109-23 (2007).
37. Christensen, B. C. et al. A let-7 microRNA-binding site polymorphism in the KRAS 3' UTR is associated with reduced survival in oral cancers. *Carcinogenesis* 30, 1003-7 (2009).
38. Soutar, A. K. & Naoumova, R. P. Mechanisms of disease: genetic causes of familial hypercholesterolemia. *Nat Clin Pract Cardiovasc Med* 4, 214-25 (2007).
39. Lebherz, C. et al. Gene therapy with novel adeno-associated virus vectors substantially diminishes atherosclerosis in a murine model of familial hypercholesterolemia. *J Gene Med* 6, 663-72 (2004).
40. Gao, G. et al. Adeno-associated virus-mediated gene transfer to nonhuman primate liver can elicit destructive transgene-specific T cell responses. *Hum Gene Ther* 20, 930-42 (2009).
41. Powell-Braxton, L. et al. A mouse model of human familial hypercholesterolemia: markedly elevated low density lipoprotein cholesterol levels and severe atherosclerosis on a low-fat chow diet. *Nat Med* 4, 934-8 (1998).
42. Vandenberghe, L. H., Wilson, J. M. & Gao, G. Tailoring the AAV vector capsid for gene therapy. *Gene Ther* 16, 311-9 (2009).
43. Ameres, S. L., Hung, J. H., Xu, J., Weng, Z. & Zamore, P. D. Target RNA-directed tailing and trimming purifies the sorting of endo-siRNAs between the two *Drosophila* Argonaute proteins. *RNA in press* (2010).
44. Care, A. et al. MicroRNA-133 controls cardiac hypertrophy. *Nat Med* 13, 613-8 (2007).
45. Kota, J. et al. Therapeutic microRNA delivery suppresses tumorigenesis in a murine liver cancer model. *Cell* 137, 1005-17 (2009).
46. Ma, L. et al. Therapeutic silencing of miR-10b inhibits metastasis in a mouse mammary tumor model. *Nat Biotechnol* 28, 341-7 (2010).
47. Waldman, S. A. & Terzic, A. Applications of microRNA in cancer: Exploring the advantages of miRNA. *Clin Transl Sci* 2, 248-9 (2009).
48. Yang, B. et al. The muscle-specific microRNA miR-1 regulates cardiac arrhythmogenic potential by targeting GJA1 and KCNJ2. *Nat Med* 13, 486-91 (2007).
49. McGovern, M. E. Taking aim at HDL-C. Raising levels to reduce cardiovascular risk. *Postgrad Med* 117, 29-30, 33-5, 39 passim (2005).
50. Kutay, H. et al. Downregulation of miR-122 in the rodent and human hepatocellular carcinomas. *J Cell Biochem* 99, 671-8 (2006).
51. Coulouarn, C., Factor, V. M., Andersen, J. B., Durkin, M. E. & Thorgeirsson, S. S. Loss of miR-122 expression in liver cancer correlates with suppression of the hepatic phenotype and gain of metastatic properties. *Oncogene* 28, 3526-36 (2009).
52. Tsai, W. C. et al. MicroRNA-122, a tumor suppressor microRNA that regulates intrahepatic metastasis of hepatocellular carcinoma. *Hepatology* 49, 1571-82 (2009).
53. Griffiths-Jones, S., Grocock, R. J., van Dongen, S., Bateman, A. & Enright, A. J. miRBase: microRNA sequences, targets and gene nomenclature. *Nucleic Acids Res* 34, D140-4 (2006).

The entire contents of references 1-53 listed above, and of all other references, publications, or database entries identified herein are incorporated into this application by reference as if each individual reference, publication, or database entry was incorporated herein by reference individually. In case of a conflict, the instant disclosure shall control.

This invention is not limited in its application to the details of construction and the arrangement of components set forth in this description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for treating a high cholesterol-related disorder in a subject, the method comprising:

administering an effective amount of a recombinant Adeno-Associated Virus (rAAV) to the subject, wherein the rAAV comprises at least one transgene that expresses a miRNA inhibitor that inhibits the expression of miR-122 in the subject, and wherein the miRNA inhibitor comprises or consists of a sequence as set forth in SEQ ID NO: 1, SEQ ID NO: 5, SEQ ID NO: 21, or SEQ ID NO: 23.

2. The method of claim 1, wherein the miRNA inhibitor comprises an miR-122 binding site.

3. The method of claim 1, wherein the miR-122 binding site is flanked by two stem sequences.

4. The method of claim 1, wherein the miR-122 binding site comprises a non-binding, central portion that is not complementary with miR-122, flanked by two portions that are complementary with miR-122.

5. The method of claim 1, wherein the miRNA inhibitor comprises a first miR-122 binding site and a second miR-122 binding site, wherein a first stem sequence flanks the first miR-122 binding site at its 5'-end, a second stem sequence flanks the first miR-122 binding site at its 3'-end and the second miR-122 binding site at its 5'-end, and a third stem sequence flanks the second miR-122 binding site at its 3'-end.

6. The method of claim 1, wherein the miRNA inhibitor comprises two or more miR-122 binding sites.

7. The method of claim 1, wherein the rAAV has a capsid of the AAV9 serotype, which has a sequence as set forth in SEQ ID NO: 3.

8. The method of claim 1, wherein the rAAV has a capsid that is a variant of the capsid of the AAV9 serotype.

9. The method of claim 8, wherein the rAAV has a capsid of the AAV9 serotype variant, Csp-3, which has a sequence as set forth in SEQ ID NO: 4.

10. The method of claim 1, wherein the rAAV targets liver tissue.

11. The method of claim 1, wherein the rAAV transduces hepatocytes.

12. The method of claim 1, wherein administering is performed intravenously.

* * * * *

UNITED STATES PATENT AND TRADEMARK OFFICE
CERTIFICATE OF CORRECTION

| | | |
|---|---|---|
| PATENT NO. | : 9,272,053 B2 | Page 1 of 1 |
| APPLICATION NO. | : 13/642740 | |
| DATED | : March 1, 2016 | |
| INVENTOR(S) | : Guangping Gao et al. | |

It is certified that error appears in the above-identified patent and that said Letters Patent is hereby corrected as shown below:

In the Specification:

At column 1, line 15, please cancel the following paragraph:

"GOVERNMENT SUPPORT

This work was supported under grant nos. P01 HL5940711, 2R37GM62862 and 2R01GM65236 awarded by the National Institutes of Health. The U.S. government as certain rights in the invention."

And insert the following paragraph:

--STATEMENT AS TO FEDERALLY SPONSORED RESEARCH

This invention was made with U.S. Government support under Grant Nos. P01 HL5940711, 2R37GM62862, and 2R01GM65236 awarded by the National Institutes of Health. The Government has certain rights in the invention.--

Signed and Sealed this
Third Day of May, 2016

Michelle K. Lee
*Director of the United States Patent and Trademark Office*

SEQUENCE LISTING

<160> NUMBER OF SEQ ID NOS: 66

<210> SEQ ID NO 1
<211> LENGTH: 150

```
<212> TYPE: DNA
<213> ORGANISM: Artificial Sequence
<220> FEATURE:
<223> OTHER INFORMATION: Synthetic polynucleotide

<400> SEQUENCE: 1
ggatccgacg cgctaggat catcaaccaa acaccattga tcttcacact ccacaagtat    60
tctggtcaca gaatacaacc aaacaccatt gatcttcaca ctccacaaga tgatcctagc   120
gccgtctttt ttaagcttga agacaatagc                                    150

<210> SEQ ID NO 2
<211> LENGTH: 150
<212> TYPE: DNA
<213> ORGANISM: Artificial Sequence
<220> FEATURE:
<223> OTHER INFORMATION: Synthetic polynucleotide

<400> SEQUENCE: 2
ggatccgacg cgctaggat catcaacaac tatacaacca tcttactacc tcacaagtat    60
tctggtcaca gaatacaaca actatacaac catcttacta cctcacaaga tgatcctagc   120
gccgtctttt ttaagcttga agacaatagc                                    150

<210> SEQ ID NO 3
<211> LENGTH: 736
<212> TYPE: PRT
<213> ORGANISM: Adeno-associated virus

<400> SEQUENCE: 3
```

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

```
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
```

```
                           645                 650                 655
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Adeno-associated virus

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Ile Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Arg Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Arg Val Lys Glu Val Thr Asp Asn Asn Gly Val Lys Thr Ile Thr Asn
                    325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Arg Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                    565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Val
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
```

```
                705                 710                 715                 720
Tyr Ser Glu Pro Arg Pro Ile Gly Thr Arg Tyr Leu Thr Arg Asn Leu
                725                 730                 735
```

<210> SEQ ID NO 5
<211> LENGTH: 123
<212> TYPE: RNA
<213> ORGANISM: Artificial Sequence
<220> FEATURE:
<223> OTHER INFORMATION: Synthetic polynucleotide

<400> SEQUENCE: 5

```
gacggcgcua ggaucaucaa cacaaacacc auugaucuuc acacuccaca aguauucugg    60
ucacagaaua caacacaaac accauugauc uucacacucc acaagaugau ccuagcgccg   120
ucu                                                                 123
```

<210> SEQ ID NO 6
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 6

```
uggaguguga caauguguu ugu                                             23
```

<210> SEQ ID NO 7
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 7

```
acaaacacca uacaacacuc ca                                             22
```

<210> SEQ ID NO 8
<211> LENGTH: 27
<212> TYPE: RNA
<213> ORGANISM: Artificial Sequence
<220> FEATURE:
<223> OTHER INFORMATION: Synthetic polynucleotide

<400> SEQUENCE: 8

```
acaaacacca uugaucuuca cacucca                                        27
```

<210> SEQ ID NO 9
<211> LENGTH: 23
<212> TYPE: RNA
<213> ORGANISM: Artificial Sequence
<220> FEATURE:
<223> OTHER INFORMATION: Synthetic polynucleotide

<400> SEQUENCE: 9

```
acaaacacca uugucacacu cca                                            23
```

<210> SEQ ID NO 10
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 10
ugagguagua gguuguauag uu                                        22

<210> SEQ ID NO 11
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 11
ugagguagua gguugugugg uu                                        22

<210> SEQ ID NO 12
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 12
ugagguagua gguuguaugg uu                                        22

<210> SEQ ID NO 13
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 13
ugagguagua gguugcauag uu                                        22

<210> SEQ ID NO 14
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 14
ugagguagga gguuguauag uu                                        22

<210> SEQ ID NO 15
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 15
ugagguagua gauuguaugg uu                                        22

<210> SEQ ID NO 16
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 16
ugagguagua guuuguacag uu                                        22

<210> SEQ ID NO 17
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 17
ugagguagua guuugugcug uu                                          22

<210> SEQ ID NO 18
<211> LENGTH: 26
<212> TYPE: RNA
<213> ORGANISM: Artificial Sequence
<220> FEATURE:
<223> OTHER INFORMATION: Synthetic polynucleotide

<400> SEQUENCE: 18
aacuauacaa ccaucuuacu accuca                                      26

<210> SEQ ID NO 19
<211> LENGTH: 138
<212> TYPE: DNA
<213> ORGANISM: Artificial Sequence
<220> FEATURE:
<223> OTHER INFORMATION: Synthetic polynucleotide

<400> SEQUENCE: 19
ggatccgacg gcgctaggat catcaaccaa acaccattga tcttcacact ccacaagtat    60
tctggtcaca gaatacaacc aaacaccatt gatcttcaca ctccacaaga tgatcctagc   120
gccgtctttt ttgaattc                                                138

<210> SEQ ID NO 20
<211> LENGTH: 138
<212> TYPE: DNA
<213> ORGANISM: Artificial Sequence
<220> FEATURE:
<223> OTHER INFORMATION: Synthetic polynucleotide

<400> SEQUENCE: 20
ggatccgacg gcgctaggat catcaacaac tatacaacca tcttactacc tcacaagtat    60
tctggtcaca gaatacaaca actatacaac catcttacta cctcacaaga tgatcctagc   120
gccgtctttt ttgaattc                                                138

<210> SEQ ID NO 21
<211> LENGTH: 82
<212> TYPE: DNA
<213> ORGANISM: Artificial Sequence
<220> FEATURE:
<223> OTHER INFORMATION: Synthetic polynucleotide

<400> SEQUENCE: 21
ggatcctggt cagtgacaat gtttgcttcc tgtcagacaa acaccattgt cacactccat    60
ttttaagctt gaagacaata gc                                           82

<210> SEQ ID NO 22
<211> LENGTH: 85
<212> TYPE: DNA
<213> ORGANISM: Artificial Sequence
<220> FEATURE:
<223> OTHER INFORMATION: Synthetic polynucleotide

<400> SEQUENCE: 22
ggatcctctc gtagtaggtt gtatagttct tcctgtcaga aactatacaa cctactacct    60
catttttaag cttgaagaca atagc                                        85

<210> SEQ ID NO 23
<211> LENGTH: 159
<212> TYPE: DNA
<213> ORGANISM: Artificial Sequence
<220> FEATURE:
<223> OTHER INFORMATION: Synthetic polynucleotide

<400> SEQUENCE: 23
tctagacaaa caccatacaa cactccacaa acaccataca acactccaca aacaccatac      60
aacactccac aaacaccata caacactcca caaacaccat acaacactcc acaaacacca     120
tacaacactc cacaaacacc atacaacact ccagggccc                            159

<210> SEQ ID NO 24
<211> LENGTH: 161
<212> TYPE: DNA
<213> ORGANISM: Artificial Sequence
<220> FEATURE:
<223> OTHER INFORMATION: Synthetic polynucleotide

<400> SEQUENCE: 24
tctagaaact atacaaaacc tacctcaaac cacacaaaac ctacctcaaa ccatacaaaa      60
cctacctcaa actatgcaaa acctacctct aactatacaa aacctacctc aaactgtaca     120
aaacctacct caaaccatac aaaacctacc tcagccctag a                         161

<210> SEQ ID NO 25
<211> LENGTH: 159
<212> TYPE: DNA
<213> ORGANISM: Artificial Sequence
<220> FEATURE:
<223> OTHER INFORMATION: Synthetic polynucleotide

<400> SEQUENCE: 25
tctagacaaa caccatacaa caagaaacaa acaccataca acaagaaaca aacaccatac      60
aacaagaaac aaacaccata caacaagaaa caaacaccat acaacaagaa acaaacacca     120
tacaacaaga aacaaacacc atacaacaag aaagggccc                            159

<210> SEQ ID NO 26
<211> LENGTH: 159
<212> TYPE: DNA
<213> ORGANISM: Artificial Sequence
<220> FEATURE:
<223> OTHER INFORMATION: Synthetic polynucleotide

<400> SEQUENCE: 26
tctagaaact atacaaaacc taaagaaaac cacacaaaac ctaaagaaaa ccatacaaaa      60
cctaaagaaa actatgcaaa acctaaagat aactatacaa aacctaaaga aaactgtaca     120
aaacctaaag aaaaccatac aaaacctaaa gaagggccc                            159

<210> SEQ ID NO 27
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 27
cgaaacaaac accattgtca cactccatt                                        29

<210> SEQ ID NO 28
<211> LENGTH: 29

```
<212> TYPE: DNA
<213> ORGANISM: Artificial Sequence
<220> FEATURE:
<223> OTHER INFORMATION: Synthetic polynucleotide

<400> SEQUENCE: 28
cgaatggagt gtgacaatgg tgtttgttt                                          29

<210> SEQ ID NO 29
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 29
cgaaacaaac accattgtca cactccaaca aacaccattg tcacactcca acaaacacca        60
ttgtcacact ccatt                                                         75

<210> SEQ ID NO 30
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 30
cgaatggagt gtgacaatgg tgtttgttgg agtgtgacaa tggtgtttgt tggagtgtga        60
caatggtgtt tgttt                                                         75

<210> SEQ ID NO 31
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 31
ctagattccg agatatcggt aatgggcc                                           28

<210> SEQ ID NO 32
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 32
ggcccattac cgatatctcg gaatctag                                           28

<210> SEQ ID NO 33
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 33
atcgggcccg actgcagttt cagcgtttg                                          29

<210> SEQ ID NO 34
<211> LENGTH: 29
<212> TYPE: DNA
<213> ORGANISM: Artificial Sequence
<220> FEATURE:
```

<223> OTHER INFORMATION: Synthetic polynucleotide

<400> SEQUENCE: 34
cgcgggcccg actttacatt acacacaat                                              29

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 35
tggacacagc tggacaagag                                                        20

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 36
ctgtccttgt tggcaagtca                                                        20

<210> SEQ ID NO 37
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 37
caagagcgcc ttgacgatac a                                                      21

<210> SEQ ID NO 38
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 38
ccaagagaca ggtttctcca tc                                                     22

<210> SEQ ID NO 39
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 39
cgtgagattc ggcagcataa a                                                      21

<210> SEQ ID NO 40
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 40
gacagcacac atttgcagct c                                                      21

```
<210> SEQ ID NO 41
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 41
gcaggctttt tacacacgcc t                                              21

<210> SEQ ID NO 42
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 42
gggtcttcat aaaggtgctt                                                20

<210> SEQ ID NO 43
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 43
caacgtcttg gaacgtcaga                                                20

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 44
tcgtctgctt gaatggacag                                                20

<210> SEQ ID NO 45
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 45
ggggaccttg ctttccactc                                                20

<210> SEQ ID NO 46
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 46
gcctcatagt cacagggatc t                                              21

<210> SEQ ID NO 47
<211> LENGTH: 19
<212> TYPE: DNA
<213> ORGANISM: Artificial Sequence
<220> FEATURE:
<223> OTHER INFORMATION: Synthetic polynucleotide
```

<400> SEQUENCE: 47
agcagggcgt gaagttctc                                                    19

<210> SEQ ID NO 48
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 48
ttgtacgtga agctgtcata ctg                                               23

<210> SEQ ID NO 49
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
tgggaagaag gagaacctga                                                   20

<210> SEQ ID NO 50
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 50
agtgttgatg gagcagcctt                                                   20

<210> SEQ ID NO 51
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 51
taccagtggc cgtgtttgta                                                   20

<210> SEQ ID NO 52
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 52
gctgttgcca agcttctacc                                                   20

<210> SEQ ID NO 53
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 53
aatggcctca gaatgactgc                                                   20

<210> SEQ ID NO 54
<211> LENGTH: 20

```
<212> TYPE: DNA
<213> ORGANISM: Artificial Sequence
<220> FEATURE:
<223> OTHER INFORMATION: Synthetic polynucleotide

<400> SEQUENCE: 54
agtcgctttc acagccaaat                                                    20

<210> SEQ ID NO 55
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 55
atgccaacac agtgctgtct gg                                                 22

<210> SEQ ID NO 56
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 56
tgcttgctga tccacatctg ct                                                 22

<210> SEQ ID NO 57
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 57
tggagtgtga caatggtgtt tg                                                 22

<210> SEQ ID NO 58
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 58
aactatacaa cctactacct ca                                                 22

<210> SEQ ID NO 59
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 59
agcctatcct ggattacttg aa                                                 22

<210> SEQ ID NO 60
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 60
```
acagttcttc aactggcagc tt    22

<210> SEQ ID NO 61
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 61
ctctgtatcg ttccaattt agtata    26

<210> SEQ ID NO 62
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 62
actgtaggca ccatcaatc    19

<210> SEQ ID NO 63
<211> LENGTH: 26
<212> TYPE: RNA
<213> ORGANISM: Artificial Sequence
<220> FEATURE:
<223> OTHER INFORMATION: Synthetic polynucleotide

<400> SEQUENCE: 63
guucagaguu cuacaguccg acgauc    26

<210> SEQ ID NO 64
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 64
attgatggtg cctacag    17

<210> SEQ ID NO 65
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 65
caagcagaag acggcatacg aattgatggt gcctacag    38

<210> SEQ ID NO 66
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 66
aatgatacgg cgaccaccga caggttcaga gttctacagt ccga    44